(12) United States Patent
Belson et al.

(10) Patent No.: US 10,159,825 B2
(45) Date of Patent: Dec. 25, 2018

(54) RAPID CLOSING SURGICAL CLOSURE DEVICE

(71) Applicant: ZIPLINE MEDICAL, INC., Campbell, CA (US)

(72) Inventors: Amir Belson, Los Altos, CA (US); Brian Beckey, Woodside, CA (US); James J. Leary, St. Louis, CA (US)

(73) Assignee: ZipLine Medical, Inc., Campbell, CA (US)

( * ) Notice: Subject to any disclaimer, the term of this patent is extended or adjusted under 35 U.S.C. 154(b) by 119 days.

(21) Appl. No.: 14/851,059

(22) Filed: Sep. 11, 2015

(65) Prior Publication Data

US 2016/0095597 A1 Apr. 7, 2016

Related U.S. Application Data

(63) Continuation-in-part of application No. 13/414,176, filed on Mar. 7, 2012, now Pat. No. 9,179,914, which
(Continued)

(51) Int. Cl.
*A61B 17/08* (2006.01)
*A61M 39/02* (2006.01)
(Continued)

(52) U.S. Cl.
CPC ............. *A61M 39/02* (2013.01); *A61B 17/08* (2013.01); *A61B 17/085* (2013.01); *A61M 5/142* (2013.01);
(Continued)

(58) Field of Classification Search
CPC ... A61B 17/085; A61B 17/0057; A61B 17/08; A61B 17/083; A61B 2017/086;
(Continued)

(56) References Cited

U.S. PATENT DOCUMENTS 2,012,755 A 8/1935 De Muth
2,371,978 A 3/1945 Perham
(Continued)

FOREIGN PATENT DOCUMENTS

CN 1126430 A 7/1996
CN 1442119 A 9/2003
(Continued)

OTHER PUBLICATIONS

Co-pending U.S. Appl. No. 15/081,526, filed Mar. 25, 2016.
(Continued)

*Primary Examiner* — Katrina Stransky
(74) *Attorney, Agent, or Firm* — Wilson Sonsini Goodrich and Rosati, P.C.

(57) ABSTRACT

A surgical or wound closure device utilizes a slide fastener for rapidly closing a surgical incision or wound with precise apposition of the sides of the incision. The surgical closure devices are configured for linear incisions, shaped incisions, such as used for wedge biopsy or excisional biopsy, and long incisions, such as used for laparotomy or surgical removal of redundant skin. The surgical closure device may be adhered to the patient's skin prior to making an incision and is subsequently used for closing the incision.

29 Claims, 85 Drawing Sheets

Related U.S. Application Data is a continuation of application No. PCT/US2010/000430, filed on May 3, 2010.

(60) Provisional application No. 61/243,423, filed on Sep. 17, 2009.

(51) Int. Cl.
| | |
|---|---|
| *A61M 5/32* | (2006.01) |
| *A61M 5/28* | (2006.01) |
| *A61M 5/142* | (2006.01) |
| *A61N 1/32* | (2006.01) |
| *A61M 5/24* | (2006.01) |
| *A61M 25/06* | (2006.01) |
| *A61M 39/04* | (2006.01) |
| *A61M 5/158* | (2006.01) |
| *A61M 25/00* | (2006.01) |
| *A61M 37/00* | (2006.01) |
| *A61F 13/00* | (2006.01) |
| *A61B 17/00* | (2006.01) |
| *A61B 17/32* | (2006.01) |

(52) U.S. Cl.
CPC ...... *A61M 5/14248* (2013.01); *A61M 5/2425* (2013.01); *A61M 5/28* (2013.01); *A61M 5/3298* (2013.01); *A61M 25/065* (2013.01); *A61M 39/04* (2013.01); *A61N 1/326* (2013.01); *A61N 1/327* (2013.01); *A61B 2017/00889* (2013.01); *A61B 2017/00893* (2013.01); *A61B 2017/081* (2013.01); *A61B 2017/086* (2013.01); *A61B 2017/088* (2013.01); *A61B 2017/320052* (2013.01); *A61F 2013/0017* (2013.01); *A61M 2005/1581* (2013.01); *A61M 2005/1586* (2013.01); *A61M 2025/0057* (2013.01); *A61M 2037/0007* (2013.01); *A61M 2039/0205* (2013.01); *A61M 2202/0478* (2013.01)

(58) Field of Classification Search
CPC ....... A61B 2017/088; A61B 2017/081; A61M 39/0208; A61M 5/142; A61M 5/14248; A61M 5/3298; A61M 5/28
See application file for complete search history.

(56) References Cited

U.S. PATENT DOCUMENTS

| | | |
|---|---|---|
| 2,747,248 A | 5/1956 | Mercer |
| 3,118,201 A | 1/1964 | Beghetto, Jr. |
| 3,487,836 A | 1/1970 | Niebel et al. |
| 3,516,409 A | 6/1970 | Howell |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 3,983,878 A | 10/1976 | Kawchitch |
| 4,038,989 A | 8/1977 | Romero-Sierra et al. |
| 4,114,624 A | 9/1978 | Haverstock |
| 4,210,148 A | 7/1980 | Stivala |
| 4,222,383 A | 9/1980 | Schossow |
| 4,224,945 A | 9/1980 | Cohen |
| 4,526,173 A | 7/1985 | Sheehan |
| 4,531,521 A | 7/1985 | Haverstock |
| 4,535,772 A | 8/1985 | Sheehan |
| 4,539,990 A | 9/1985 | Stivala |
| 4,576,163 A | 3/1986 | Bliss |
| 4,605,005 A | 8/1986 | Sheehan |
| 4,612,230 A | 9/1986 | Liland et al. |
| 4,676,245 A | 6/1987 | Fukuda |
| 4,702,251 A | 10/1987 | Sheehan |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A | 12/1990 | Haverstock |
| 5,176,703 A | 1/1993 | Peterson |
| 5,190,032 A | 3/1993 | Zacoi |
| 5,259,835 A | 11/1993 | Clark et al. |
| 5,306,236 A | 4/1994 | Blumenfeld et al. |
| 5,336,219 A | 8/1994 | Krantz |
| 5,377,695 A | 1/1995 | An Haack |
| 5,514,155 A | 5/1996 | Daneshvar |
| 5,533,519 A | 7/1996 | Radke et al. |
| 5,562,705 A | 10/1996 | Whiteford |
| 5,665,108 A | 9/1997 | Galindo |
| 5,725,507 A | 3/1998 | Petrick |
| 5,788,660 A | 8/1998 | Resnik |
| 5,823,983 A | 10/1998 | Rosofsky et al. |
| 5,843,123 A | 12/1998 | Brazeau |
| 6,007,564 A | 12/1999 | Haverstock |
| 6,033,654 A | 3/2000 | Stedronsky et al. |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,629,949 B1 * | 10/2003 | Douglas ............... A61M 5/142 604/19 |
| 6,689,100 B2 | 2/2004 | Connelly et al. |
| 6,726,706 B2 | 4/2004 | Dominguez |
| 7,066,182 B1 | 6/2006 | Dunshee |
| 7,361,185 B2 | 4/2008 | O'Malley et al. |
| 7,455,681 B2 | 11/2008 | Wilke et al. |
| 7,511,185 B2 | 3/2009 | Lebner |
| 7,641,682 B2 | 1/2010 | Palmaz et al. |
| 7,645,285 B2 | 1/2010 | Cosgrove et al. |
| 7,799,042 B2 | 9/2010 | Williamson, IV et al. |
| 8,246,590 B2 | 8/2012 | Hu et al. |
| 8,313,508 B2 | 11/2012 | Belson et al. |
| 8,323,313 B1 | 12/2012 | Belson et al. |
| 8,439,945 B2 | 5/2013 | Belson et al. |
| 8,592,640 B2 | 11/2013 | Zepeda et al. |
| 8,663,275 B2 | 3/2014 | O'Malley et al. |
| 9,008,784 B2 | 4/2015 | Chan et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,271,858 B2 | 3/2016 | Ben-Meir et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Belson et al. |
| 9,642,621 B2 | 5/2017 | Belson et al. |
| 9,642,622 B2 | 5/2017 | Belson et al. |
| 2002/0099315 A1 | 7/2002 | Lebner |
| 2003/0065294 A1 | 4/2003 | Pickup et al. |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 | 4/2004 | Udding et al. |
| 2004/0106904 A1 | 6/2004 | Gonnelli et al. |
| 2004/0204740 A1 | 10/2004 | Weiser |
| 2004/0210176 A1 | 10/2004 | Diana |
| 2004/0260234 A1 | 12/2004 | Srinivasan et al. |
| 2005/0020956 A1 | 1/2005 | Lebner |
| 2005/0020957 A1 | 1/2005 | Lebner |
| 2005/0070956 A1 | 3/2005 | Rousseau |
| 2005/0080453 A1 | 4/2005 | Lebner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 | 12/2005 | Tacklind |
| 2006/0030886 A1 | 2/2006 | Clark |
| 2006/0122522 A1 | 6/2006 | Chavan et al. |
| 2006/0200198 A1 | 9/2006 | Riskin et al. |

(56) References Cited

U.S. PATENT DOCUMENTS

| | | |
|---|---|---|
| 2006/0259033 A1 | 11/2006 | Nesbitt |
| 2007/0026078 A1 | 2/2007 | Almarsson et al. |
| 2007/0038247 A1 | 2/2007 | Lebner et al. |
| 2007/0078366 A1 | 4/2007 | Haggstrom et al. |
| 2007/0088339 A1 | 4/2007 | Luchetti et al. |
| 2007/0106277 A1 | 5/2007 | Hood et al. |
| 2007/0141130 A1 | 6/2007 | Villanueva et al. |
| 2007/0179419 A1 | 8/2007 | Simpson |
| 2007/0185432 A1* | 8/2007 | Etheredge, III ..... A61B 17/205 604/21 |
| 2007/0260278 A1 | 11/2007 | Wheeler et al. |
| 2008/0033334 A1 | 2/2008 | Gurtner et al. |
| 2008/0069855 A1 | 3/2008 | Bonutti |
| 2008/0081951 A1 | 4/2008 | Frasier et al. |
| 2008/0103550 A1 | 5/2008 | Wenzel et al. |
| 2008/0114396 A1* | 5/2008 | Cory .................... A61B 17/085 606/216 |
| 2008/0147115 A1 | 6/2008 | O'Malley et al. |
| 2008/0161731 A1 | 7/2008 | Woods et al. |
| 2008/0228219 A1 | 9/2008 | Weiser |
| 2008/0287864 A1* | 11/2008 | Rosenberg ........... A61B 17/205 604/60 |
| 2009/0036922 A1 | 2/2009 | Riskin et al. |
| 2009/0062531 A1 | 3/2009 | Kanda |
| 2009/0099496 A1 | 4/2009 | Heegaard et al. |
| 2009/0149869 A1 | 6/2009 | Lhun |
| 2009/0158131 A1 | 6/2009 | Choi et al. |
| 2009/0162531 A1 | 6/2009 | Nesbitt |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2010/0280545 A1 | 11/2010 | Fridman |
| 2011/0077667 A1 | 3/2011 | Singhatat et al. |
| 2011/0106026 A1 | 5/2011 | Wu et al. |
| 2011/0144470 A1 | 6/2011 | Mazar et al. |
| 2012/0016410 A1 | 1/2012 | Belson et al. |
| 2012/0029266 A1 | 2/2012 | Holmes et al. |
| 2012/0095502 A1 | 4/2012 | Bargon et al. |
| 2012/0116279 A1 | 5/2012 | Munro et al. |
| 2012/0116485 A1 | 5/2012 | Burgmann |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0267928 A1 | 10/2013 | Imran et al. |
| 2013/0281885 A1 | 10/2013 | Rowbottom et al. |
| 2013/0281981 A1 | 10/2013 | Shamir Lebovitz |
| 2013/0282049 A1 | 10/2013 | Peterson et al. |
| 2013/0296930 A1 | 11/2013 | Belson et al. |
| 2013/0331757 A1 | 12/2013 | Belson |
| 2014/0074156 A1 | 3/2014 | Belson et al. |
| 2014/0171849 A1 | 6/2014 | Fischell et al. |
| 2014/0222070 A1 | 8/2014 | Belson et al. |
| 2014/0228712 A1 | 8/2014 | Elliott et al. |
| 2014/0278229 A1 | 9/2014 | Hong et al. |
| 2014/0316323 A1 | 10/2014 | Kanevsky et al. |
| 2015/0045700 A1 | 2/2015 | Cavanagh et al. |
| 2015/0105423 A1 | 4/2015 | Haudenschild et al. |
| 2015/0148653 A1 | 5/2015 | Fleig et al. |
| 2015/0209563 A1 | 7/2015 | Amir |
| 2015/0216527 A1 | 8/2015 | Belson et al. |
| 2015/0309535 A1 | 10/2015 | Connor et al. |
| 2015/0313593 A1 | 11/2015 | Patenaude et al. |
| 2015/0351690 A1 | 12/2015 | Toth et al. |
| 2016/0007909 A1 | 1/2016 | Singh et al. |
| 2016/0106931 A1 | 4/2016 | Belson et al. |
| 2016/0114146 A1 | 4/2016 | Belson et al. |
| 2016/0202755 A1 | 7/2016 | Connor |
| 2016/0206311 A1 | 7/2016 | Belson et al. |
| 2016/0206312 A1 | 7/2016 | Belson et al. |
| 2016/0206313 A1 | 7/2016 | Belson et al. |
| 2016/0213924 A1 | 7/2016 | Coleman et al. |
| 2016/0220175 A1 | 8/2016 | Tam et al. |
| 2016/0220252 A1 | 8/2016 | Belson et al. |
| 2016/0242646 A1 | 8/2016 | Obma |
| 2016/0249924 A1 | 9/2016 | Belson et al. |
| 2016/0296149 A1 | 10/2016 | Polsky et al. |
| 2016/0302721 A1 | 10/2016 | Wiedenhoefer et al. |
| 2016/0310140 A1 | 10/2016 | Belson et al. |
| 2017/0035422 A1 | 2/2017 | Belson et al. |
| 2017/0042541 A1 | 2/2017 | Belson et al. |
| 2017/0143341 A1 | 5/2017 | Belson et al. |
| 2017/0156664 A1 | 6/2017 | Belson et al. |

FOREIGN PATENT DOCUMENTS

| | | |
|---|---|---|
| CN | 1524507 A | 9/2004 |
| CN | 1234327 C | 1/2006 |
| CN | 101938944 A | 1/2011 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 A | 8/1975 |
| JP | S5223497 | 6/1977 |
| JP | S62243557 A | 10/1987 |
| JP | H07502913 A | 3/1995 |
| JP | 2001149485 A | 6/2001 |
| JP | 2005512678 A | 5/2005 |
| JP | 2005522134 A | 10/2005 |
| JP | 2010504835 A | 2/2010 |
| JP | 2013515417 A | 5/2013 |
| JP | 2013538603 A | 10/2013 |
| WO | WO-8401805 A1 | 5/1984 |
| WO | WO-9629013 A1 | 9/1996 |
| WO | WO-03053296 A1 | 7/2003 |
| WO | WO-2006124671 A2 | 11/2006 |
| WO | WO-2007004603 A1 | 1/2007 |
| WO | WO-2007044647 A2 | 4/2007 |
| WO | WO-2008019051 A2 | 2/2008 |
| WO | WO-2008060532 A2 | 5/2008 |
| WO | WO-2009066116 A1 | 5/2009 |
| WO | WO-2011019859 A2 | 2/2011 |
| WO | WO-2011019859 A3 | 4/2011 |
| WO | WO-2011043786 A1 | 4/2011 |
| WO | WO-2011139912 A1 | 11/2011 |
| WO | WO-2011159623 A1 | 12/2011 |
| WO | WO-2013067024 A1 | 5/2013 |
| WO | WO-2014066879 A2 | 5/2014 |
| WO | WO-2014070922 A1 | 5/2014 |
| WO | WO-2015012887 A1 | 1/2015 |
| WO | WO-2015103556 A1 | 7/2015 |
| WO | WO-2015168165 A1 | 11/2015 |
| WO | WO-2017027075 A1 | 2/2017 |
| WO | WO-2017044120 A1 | 3/2017 |
| WO | WO-2017181059 A1 | 10/2017 |
| WO | WO-2017184825 A1 | 10/2017 |
| WO | WO-2018081795 | 5/2018 |

OTHER PUBLICATIONS

Co-pending U.S. Appl. No. 15/081,550, filed Mar. 25, 2016.
Co-pending U.S. Appl. No. 15/081,595, filed Mar. 25, 2016.
Co-pending U.S. Appl. No. 15/130,149, filed Apr. 15, 2016.
Co-pending U.S. Appl. No. 15/096,083, filed Apr. 11, 2016.
Co-pending U.S. Appl. No. 15/130,764, filed Apr. 15, 2016.
Merriam-Webster Dictionary. Definition of "lateral". Http://www.merriam-webster.com/dictionary/lateral. Accessed on May 5, 2016.
Notice of allowance dated Jun. 21, 2016 for U.S. Appl. No. 15/081,526.
Office action dated May 3, 2016 for U.S. Appl. No. 13/665,160.

(56) References Cited

OTHER PUBLICATIONS

Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
Office action dated Jun. 17, 2016 for U.S. Appl. No. 15/130,149.
International search report and written opinion dated Aug. 30, 2016 for PCT/US2016/028297.
Co-pending U.S. Appl. No. 15/337,768, filed Oct. 28, 2016.
Co-pending U.S. Appl. No. 15/369,293, filed Dec. 5, 2016.
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.
Office action dated Feb. 1, 2017 for U.S. Appl. No. 15/130,764.
Office action dated Nov. 17, 2016 for U.S. Appl. No. 15/081,595.
Office action dated Dec. 1, 2016 for U.S. Appl. No. 13/665,160.
Co-pending U.S. Appl. No. 15/201,088, filed Jul. 1, 2016.
European search report and opinion dated Jul. 12, 2016 for EP Application No. 13851258.
Office action dated Jul. 20, 2016 for U.S. Appl. No. 15/130,764.
Zip® Surgical Skin Closure. Fast, non-invasive alternative to staples, sutures and glue. Accessed Aug. 17, 2016. http://www.ziplinemedical.com/products/zip-surgical-skin-closure/.
"International search report and written opinion dated Jan. 12, 2016 for PCT Application No. US2015/049671."
"K984204, 510(k) Premarket Notification Summary, Silverlon™ Direct Pressure Wound Closure Strip, May 19, 2007."
Office action dated Mar. 4, 2016 for U.S. Appl. No. 13/874,046.
Co-pending U.S. Appl. No. 14/851,059, filed Sep. 11, 2015.
Co-pending U.S. Appl. No. 14/958,803, filed Dec. 3, 2015.
Co-pending U.S. Appl. No. 14/958,818, filed Dec. 3, 2015.
Hasson, et al. A new sutureless technique for skin closure. Arch Surg. Jan. 1976;111(1):83-4.
Office action dated Mar. 21, 2012 for U.S. Appl. No. 13/286,378.
Office action dated Mar. 22, 2012 for U.S. Appl. No. 13/286,757.
Office action dated Jul. 23, 2012 for U.S. Appl. No. 13/286,378.
Office action dated Jul. 23, 2012 for U.S. Appl. No. 13/286,757.
Office action dated Aug. 28, 2014 for U.S. Appl. No. 14/180,524.
Office action dated Oct. 14, 2015 for U.S. Appl. No. 13/685,909.
Office action dated Oct. 23, 2015 for U.S. Appl. No. 13/665,160.
European search report and opinion dated Jan. 7, 2014 for EP Application No. 11778067.6.
European search report and opinion dated Jan. 7, 2014 for EP Application No. 11796253.0.
European search report and opinion dated Apr. 29, 2015 for EP Application No. 10822334.8.
European search report and written opinion dated Aug. 12, 2015 for EP Application No. 12844746.3.
International search report and written opinion dated Feb. 6, 2014 for PCT/US2013/067563.
International search report and written opinion dated Mar. 19, 2013 for PCT/US2012/062820.
International search report and written opinion dated Apr. 29, 2015 for PCT/US2015/010188.
International search report and written opinion dated Jul. 29, 2011 for PCT/US2011/034649.
International search report and written opinion dated Jul. 30, 2010 for PCT/US2010/000430.
International search report and written opinion dated Sep. 10, 2014 for PCT/US2014/016587.
International search report and written opinion dated Sep. 30, 2015 for PCT Application No. US2015/28066.
International search report and written opinion dated Oct. 21, 2011 for PCT Application No. US11/40213.
Notice of allowance dated Jan. 17, 2013 for U.S. Appl. No. 13/096,602.
Notice of allowance dated Feb. 10, 2015 for U.S. Appl. No. 14/180,524.
Notice of allowance dated Sep. 17, 2012 for U.S. Appl. No. 13/286,378.
Notice of allowance dated Sep. 20, 2012 for U.S. Appl. No. 13/286,757.
Notice of allowance dated Sep. 22, 2015 for U.S. Appl. No. 13/414,176.
Notice of allowance dated Dec. 19, 2014 for U.S. Appl. No. 14/180,564.
Office action dated Feb. 26, 2015 for U.S. Appl. No. 13/414,176.
Office action dated Mar. 21, 2014 for U.S. Appl. No. 13/414,176.
Office action dated Apr. 7, 2015 for U.S. Appl. No. 13/685,909.
Office action dated May 2, 2012 for U.S. Appl. No. 13/096,602.
Office action dated Jun. 5, 2015 for U.S. Appl. No. 13/874,046.
Office action dated Jun. 17, 2014 for U.S. Appl. No. 13/414,176.
Office action dated Aug. 18, 2014 for U.S. Appl. No. 14/180,564.
Office action dated Sep. 19, 2014 for U.S. Appl. No. 13/685,909.
Office action dated Nov. 19, 2012 for U.S. Appl. No. 13/096,602.
Office action dated Dec. 29, 2014 for U.S. Appl. No. 13/685,909.
U.S. Appl. No. 14/625,366, filed Feb. 18, 2015.
Dictionary.com definition of fixed, accessed on Sep. 13, 2017, http://www.dictionary.com/browse/fixed accessed on Sep. 13, 2017, http://www.dictionary.com/browse/fixed.
European search report and opinion dated Feb. 17, 2017 for EP Application No. 140829202.
European search report with written opinion dated Jul. 12, 2016 for EP13851258.
Extended European search report and opinion dated Jul. 27, 2017 for EP Application No. 15733186.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
Merriam-webster definition of integral, accessed on Sep. 13, 2017, https://www.merriam-webster.com/dictionary/integral.
Notice of allowance dated Feb. 21, 2017 for U.S. Appl. No. 14/625,366.
Notice of allowance dated Feb. 23, 2016 for U.S. Appl. No. 15/081,595.
Notice of allowance dated Dec. 19, 2016 for U.S. Appl. No. 15/130,149.
Office action dated Jun. 1, 2017 for U.S. Appl. No. 15/442,382
Office action dated Jun. 2, 2017 for U.S. Appl. No. 13/665,160.
Office action dated Aug. 24, 2017 for U.S. Appl. No. 14/958,803.
Office Action dated Sep. 22, 2017 for U.S. Appl. No. 13/665,160.
Office Action dated Sep. 26, 2017 for U.S. Appl. No. 13/685,909.
Office Action dated Oct. 5, 2017 for U.S. Appl. No. 14/958,818.
Office Action dated Nov. 22, 2017 for U.S. Appl. No. 15/130,764.
Office Action dated Nov. 28, 2017 for U.S. Appl. No. 15/442,382.
PCT/US2017/059286 International Search Report and Written Opinion dated Mar. 6, 2018.
"Notice of Allowance dated Jun. 15, 2018 for U.S. Appl. No. 13/665,160."
"Notice of Allowance dated Jun. 20, 2018 for U.S. Appl. No. 15/130,764."
"Notice of Allowance dated Aug. 9, 2018 for U.S. Appl. No. 14/851,059."
"Office action dated Jun. 6, 2018 for U.S. Appl. No. 15/201,088."
"U.S. Appl. No. 14/958,803 Notice of Allowance dated Apr. 4, 2018".
U.S. Appl. No. 14/958,803 Notice of Allowance dated May 11, 2018.
"U.S. Appl. No. 13/685,909 Office Action dated May 1, 2018".

* cited by examiner

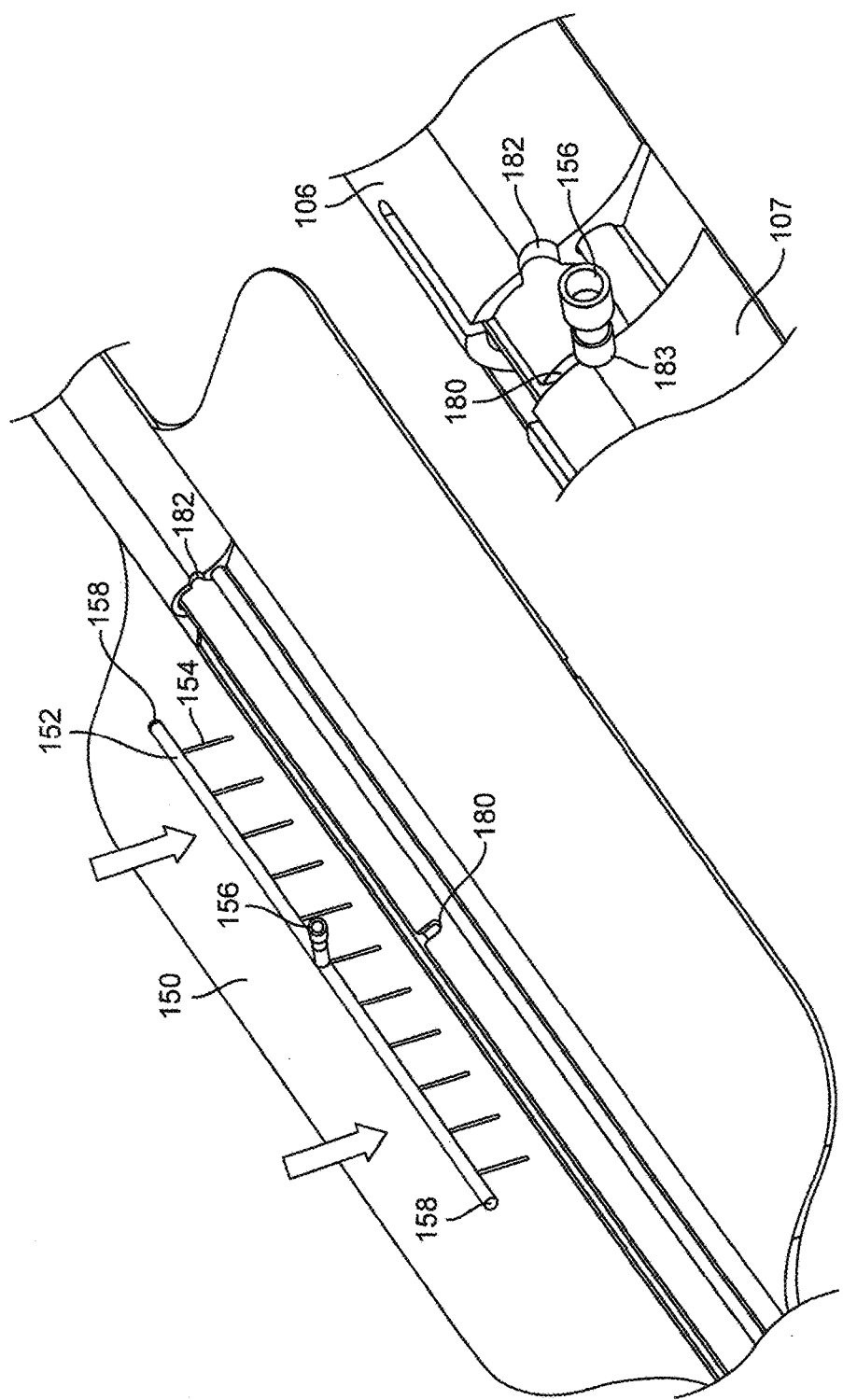

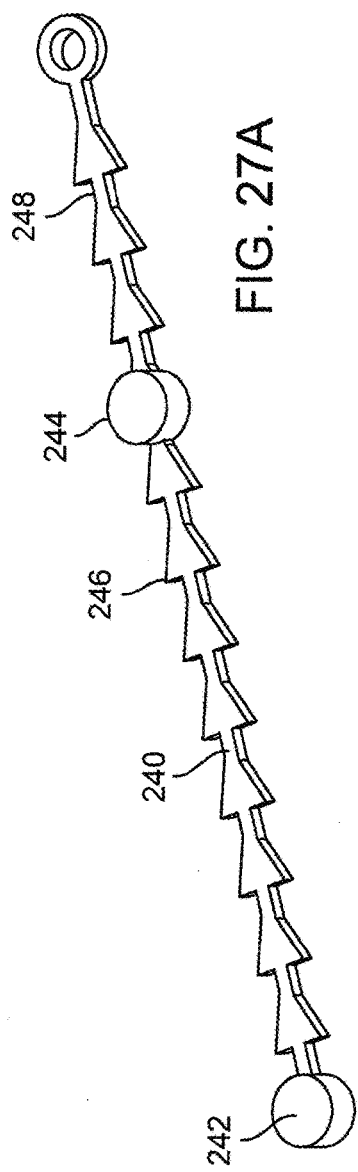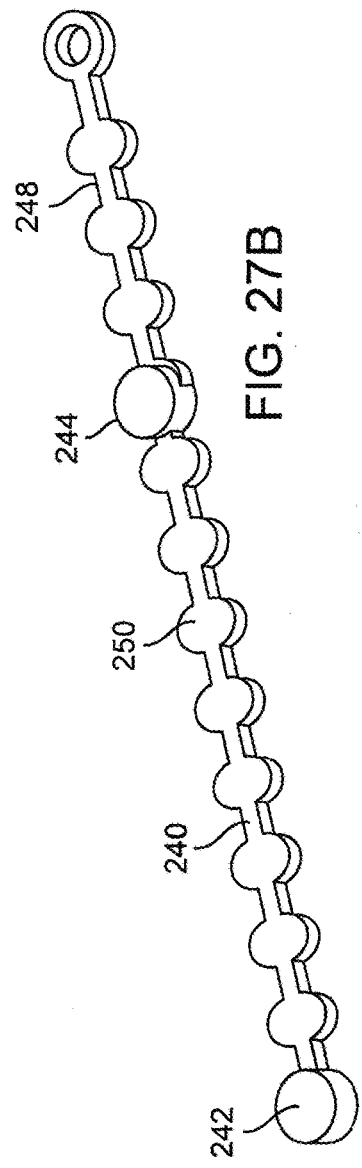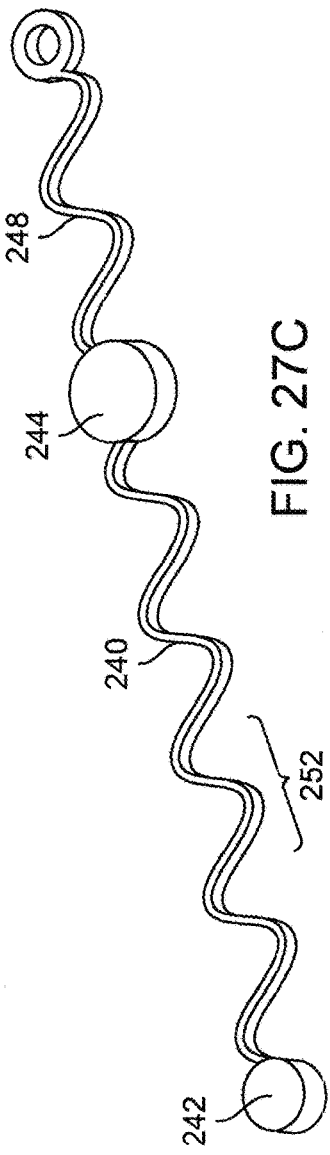

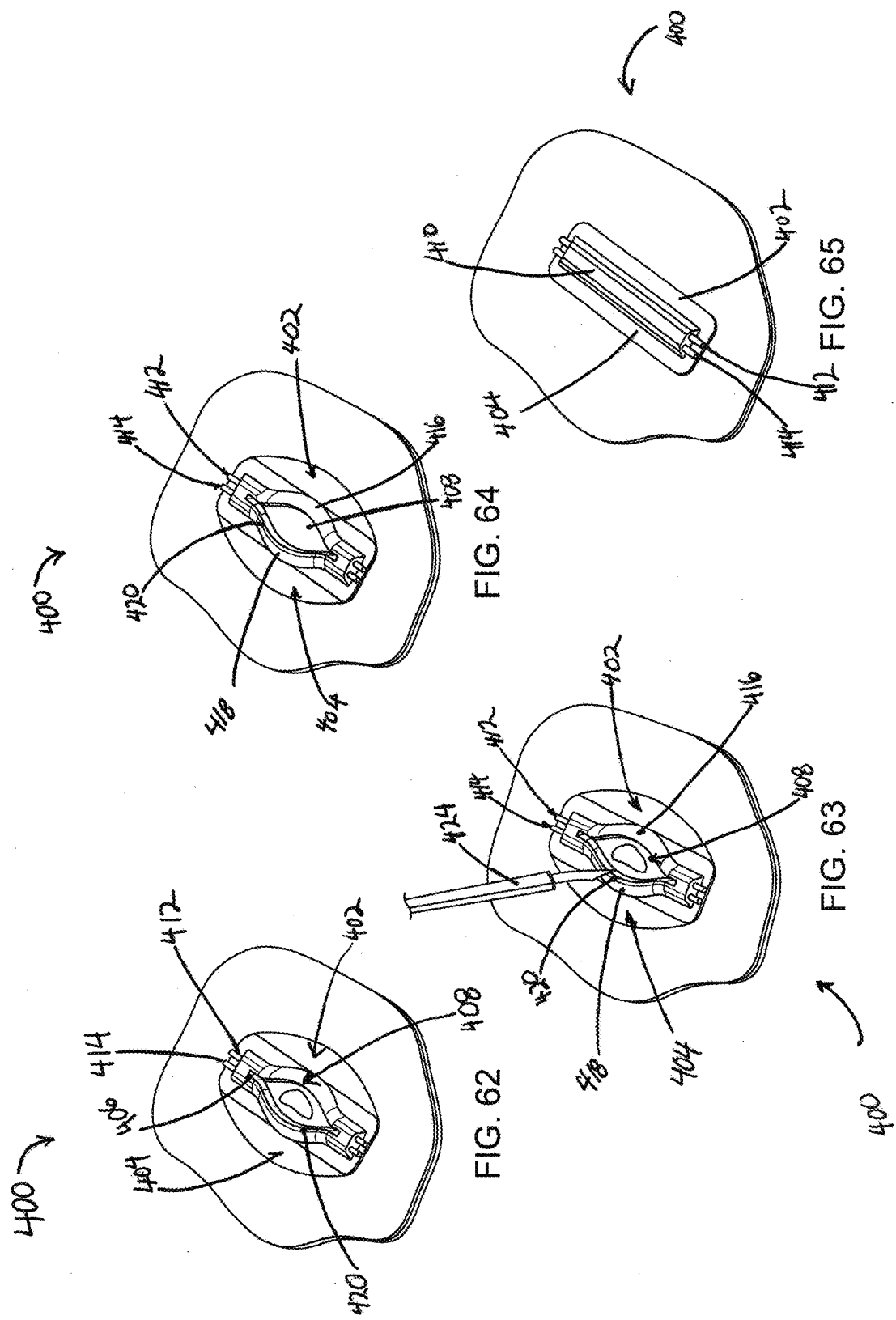

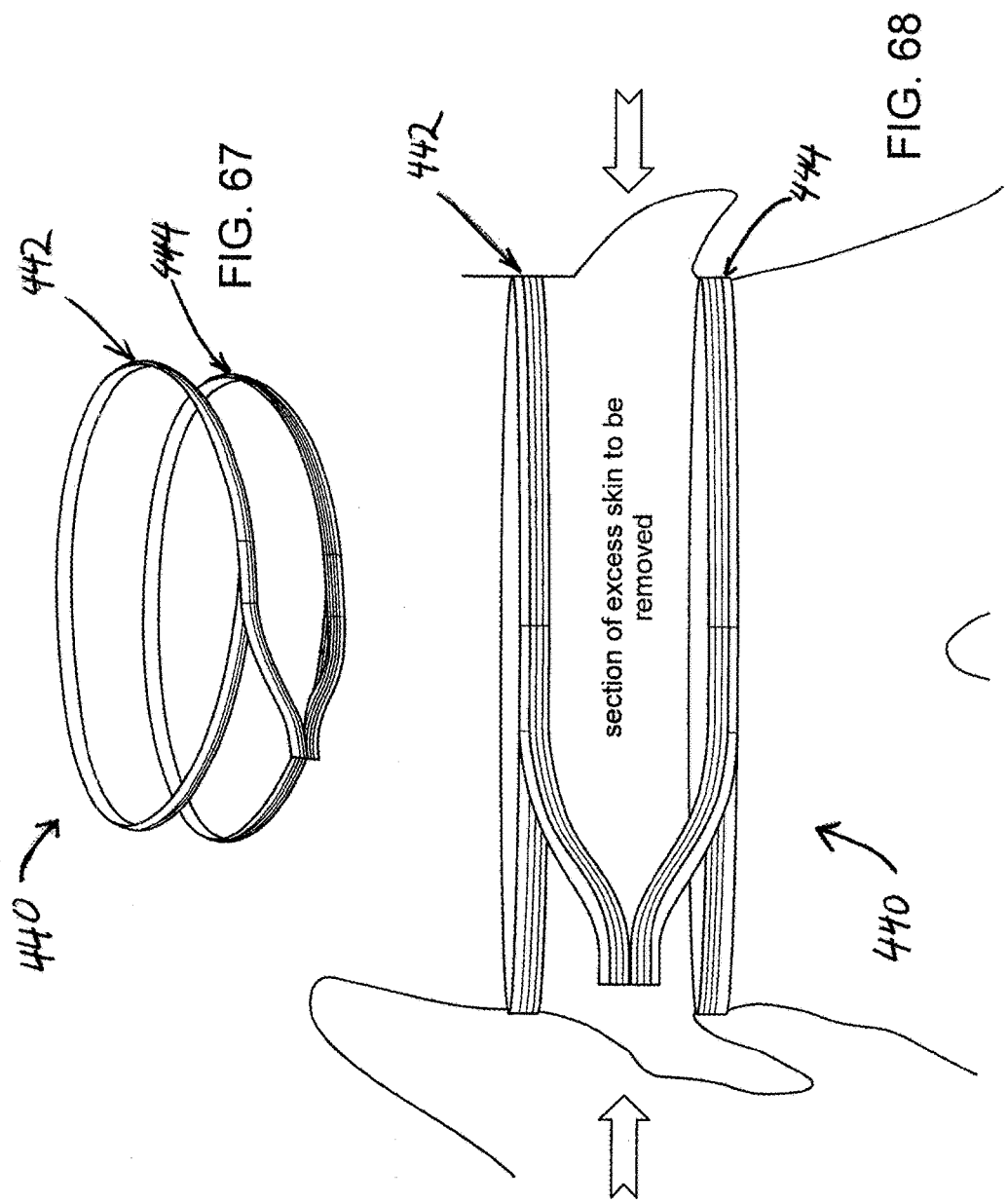

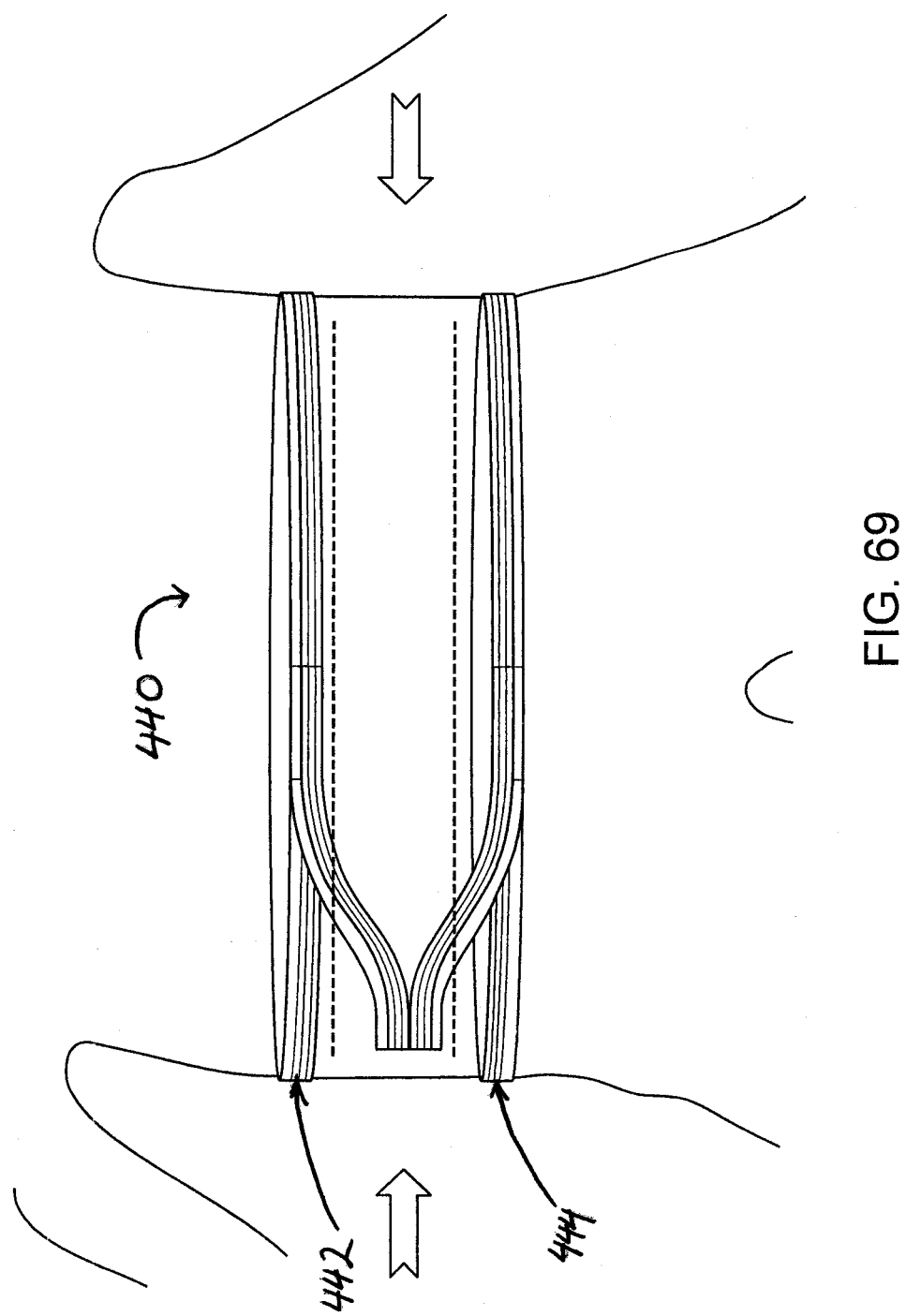

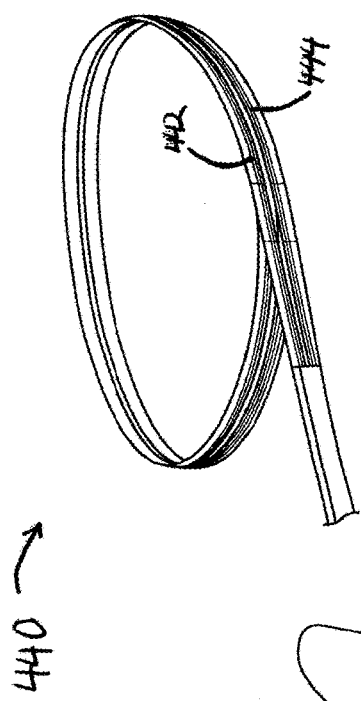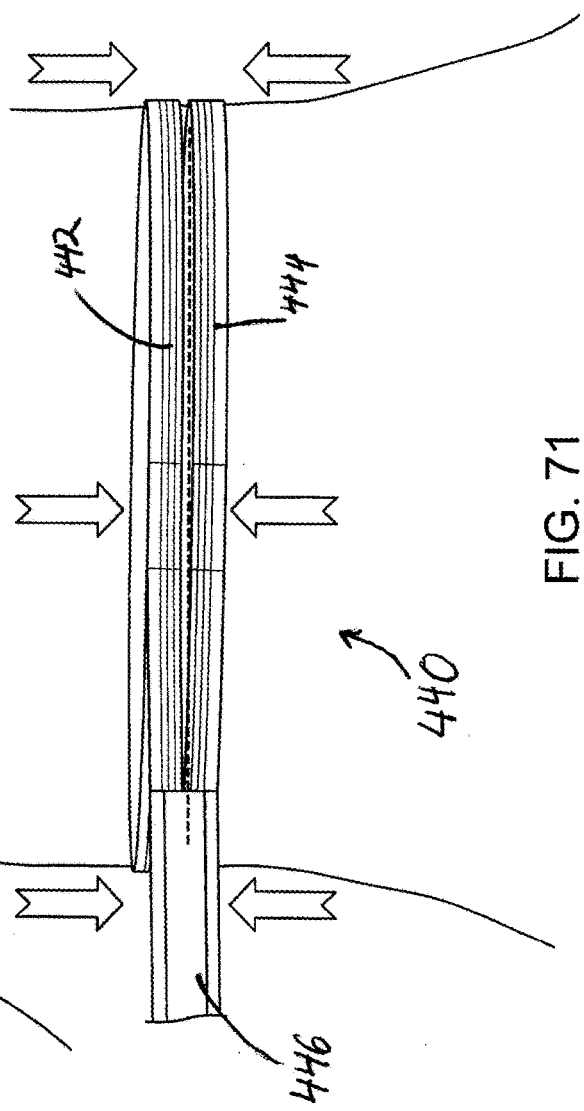

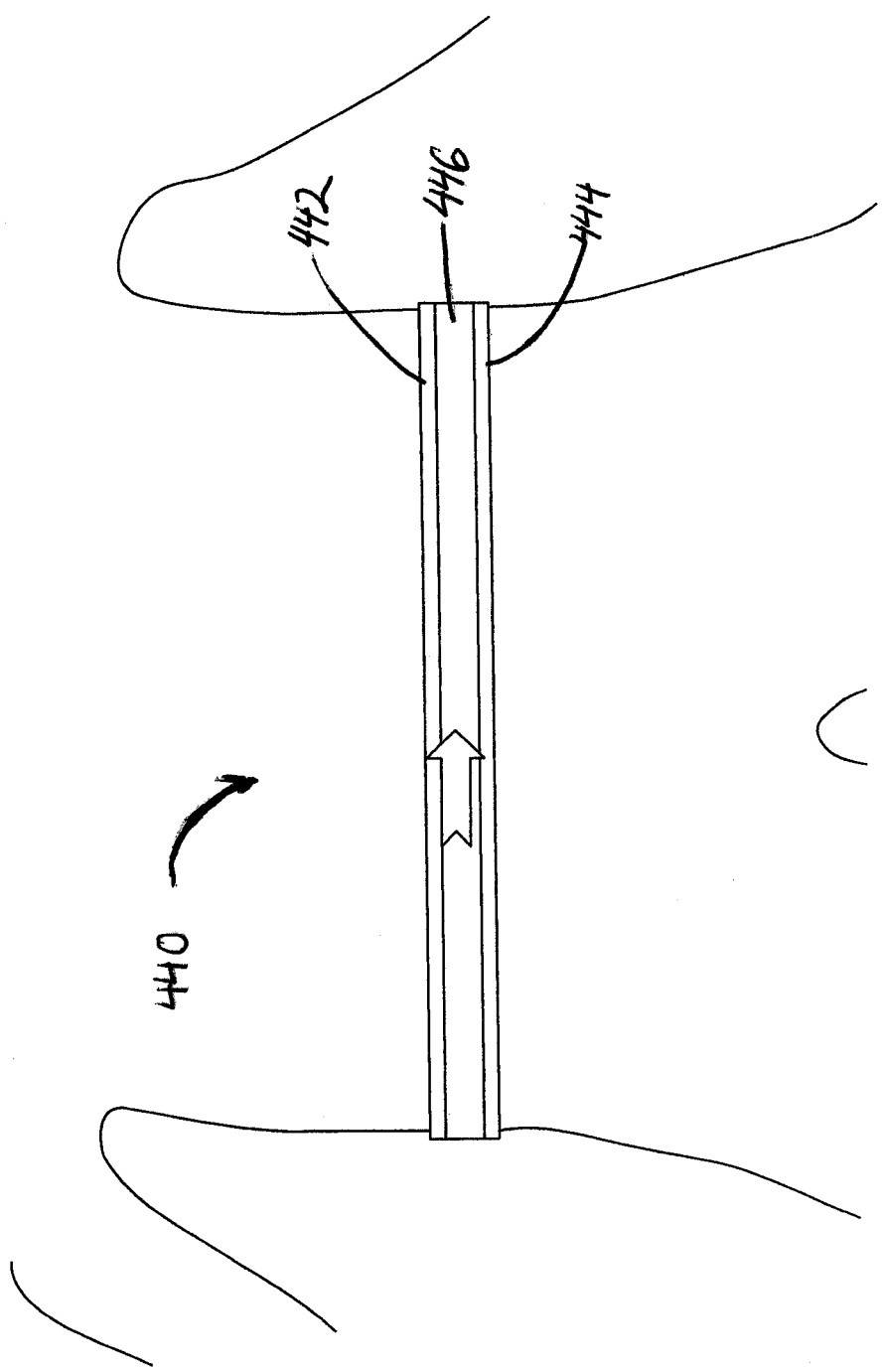

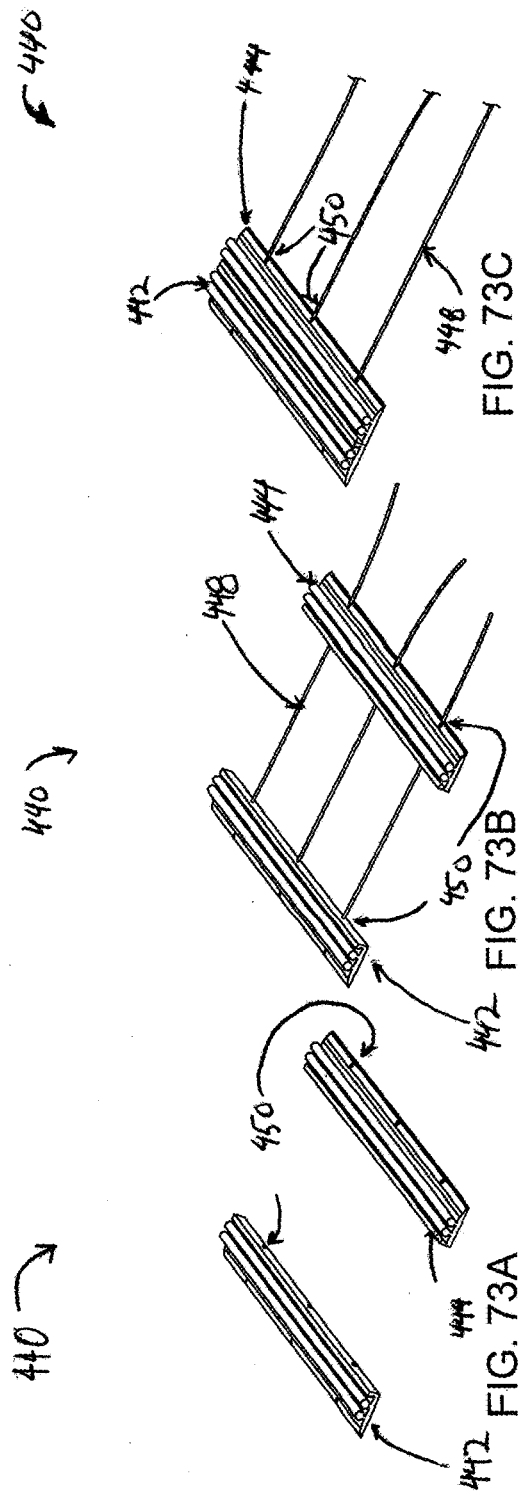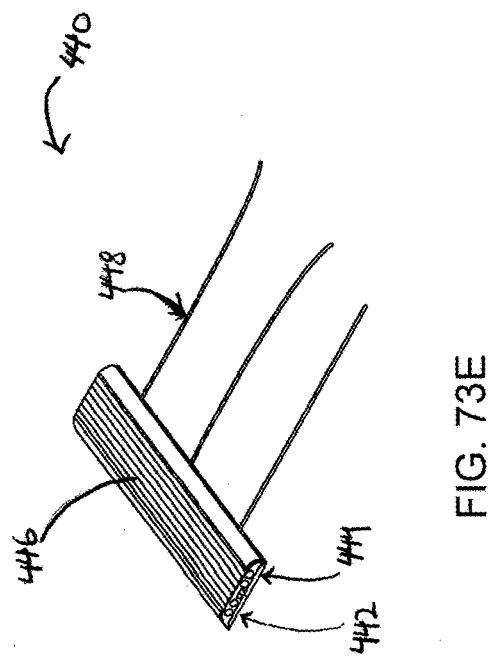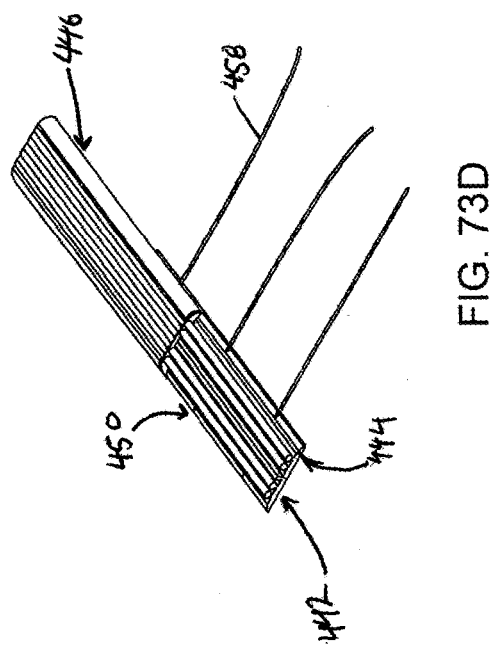

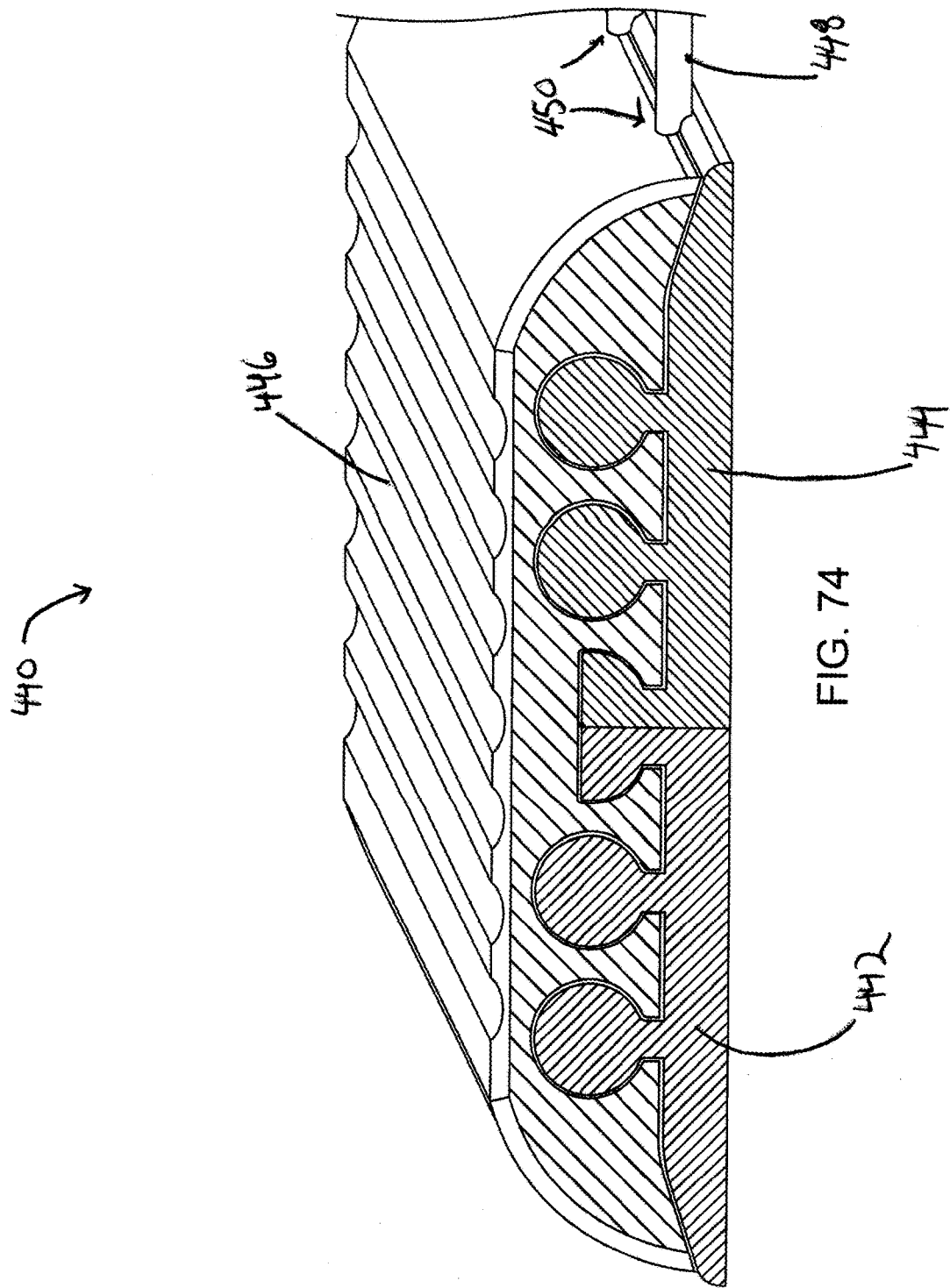

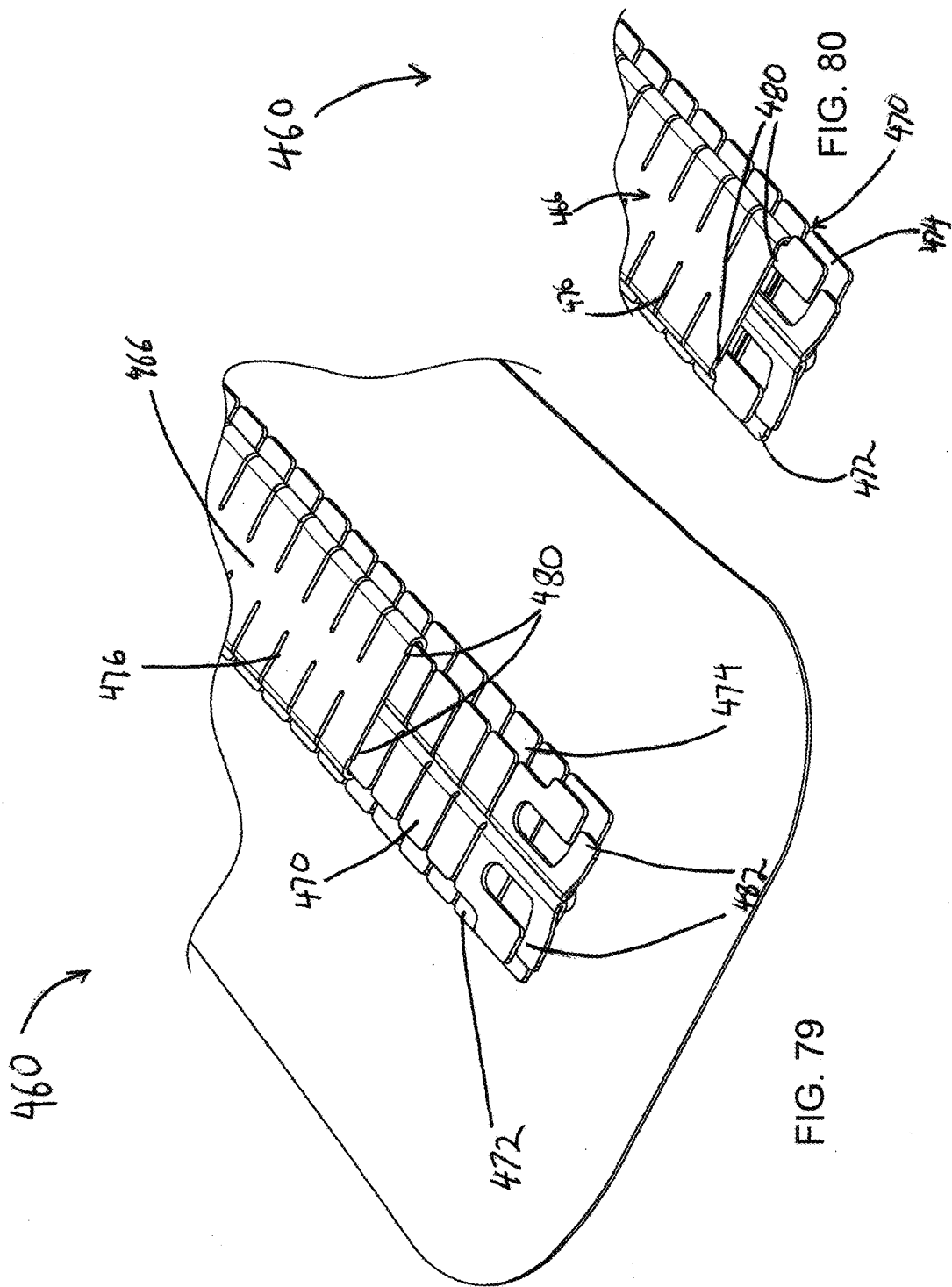

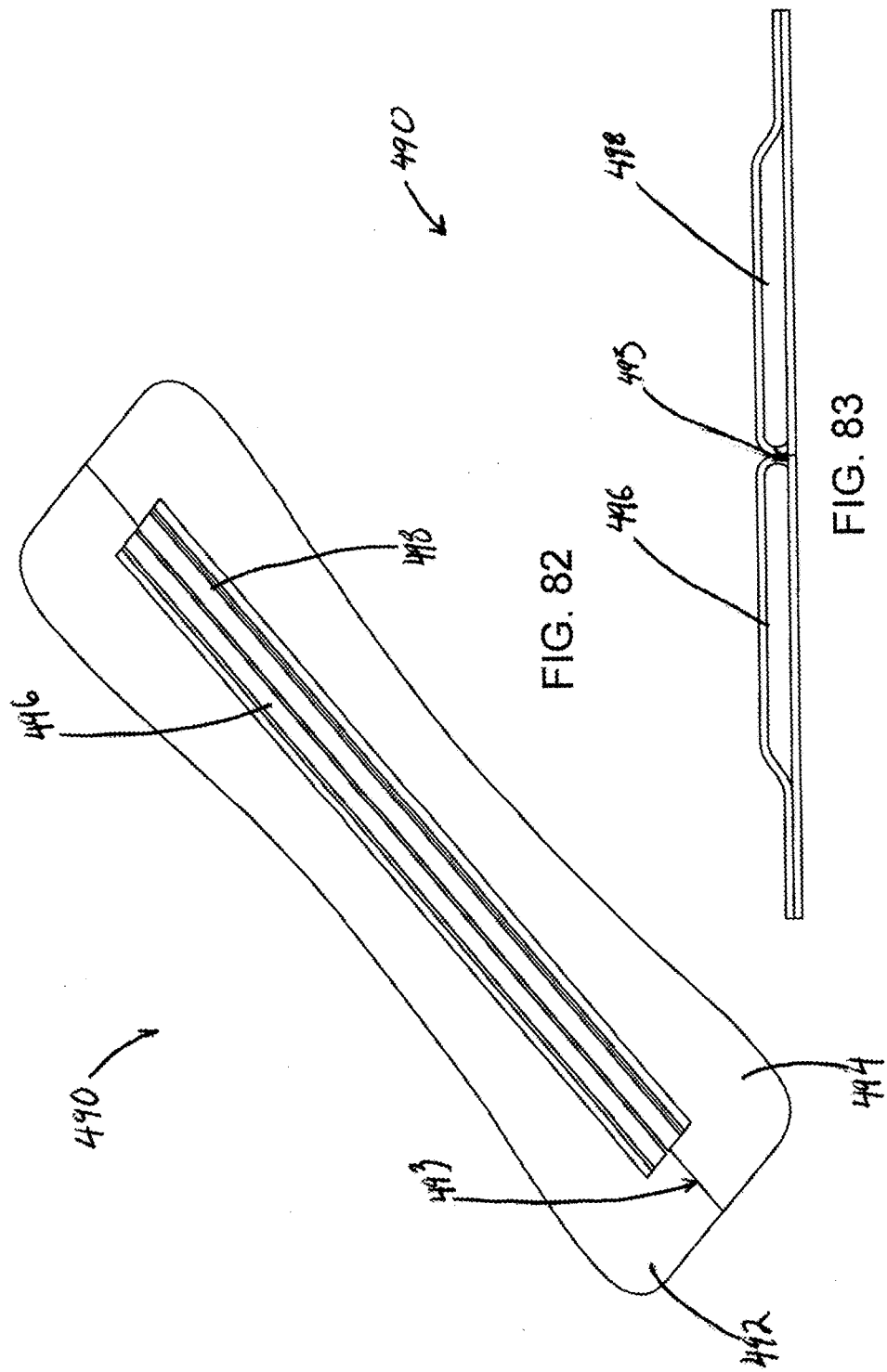

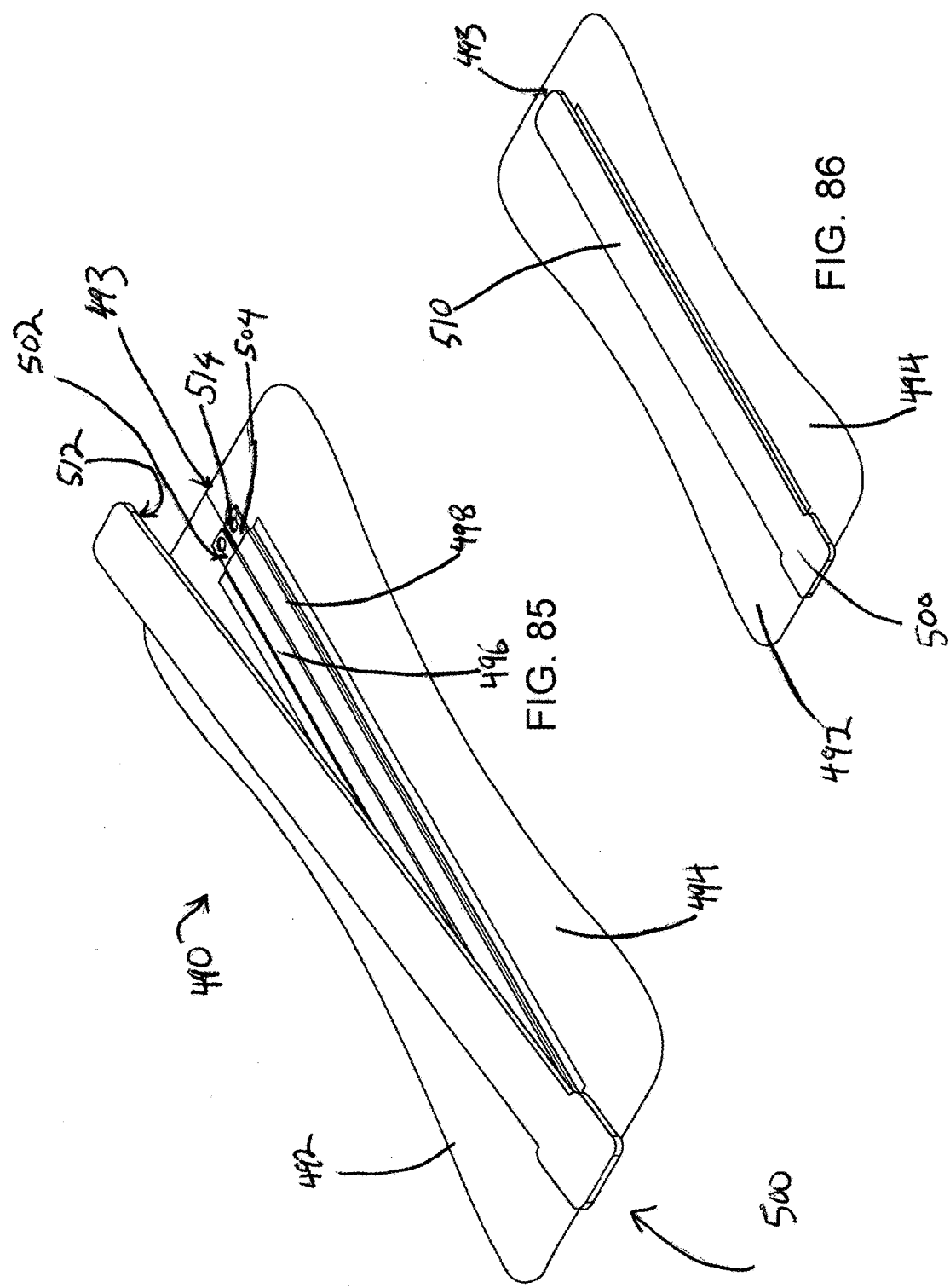

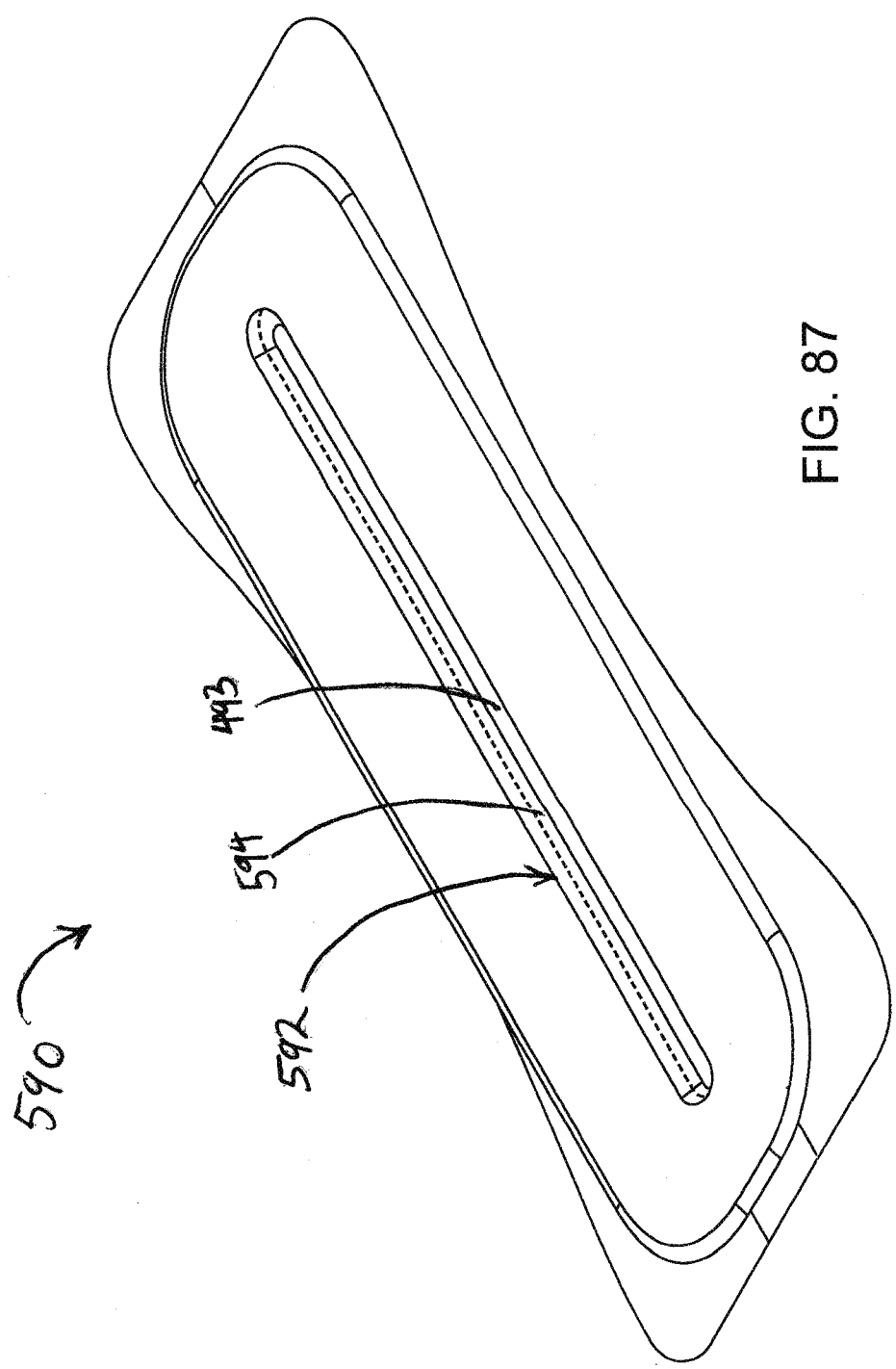

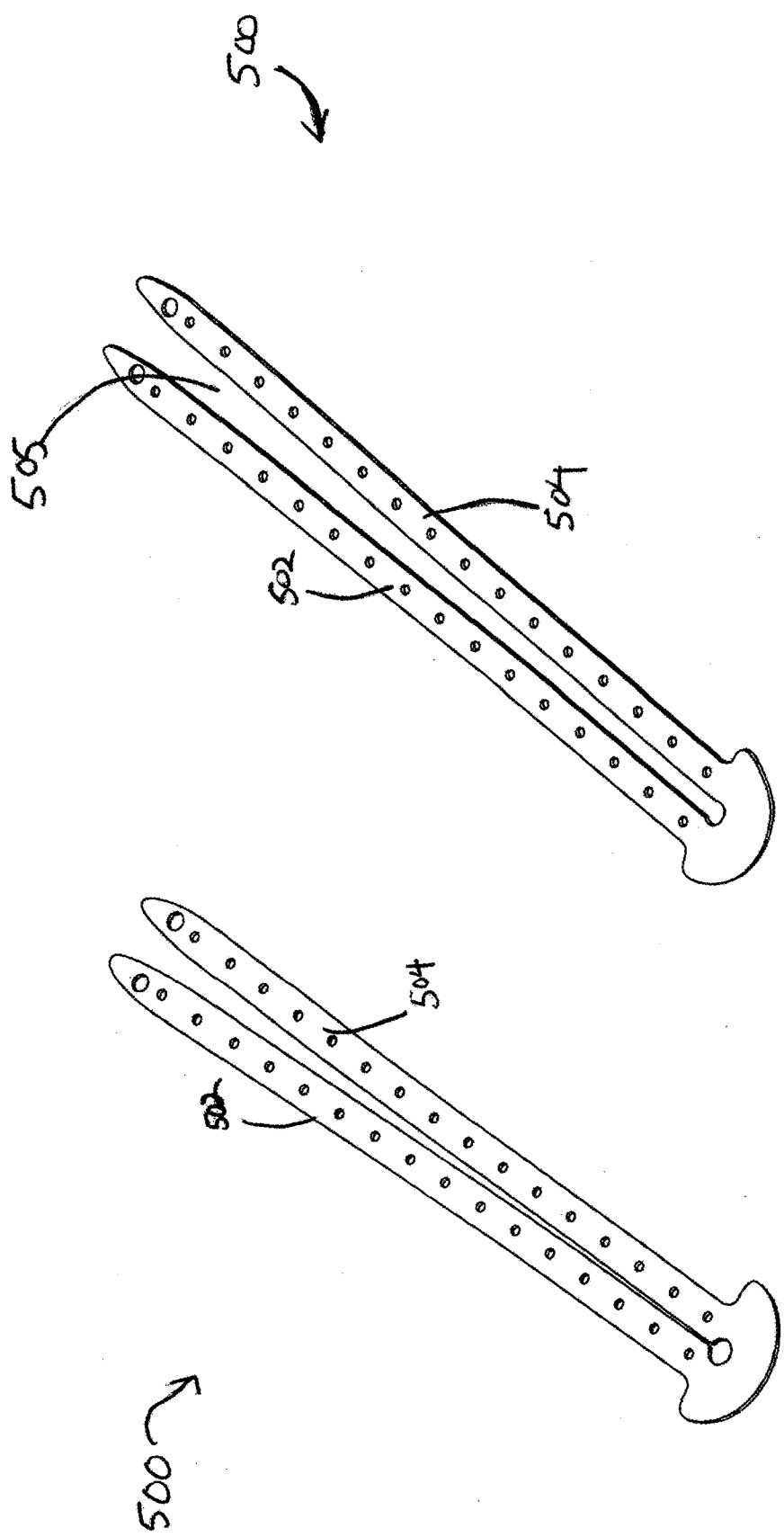

RAPID CLOSING SURGICAL CLOSURE DEVICE

RELATED APPLICATIONS

This application is a continuation-in-part of U.S. patent application Ser. No. 13/414,176, filed Mar. 7, 2012, which is a continuation of PCT Application No. PCT/US2010/000430, filed May 3, 2010, which claims the benefit of Provisional Application 61/243,423, filed Sep. 17, 2009, the contents of which are incorporated herein by reference in their entirety.

BACKGROUND OF THE INVENTION

1. Field of the Invention

The present invention relates generally to surgical closure devices and, more particularly, to devices for rapidly closing a surgical incision with precise apposition of the sides of the incision. Additional features provide for injection of anesthetics or other drugs into or around the surgical site, drainage of the surgical site, cutting guides for specially shaped incisions and controllable compression of the apposed edges for improved healing.

2. Description of the Background Art

A number of previous inventors have proposed surgical closure devices that utilize slide fasteners and the like for rapid closure of surgical incisions or wounds. Examples of these devices include:

De Muth U.S. Pat. No. 2,012,755 Surgical Dressing
Howell U.S. Pat. No. 3,516,409 Slide fastener employing skin closure appliances and techniques
Haverstock U.S. Pat. No. 3,863,640 Bandage construction
Haverstock U.S. Pat. No. 3,933,158 Skin closure means
Haverstock U.S. Pat. No. 4,114,624 Skin closure means
Sheehan U.S. Pat. No. 4,535,772 Skin closure device
Fukuda U.S. Pat. No. 4,676,245 Interlocking surgical staple assembly
Kaessmann U.S. Pat. No. 4,881,546 Wound-closure device and method
Will U.S. Pat. No. 4,905,694 Intracorporeal temporary wound closure
An Haack U.S. Pat. No. 5,377,695 Wound-closing strip One slide fastener-type surgical closure device that has been commercialized is the ETHIZIP Temporary Abdominal Wound Closure Device from the Ethicon division of Johnson & Johnson. According to the instructions for use, the ETHIZIP device must first be sewn into the fascia and peritoneum with sutures before the metal slider is used to join the two sides of the slide fastener together, therefore it is not suitable as a rapid closure device. The ETHIZIP device is also not configured to be placed on the skin or other tissue prior to making an incision. Currently, surgical staples are usually employed when rapid closure of a surgical incision is desired. Although they are fast and convenient for the surgeon, surgical staples do not provide precise apposition of the sides of the incision and the compression is excessive, and unevenly distributed, which encourages scar formation. The staples themselves create local ischemia that causes extra scarring, in addition to the scar from the incision.

What is needed therefore, is a surgical closure device for rapidly closing a surgical incision with precise apposition of the sides of the incision and with controllable, uniform compression of the apposed edges for improved healing.

In addition, it is desirable to provide for injection of drugs, for example anesthetics for pain control, into the wound or the surrounding tissue over a period of hours, days or longer.

SUMMARY OF THE INVENTION

In keeping with the foregoing discussion, the present invention takes the form of a surgical closure device or wound closure device that utilizes a slide fastener for rapid closure of a surgical incision or wound. In one particularly preferred method of use, the surgical closure device is adhered to the patient's skin prior to making an incision and is subsequently used for closing the incision.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 11 shows insertion of a drug injection manifold into the surgical closure device of FIG. 9.

FIG. 12 shows the surgical closure device of FIG. 9 with the dual binders closing around the drug injection manifold.

FIGS. 27A, 27B and 27C show various configurations of tension members for use with the surgical closure device of FIG. 26.

FIG. 62-65 illustrate a surgical closure device for making and closing a shaped incision in the patient's skin.

FIGS. 67-72 illustrate an embodiment of a surgical closure device configured for closing a large incision in a patient's skin.

FIGS. 73A-73E illustrate a surgical closure device with alignment cords to assist in approximating the first rail and the second rail.

FIG. 74 is an enlarged view of the surgical closure device of FIGS. 73A-73E in a closed position.

FIGS. 75-80 illustrate a low-profile surgical closure device using a C-shaped binder.

FIGS. 81-86 illustrate another low-profile surgical closure device using a fork-shaped binder.

FIG. 87 illustrates an incision template for use with the surgical closure device of FIGS. 81-86.

FIG. 88 illustrates a fork-shaped binder with an inwardly convex curvature to the tines.

FIG. 89 illustrates a fork-shaped binder for holding a surgical closure device in a partially open position.

FIGS. 111A-110H illustrate a method of using the closure device of FIGS. 110A-110F.

DETAILED DESCRIPTION OF THE INVENTION

Figure 1:
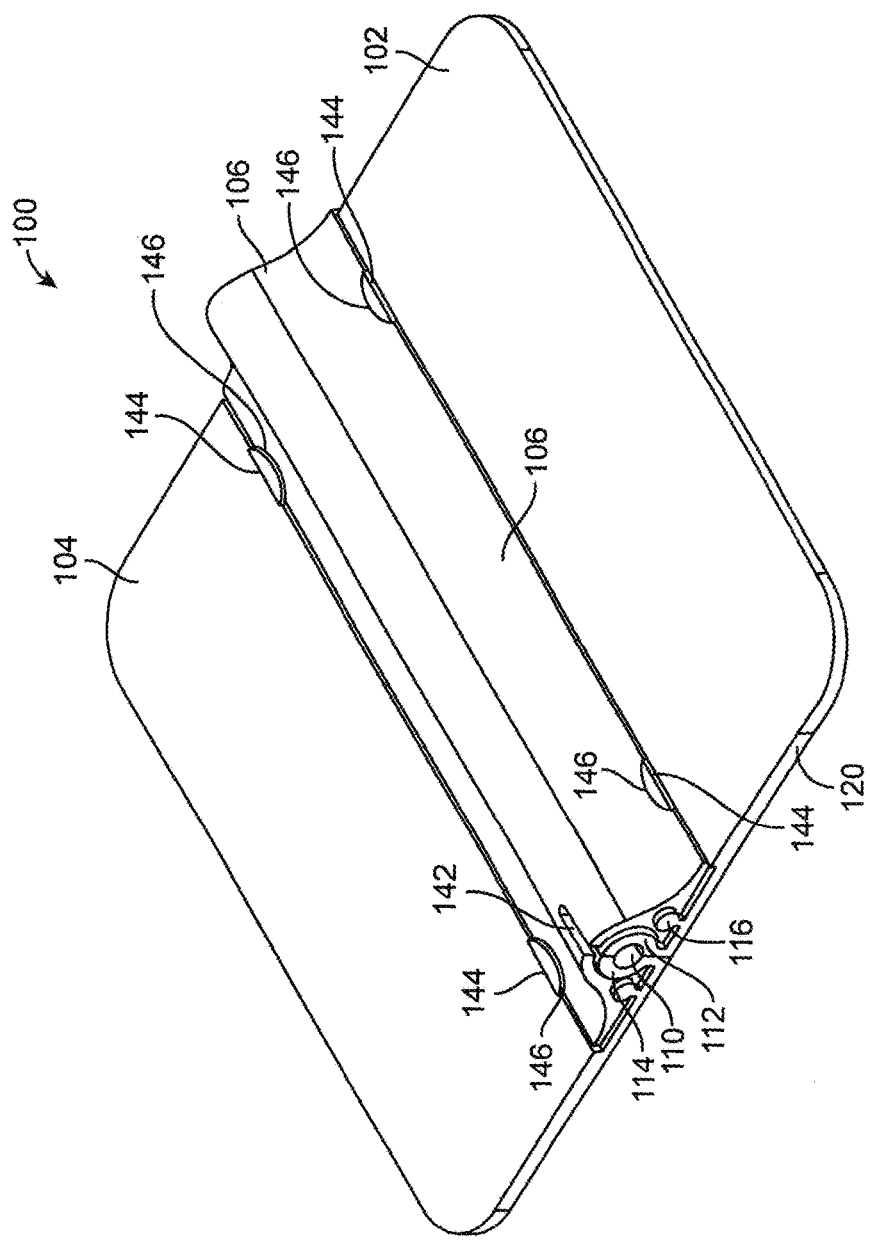
FIG. 1 is a perspective drawing of the surgical closure device being applied to a patient's skin.

FIG. 1 is a perspective drawing of a surgical closure device 100 according to the present invention being applied to a patient's skin. Generally, the surgical closure device 100 includes a first adhesion patch 102, a second adhesion patch 104 and a binder 106 that is configured to hold the first and second adhesion patch 102, 104 together as shown. The first adhesion patch 102 and the second adhesion patch 104 are generally planar and are preferably constructed of a flexible elastomeric material that is biocompatible for skin contact. Suitable materials include, but are not limited to, natural rubber, polyurethane, silicone, etc. Optionally, the first and second adhesion patch 102, 104 may be reinforced with fibers, a mesh or a woven or knitted textile fabric.

Optionally, the first and second adhesion patch 102, 104 may have pores, slits, mesh or openings through them to ventilate the patient's skin below the closure device 100. The skin contacting surfaces of the first adhesion patch 102 and the second adhesion patch 104 have a medically acceptable skin adhesive 120 applied to them, preferably a contact adhesive that prior to use would be covered with a peel-away protective film. Alternatively or in addition, the first adhesion patch 102 and the second adhesion patch 104 may be glued with an adhesive applied to the device and/or the skin (e.g. a medically acceptable cyanoacrylate adhesive), sutured or stapled to the skin.

Figure 6:
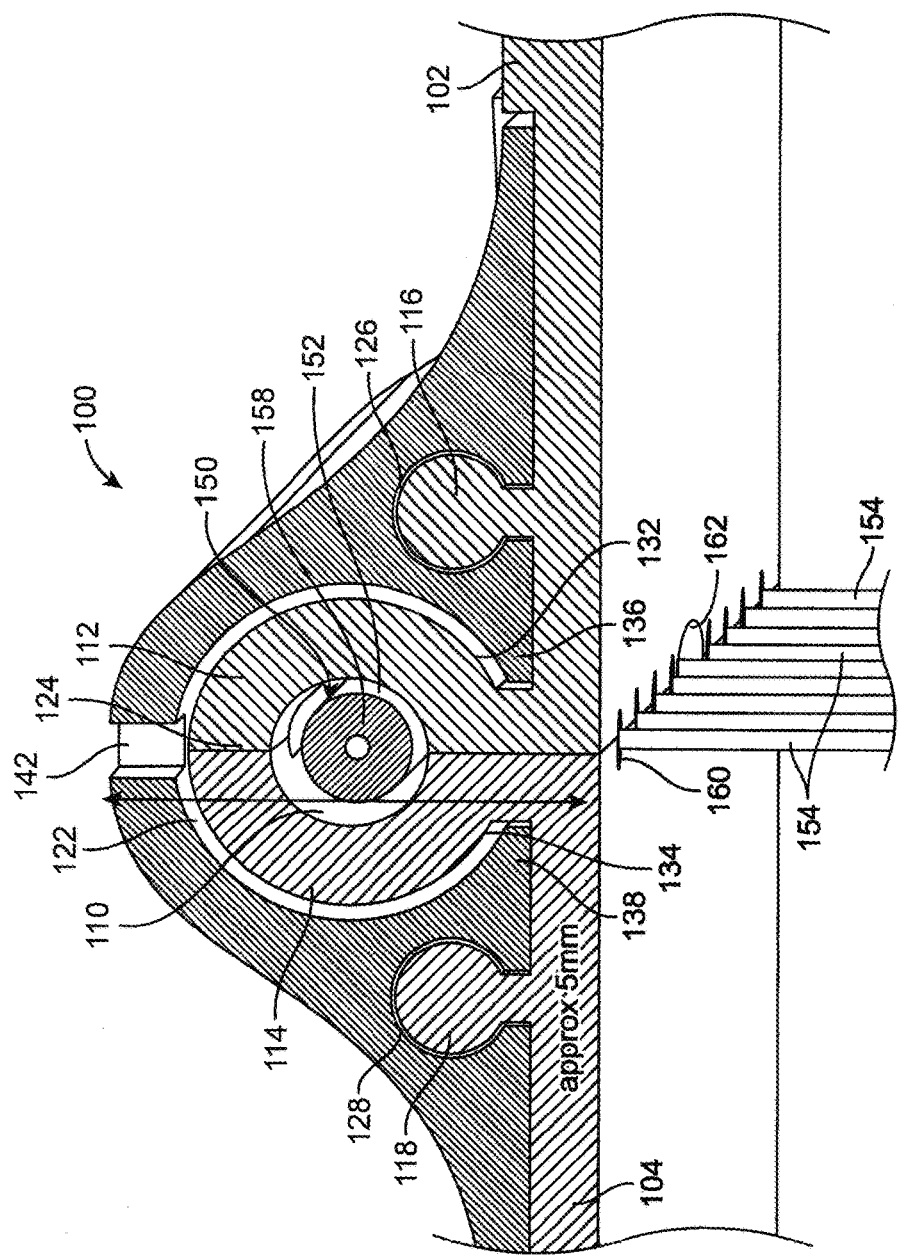
FIG. 6 is an end view showing the cross-sectional details of the surgical closure device.

In use, the first adhesion patch 102 and the second adhesion patch 104 are arranged side-by-side with one another and, as shown in detail in FIG. 6, the adjacent edges are provided with a first rail 112 and a second rail 114, respectively. The binder 106 includes a main channel 122 that is sized to it over the first rail 112 and the second rail 114 with a snug sliding fit. Preferably, the geometry of the first and second rail 112, 114 will provide a first and second undercut 132, 134 for the inside edges 136, 138 of the main channel 122 to interlock with. This can be accomplished with many different geometries such as the example shown where the first rail 112 and the second rail 114 are configured as half cylinders that fit together to form a complete cylinder when joined together along a central parting line 124. Optionally, the first adhesion patch 102 and the second adhesion patch 104 may also include a first supplemental rail 116 and a second supplemental rail 118, respectively, and the binder may include a first supplemental channel 126 and a second supplemental channel 128 that fit over the rails 116, 118 to provide additional attachment strength and stability to the surgical closure device 100 when in a closed position. Preferably, the first supplemental rail 116 and the second supplemental rail 118 also provide undercuts for the first supplemental channel 126 and the second supplemental channel 128 to interlock with. Optionally, the first supplemental rail 116 and the second supplemental rail 118 may also be configured as cylinders, as in the example shown. The rails 112, 116, 114, 118 are preferably molded of a polymer material, for example by casting, injection molding or extrusion, and may be formed integrally with the first and second adhesion patch 102, 104, respectively. Alternatively, the rails 112, 116, 114, 118 may be overmolded with or assembled onto the first and second adhesion patch 102, 104. Optionally, one or more of the rails 112, 116, 114, 118 may be reinforced, for example with reinforcing wires that run longitudinally through the rails.

The binder 106 will preferably be molded of a polymer material, for example by casting, injection molding or extrusion. Suitable materials for making the binder 106 include, but are not limited to, polyurethane, nylon, polypropylene, polycarbonate, etc. The binder 106 will have enough circumferential strength in the wall of the main channel 122 to hold the first rail 112 and the second rail 114 firmly together when the surgical closure device 100 is in the closed position. Optionally, the binder 106 may be reinforced longitudinally or circumferentially around one or more of the channels. Preferably, the polymer material will have a low enough coefficient of friction that the binder 106 will slide easily over the rails 112, 114, 116, 118.

The overall dimensions of the surgical closure device 100 will depend on the surgical application, but, in general, the first and second adhesion patch 102, 104 should have a length slightly longer than the length of the desired incision. Preferably, the binder 106 will also have a length slightly longer than the length of the desired incision. This is desirable because it provides a very secure closure along the entire length of the incision, particularly as compared to prior art devices that only use a small slider device to join the sides of a slide fastener together. FIG. 1 shows an embodiment where the binder 106 is approximately the same length as the first and second adhesion patch 102, 104, which is one optional configuration.

The surgical closure device 100 is adhered onto the patient's skin at the desired incision site with the closure device 100 in a closed position prior to making as incision, as shown in FIG. 1, which assures that the sides of the incision will be precisely apposed or aligned with one another when the closure device 100 is closed again after the surgery. The binder 106 and the first and second adhesion patch 102, 104 may be constructed with corresponding notches 146 and detents 144 to further assure that the sides of the incision will be precisely apposed when the closure device 100 is reclosed. Alternatively or in addition, similar notches and detents may be provided between the first and second adhesion patch 102, 104 to assure that they align correctly whenever the closure device 100 is closed.

Figure 2:
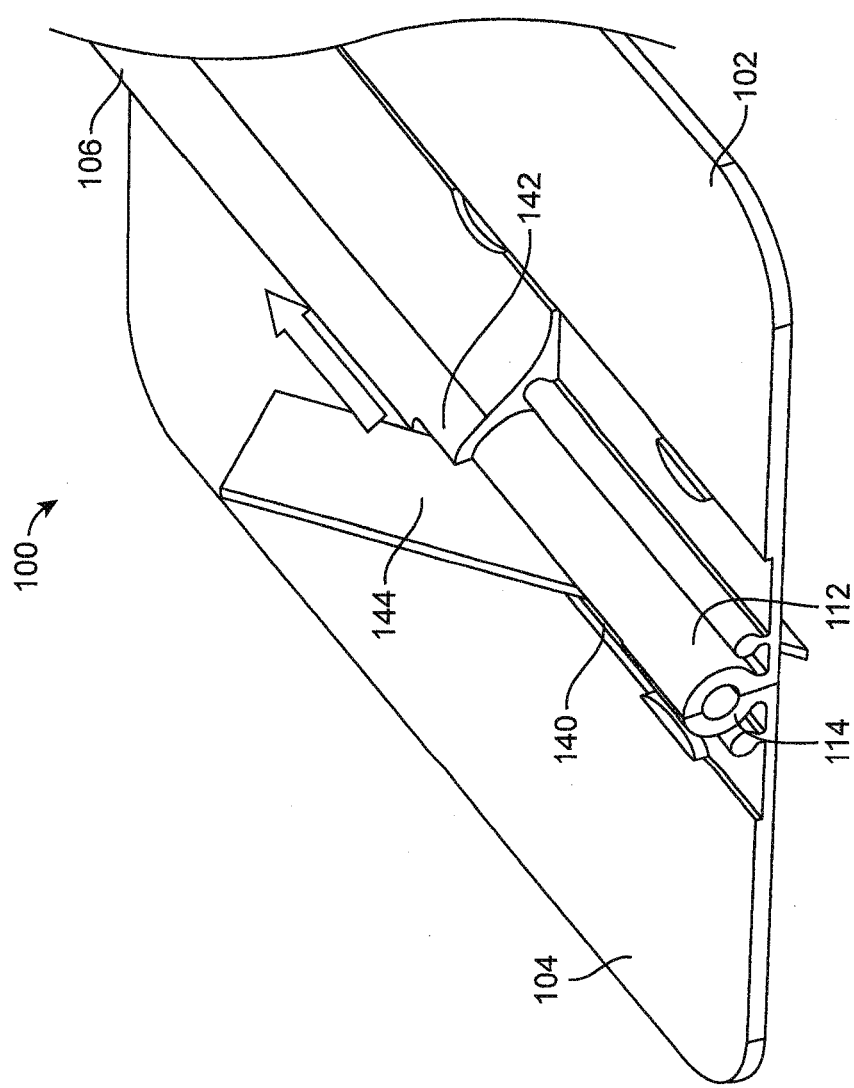
FIG. 2 shows the surgical closure device being used as a guide for making an incision in the patient's skin.
Figure 3:
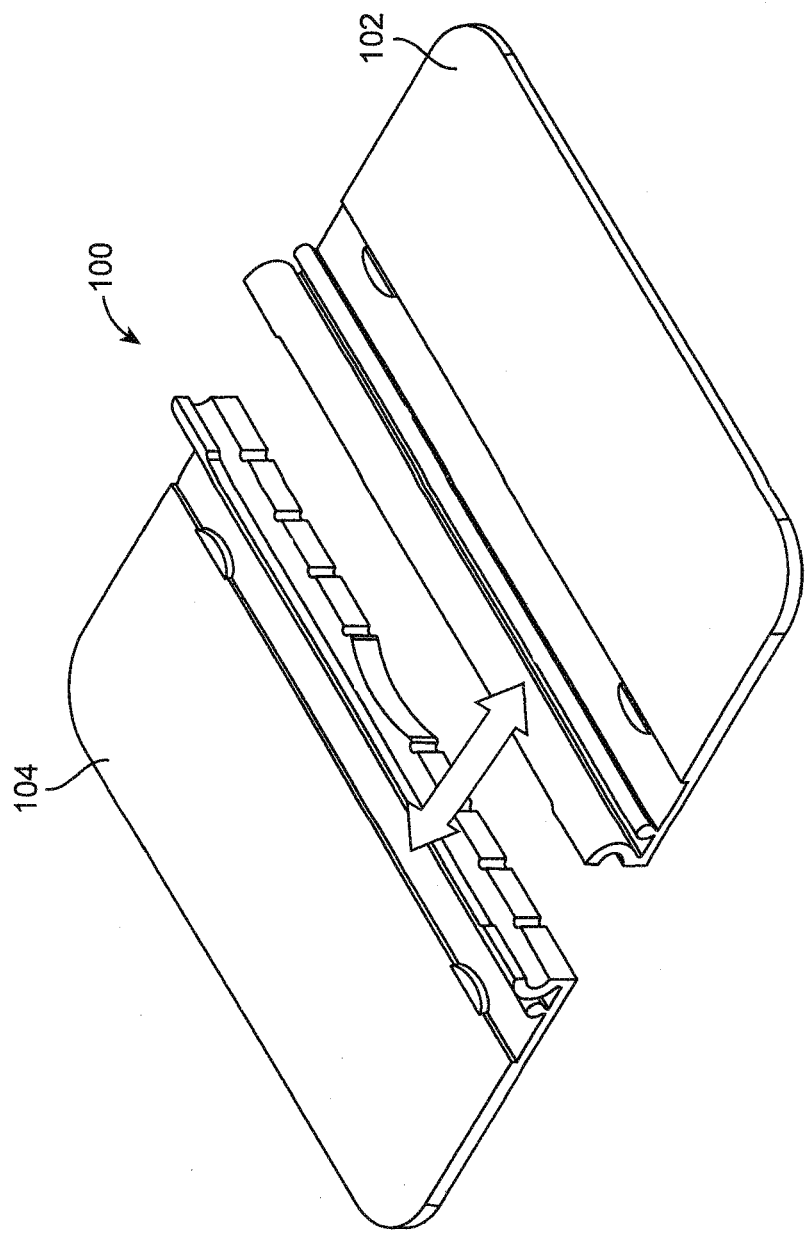
FIG. 3 shows the surgical closure device in an open position for access to the surgical incision.

FIG. 2 shows the surgical closure device 100 being used as a guide for making an incision in the patient's skin. Alternatively or in addition, the surgical closure device 100 being used as a guide for opening and/or treating the incision with coagulation or electrocautery. Optionally, the first rail 112 and/or the second rail 114 is constructed with a guide slot 140 along the parting line 124 for accepting a scalpel blade 144 or the like for making a skin incision. The length of the guide slot 140 can serve as an indication of the appropriate length of the incision for the closure device 100 that is being used. Optionally, the binder 106 may be constructed with a slot or notch 142 on one or both ends that aligns the scalpel blade 144 with the guide slot 140 between the rails 112, 114 for making the incision. The skin incision is made simultaneously as the binder 106 is being slid off of the rails 112, 114 with the notch 142 helping to hold the scalpel blade 144 at the correct depth and angle for making the skin incision. This has the additional advantage that the binder 106 prevents the incision from being pulled open by tension on the skin, which otherwise could cause the skin to tear or the incision to wander. Alternatively, a scalpel blade 144 can be mounted on a special blade holder device that is configured to slide along the rails 112, 114 with the scalpel blade 144 at the correct depth and angle for making the skin incision. Otherwise, the incision can be made after the binder 106 has been slid off of the rails 112, 114. FIG. 3 shows the surgical closure device 100 in an open position for access to the surgical incision. Once the initial skin incision is made, the fascia and muscular layers below the skin can be cut using known techniques to provide surgical access as appropriate for the surgical procedure being performed. The first adhesion patch 102 and the second adhesion patch 104 and the tissue below them can be separated using standard surgical retractors to open the incision for surgical access. The strength of the adhesive 120 and the flexibility of the first and second adhesion patch 102, 104 help to keep the device 100 adhered to the skin during these surgical manipulations.

After the surgical procedure has been completed and deeper tissues have been attached or closed using sutures, staples, glue or other appropriate means, the first adhesion patch 102 and the second adhesion patch 104 are brought closer together to approximate the sides of the incision. In many cases, it will be preferable to approximate the sides of the incision with precisely the same alignment and position as before the incision was made. Then, the first rail 12 and the second rail 114 are aligned and the binder 106 is slid over them to close the surgical closure device 100 with the sides of the incision precisely apposed to one another, similar to what is shown in FIG. 1.

The basic method of use can be summarized as follows: (1) adhere the surgical closure device 100 to the skin in the closed position; (2) remove the binder 6 and make the incision; (3) open the incision and perform the surgical procedure; and (4) slide the binder 6 onto the closure device 100 to close the incision. Variations of this method utilizing optional features of the surgical closure device 100 are described below. In some embodiments, the method of use may further comprise the delivery of drug(s) or other therapeutic agents through the surgical closure device 100 as described below.

Figure 4:
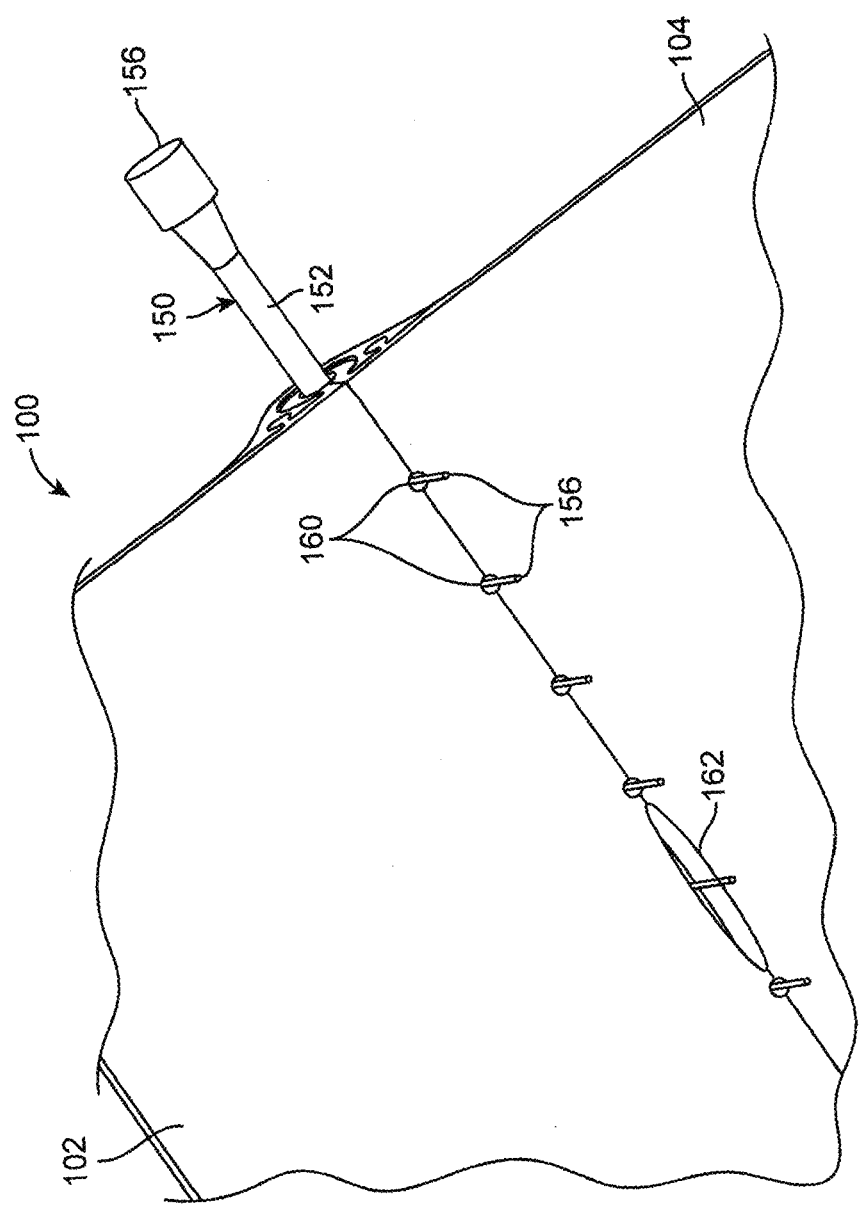
FIG. 4 is a perspective view from the underside of the surgical closure device showing insertion of a drug injection manifold.
Figure 5:
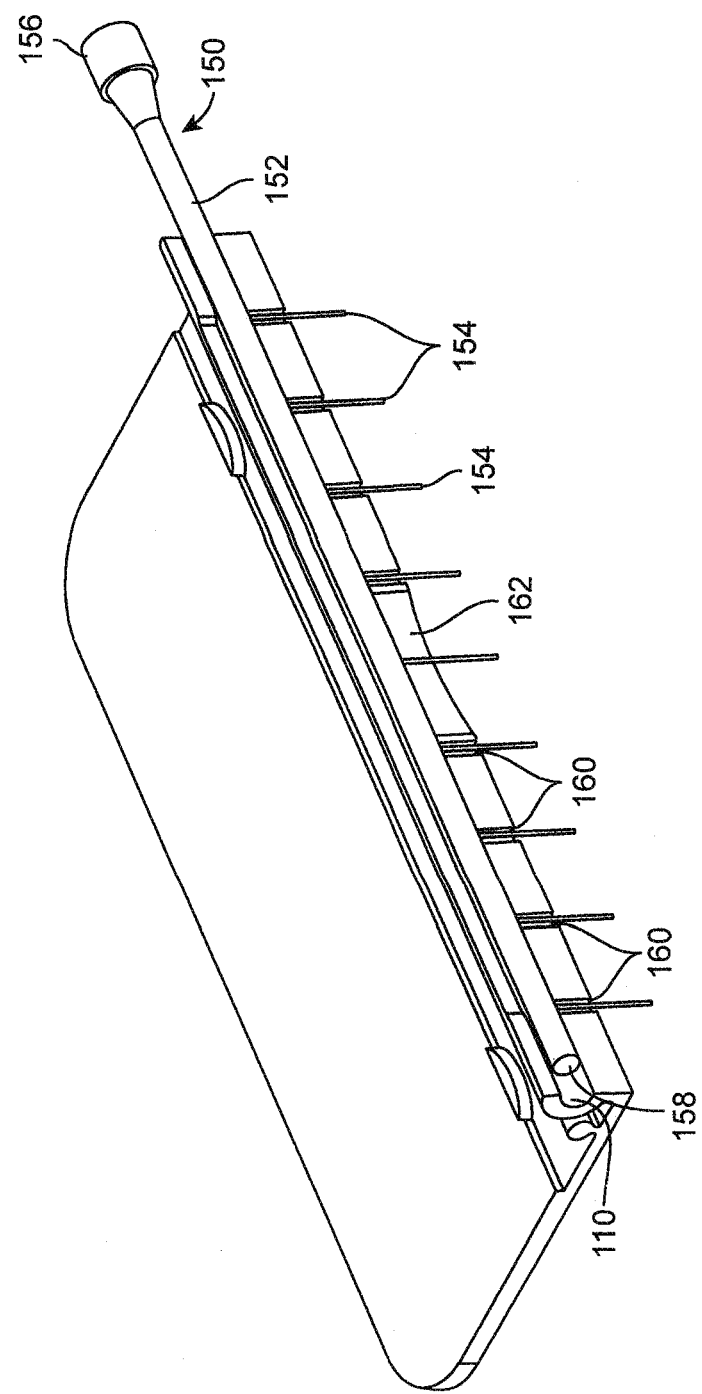
FIG. 5 is a perspective view from the upper side of the surgical closure device with the drug injection manifold in place. The binder and the first adhesion patch have been removed from the drawing to better show the drug injection manifold.

FIG. 4 is a perspective view from the underside of the surgical closure device 100 showing insertion of a drug injection manifold 150. FIG. 5 is a perspective view from the upper side of the surgical closure device 100 with the drug injection manifold 150 in place. The binder 106 and the first adhesion patch 102 have been removed from the drawing to better show the drug injection manifold 150. The drug injection manifold 150 is an important optional feature of the surgical closure device 100, which can be used in pain control, prevention of infection, and reduction of scarring and keloid formation. The drug injection manifold 150 has a main tube 152 with a proximal connector 156, such as a Luer fitting, and a closed distal end 158. At least one, and preferably several, drug injection needles 154 connect to the main tube 152 at a right angle. The hollow drug injection needles 154 may have blunt or sharp tips, depending how the drug injection manifold 150 is to be used. The main tube 152 and the drug injection needles 154 may be made from a metal, such as stainless steel, a flexible NiTi alloy or a polymer or a combination thereof. Microneedles can be fabricated using MEMS technology or other microfabrication techniques. In some embodiments, the drug injection manifold 150 may be embedded in the body of the first and second adhesion patches 102, 104. In other embodiments, the drug injection manifold 150 may be removably coupled to the first and second adhesion patches 102, 104 (FIGS. 111A-111H). The removable drug injection manifold 150 may be applicable to other surgical closure devices as well, such as those described in U.S. Pat. Nos. 9,050,086 and 9,089,328 and U.S. patent application Ser. No. 14/625,366, the contents of which are incorporated herein by reference.

In a particularly preferred embodiment of the surgical closure device 100, the first and second rails 112, 114 are configured so that they form a central lumen or cavity 110 into which the drug injection manifold 150 can be inserted. The cavity connects to several openings 160 through which the drug injection needles 154 project into the patient. In the embodiment shown, the openings 160 align with the central parting line 124 of the device. In addition, there may be one or more larger drainage openings 162 along the central parting line 124 of the device. In the configuration shown, the drug injection manifold 150 can be used in one or both of two modes. The drug injection manifold 150 can be inserted into the cavity 110 between the first and second rails 112, 114 prior to closure of the incision, so that an anesthetic, such as lidocaine, can be continuously or intermittently injected into the incision to control pain in the incision and surrounding tissue during healing. Additional drugs, such as antibiotics, steroids or NSAIDs, may also be injected to control infection, to reduce inflammation and/or to reduce scar formation. In addition, cells and cell matrix such as stem cells can be injected too. When used in this mode, the drug injection needles 154 may have blunt tips because they can be inserted directly into the open incision. Alternatively, a drug injection manifold 150 with sharpened drug injection needles 154 can be inserted into the cavity 110 between the first and second rails 112, 114 before adhering the surgical closure device 100. The drug injection needles 154 will pierce the skin as the surgical closure device 100 is adhered to the skin. When used in this mode, the drug injection manifold 150 can be used to anesthetize the skin and surrounding tissue prior to making the incision. The incision can be made just adjacent to the drug injection needles 154. The drug injection manifold 150 can be also be used after closing the incision to control pain in the incision and surrounding tissue during healing.

In an alternative configuration, the cavity 110 and the openings 160 may be offset from the central parting line 124 of the device. A drug injection manifold 150 with sharpened drug injection needles 154 can be inserted into the tissue beside the incision site before or after making the incision. A first and second drug injection manifold 150 with sharpened drug injection needles 154 can be inserted into the tissue on both sides of the incision site before or after making the incision. The first and second drug injection manifolds may be connected together in a horseshoe or U-shaped configuration. For example, while the main tube 152 and the drug injection needles 154 are shown in FIG. 4 as placed along the inner edges of the first and second adhesion patches 102 and 104 to be immediately adjacent the incision for the delivery of drug(s) or other therapeutic agent(s) to the incision, other placements are contemplated as well. For instance, the main tube 152 and the drug injection needles 154 and/or the catheters 153 (described further below) may be positioned within the first and/or second adhesion patches 102 and 104 at or near the respective midline(s) of each panel such that drug(s) or other therapeutic agent(s) may be delivered to the tissue surrounding and/or adjacent the incision (FIGS. 110A-110F, 111A-111H). For example, the drug injection needles 154 and/or the catheters 153 may extend into the tissue such as 8 mm to 1 cm into the tissue. For example, the drug injection needles 154 and/or the catheters 153 may extend subdermally to deliver a drug, such as a painkiller, to the tissue near a surgical incision. The drug injection needles 154 and/or the catheters 153 may extend into the tissue at the same depth or at a variety of different depths. Optionally, the needles 154 and/or the catheters 153 may have a range of lengths so that the drug(s) that will be delivered via the catheters 153 can reach different layers of the skin. In some embodiments, the lengths of the needles 154 and/or the catheters 153 are such that drug(s) can be delivered subdermally. As an example-most of the catheters 153 may be 6 mm long. In some embodiments, only the needles 154, only the catheters 153, or only a combination of the needles 154 and the catheters 153 will deliver drug(s). For instance, every fifth or so needle 154 in the line of needles 154 will not have a corresponding catheter 153 such that said needle 154 will be used to deliver the drugs or agents alone.

Another option is that the needles will be inserted in the middle but the tip of the needles will be curved in such a way that when the two sides of the cut are approximated, the needles will penetrate the tissue from the sides and infiltrate the drug into it. Such a needle can be made out of a nickel-titanium alloy as an example. The needles 154 and/or the catheters 153 may be curved and/or angled to face toward the incision when the needles 154 and/or the catheters 153 are positioned in the tissue, for example. In some embodiments, the needles 154 and/or the catheters 153 may be splayed. For instance, adjacent needles 154 and/or catheters 153 originating from the same main tube 152 may face opposite directions relative to the incision to distribute drug(s) more evenly throughout a volume of tissue.

One or more drugs may be delivered by a syringe, a syringe pump, a pressurized reservoir or a micropump connected to a reservoir. A drug pump may be energized with a resilient member, for example a nickel-titanium spring that presses against a drug reservoir. Manual force to pressurize a pump or drug reservoir can also be provided by the patient or a caregiver. One or more single dose squeezable ampoules connectable to an injection port on the device may be provided for filling a drug reservoir within the device and/or for direct injection into or adjacent to the incision through the drug injection manifold. Optionally, the anesthetic dosage may be controlled by the patient. Optionally, a programmable pump may be used to control the rate and dosage of drug delivery.

Figure 49:
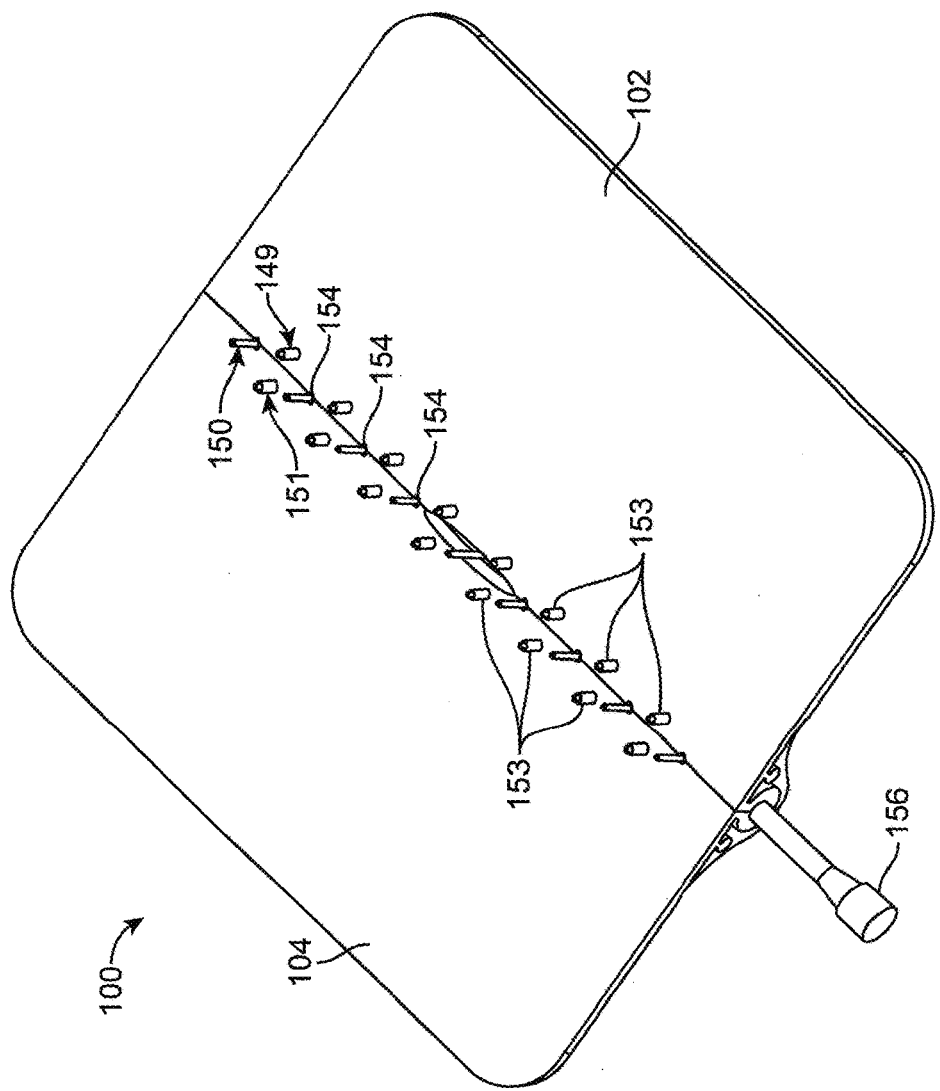
FIG. 49 is a perspective view of the underside of a surgical closure device having first, second and third drug injection manifolds.
Figure 110A:
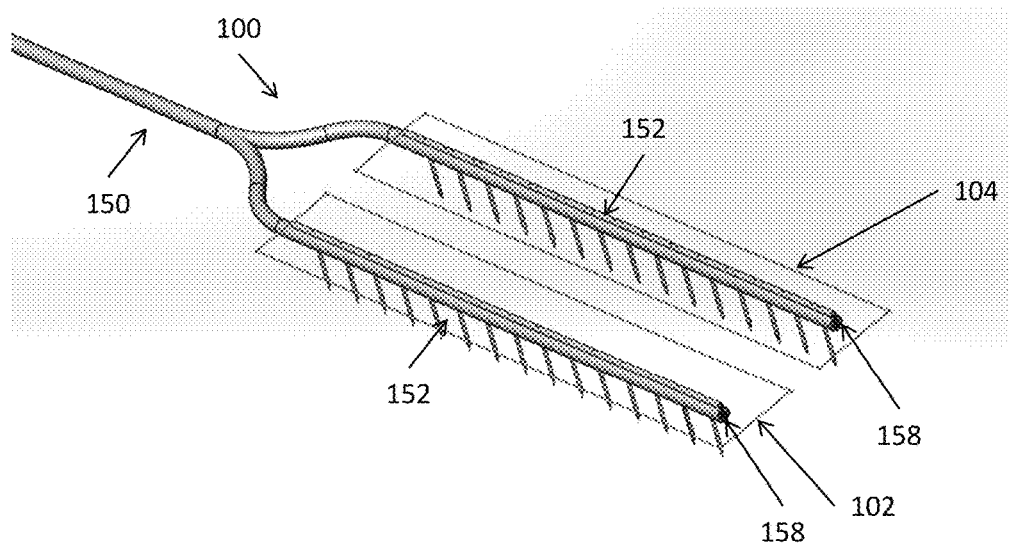
FIGS. 110A-110F illustrate a closure device having drug injection manifolds.
Figure 110B:
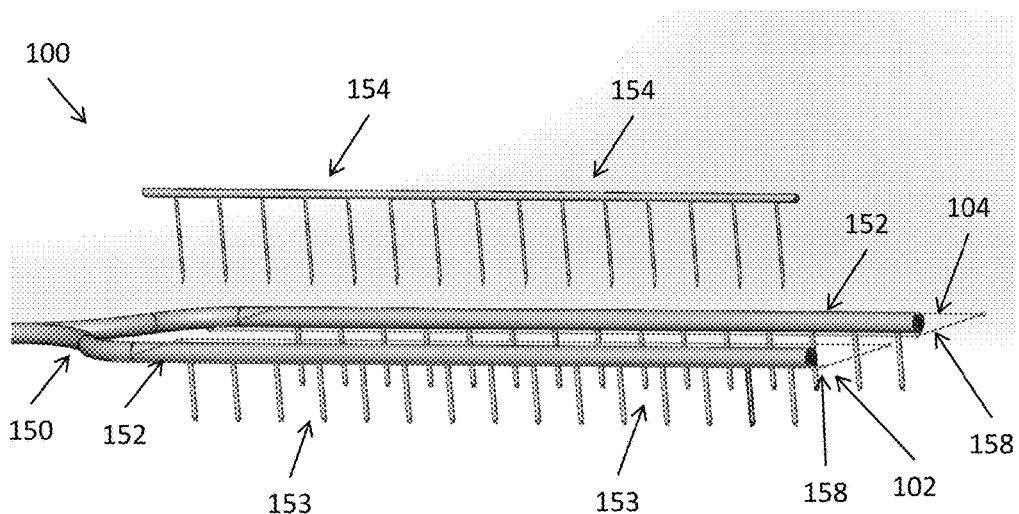
Figure 110C:
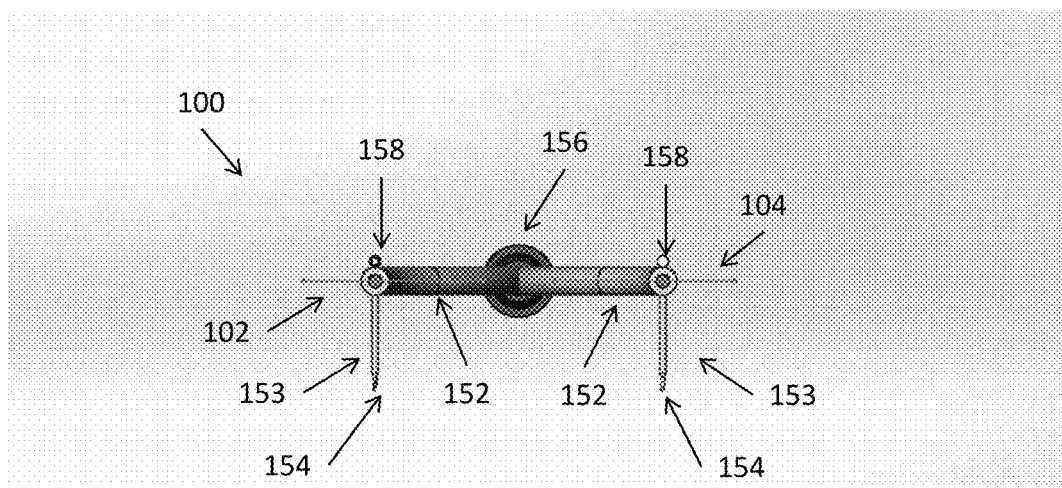
Figure 110D:
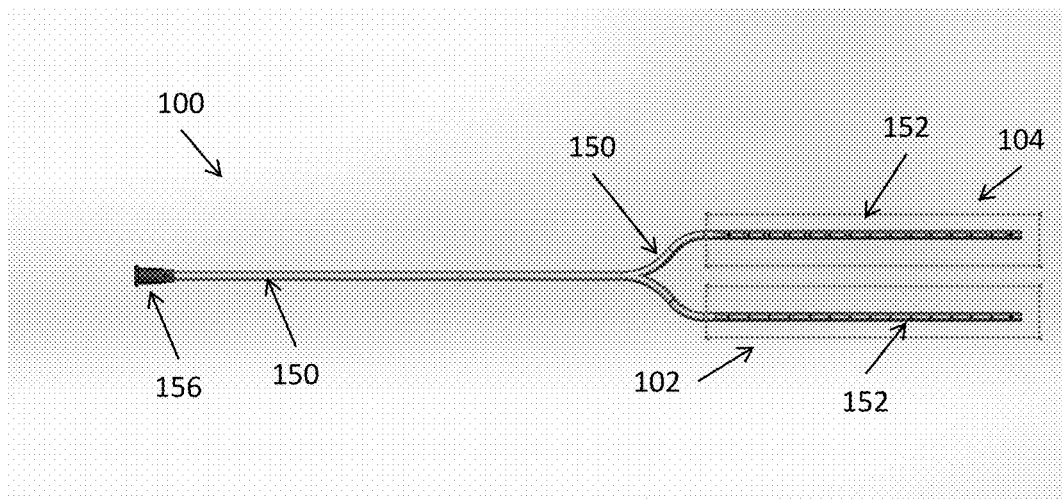
Figure 110E:
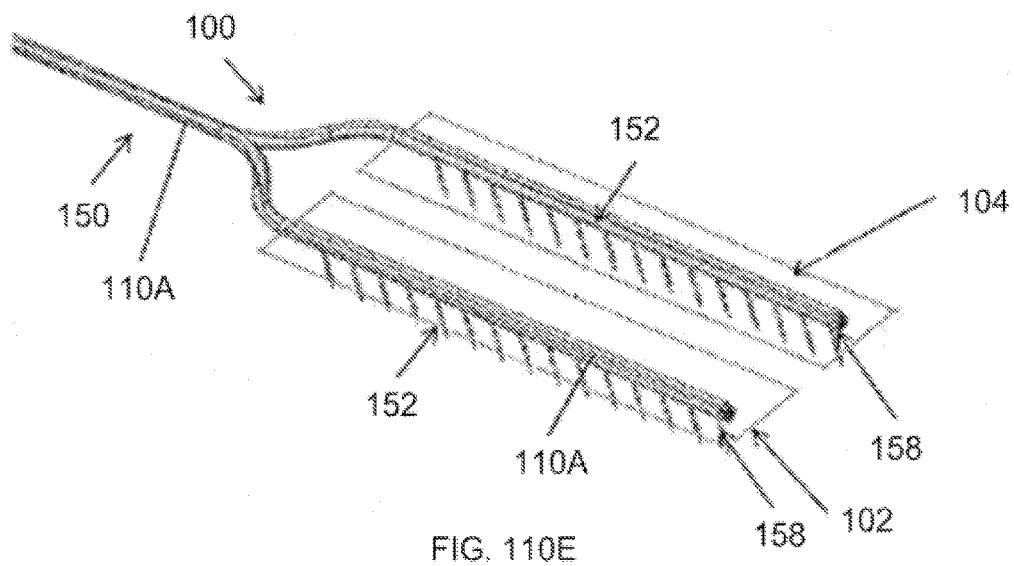
Figure 110F:
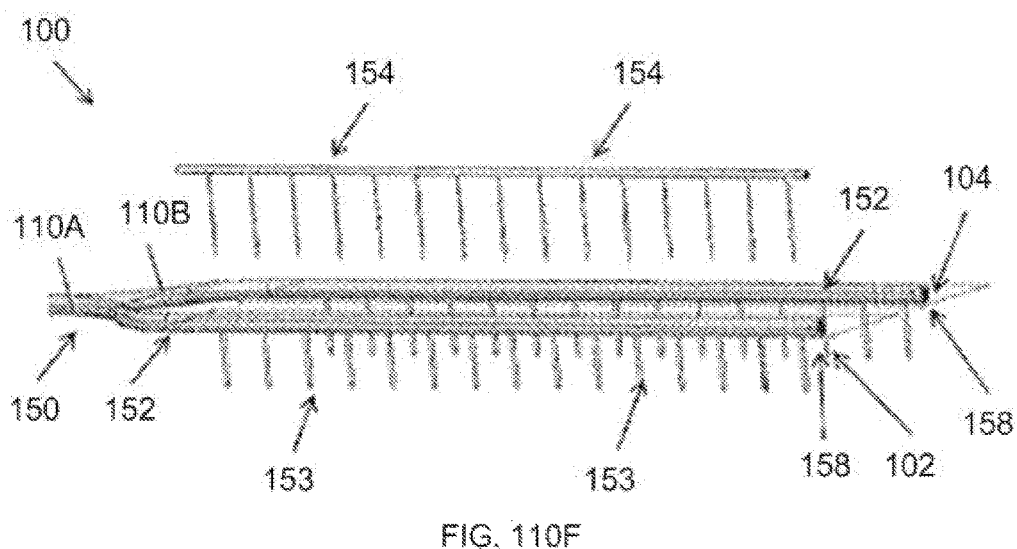

FIG. 49 is a perspective view from the underside of a surgical closure device 100 showing additional options for the drug injection feature of the device. The surgical closure device 100 is shown with a first drug injection manifold 150 located at the center line of the device with drug injection needles 154 to be inserted into the incision and second and third drug injection manifolds 149, 151 located to the left and/or right side of the incision. The drug injection manifolds 149, 150, 151 may all be connected to a single proximal connector 156 (FIGS. 110C, 110D, 111A-111H), or alternatively each manifold may have its own separate proximal connector. Optionally, the drug injection manifolds 149, 150, 151 may be configured as described above in connection with FIGS. 4 and 5. For instance, the drug injection manifolds 149, 150, 151 may be aligned with a mid or centerline of an individual adhesion patch as in FIGS. 110A-110F, 111A-111H. Alternatively however, one or more of the drug injection manifolds 149, 150, 151 may be configured with more flexible plastic drug injection catheters 153 arranged coaxially around drug injection or tissue piercing needles 154. These drug injection or tissue piercing needles 154 may have a solid core or a hollow core. For instance, the drug injection or tissue piercing needles 154 may have a hollow core to remove tissue when larger puncture sites for the plastic drug injection catheters 154 are desired. For greater patient comfort, once a drug injection manifold has been inserted, the sharpened drug injection or tissue piercing, needles 154 may be withdrawn, leaving only the plastic drug injection catheters 153 behind. Optionally, solid, sharpened stylets may be used in place of the drug injection needles 154 in this configuration of the device. The drug injection or tissue piercing needles 154 may thus serve as a guide for the placement of the plurality of plastic drug injection catheters 153 into the tissue (FIGS. 110A-110F, 111A-111H). For instance, the plastic drug injection catheters 153 may be positioned to be coaxial with corresponding drug injection or tissue piercing needles 154 (FIGS. 110B, 110F). Both the needles 154 and the catheters 153 may be arranged in a configuration much like a single-lined comb, with the spine of the needles 154 disposed over the spine (or main, central tube) of the catheters 153 and the needles 154 penetrating the spine of the catheters 153 into the individual catheters 153 (FIGS. 110A, 110E, 111A-111H). After placement of the catheters 153 and the needles 154 in the tissue, the needles 154 may be withdrawn and lifted from the catheters 153 and the main, central tube of the catheters 153 (FIGS. 110B, 110F). The spine or main tube 152 of the catheters 153 may comprise a self-sealing material (such as a self-closing rubber or silicone material) such that the punctures generated by the needles 154 on spine or main tube 152 of catheters 153 may self-close after the needles 154 are withdrawn. FIG. 49 shows the surgical closure device 100 after the drug injection needles 154 of the second and third drug injection manifolds 149, 151 have been withdrawn, leaving the plastic drug injection catheters 153 in place. In one optional configuration, the second and third drug injection manifolds 149, 151 may be attached to the first and second adhesion patches 102, 104 so that the drug injection needles 154 (and the optional catheters 153) are inserted into the patient's tissue at the same time as the surgical closure device 100 is applied to the skin. This configuration allows the area to be anesthetized through the second and third drug injection manifolds 149, 151 prior to making the incision. Optionally, the first drug injection manifold 150 may be omitted in this configuration. In some embodiments, the device 100 may be configured to generate an electric field(s) adjacent the incision to facilitate tissue healing. As shown in FIGS. 110E and 110F, the device 100 may comprise a first conductor 110A coupled to the first adhesion patch 102 and a second conductor 110B coupled to the second adhesion patch 104. The first conductor 110A may generate a positive electric charge and the second conductor 110B may generate a negative electric charge, or vice versa, to generate an intra-tissue electric field at the tissue adjacent an incision between the first and second adhesion patches 102, 104. The charges of the first and second conductors 110A, 110B may alternate charges. The proximal ends of the first and second conductors 110A, 110B may be coupled to an external power supply such as a battery pack. In some embodiments, the injection manifold 150, the catheters 153, and/or the needles 154 may be conductive to generate the intra-tissue electric field themselves.

Alternatively or in addition, one or more drugs can be sprayed, brushed, dripped, poured or otherwise applied directly to the incision prior to closure. Alternatively or in combination, one or more components of the surgical closure device 100 may be comprised of, coated with, or applied with one or more drug(s) or other therapeutic or diagnostic agents for various purposes, including but not limited to one or more of an antifungal, antibacterial, antimicrobial, antiseptic, anti-inflammatory, or medicated material and/or agents. For example, the interior surface of the injection manifold 150 may be so coated. In many embodiments, such materials and/or agents may comprise one or more of silver, iodide, zinc, chlorine, copper, or natural materials such as tea tree oil as the active agent. Examples of such antifungal, antibacterial, antimicrobial, antiseptic, or medicated materials include, but are not limited to, the Acticoat™ family of materials available from Smith & Nephew plc of the U.K., the Acticoat® Moisture Control family of materials available from Smith & Nephew plc of the U.K., the Contreet® Foam family of materials available from Coloplast A/S of Denmark, the UrgoCell® Silver family of materials available from Urgo Limited of the U.K. (a subsidiary of Laboratories URGO of France), the Contreet® Hydrocolloid family of materials available from Smith & Nephew plc of the U.K., the Aquacel® Ag family of materials available from ConvaTec Inc. of Skillman, N.J., the Silvercel® family of materials available from Kinetic Concepts, Inc. of San Antonio, Tex., Actisorb® Silver 220 available from Kinetic Concepts, Inc. of San Antonio, Tex., the Urgotul® SSD family of materials available from Urgo Limited of the U.K. (a subsidiary of Laboratories URGO of France), the Inadine® family of materials available from Kinetic Concepts, Inc. of San Antonio, Tex., the Iodoflex® family of materials available from Smith & Nephew plc of the U.K., the Sorbsan Silver™ family of materials available from Aspen Medical Europe Ltd. of the U.K., the Polymem Silver® family of materials available from Ferris Mfg. Corp. of Burr Ridge, Ill., the Promogram™ family of materials available from Kinetic Concepts, Inc. of San Antonio, Tex., the Promogram Prisma™ family of materials available from Kinetic Concepts, Inc. of San Antonio, Tex., and the Arglaes® family of materials available from Medline Industries, Inc. of Mundelein, Ill. In another example, the exterior and/or interior of the drug injection manifold(s) 150 may be coated with an anti-clotting agent such as heparin to help maintain the patency of the drug injection manifold(s). it may also be coated with antimicrobial agents or other desired therapeutic agents. In another example, the interior and/or exterior of the drug injection manifold(s) 150 may be coated or comprised of a low friction material such as PTFE to facilitate smooth fluid or drug delivery and/or later removal from the tissue. The above disclosure, such as that of drug injection manifold 150, while described with respect to the surgical closure device 100, may be equally applicable to the closure devices described in commonly owned U.S. Pat. Nos. 8,313,508, 8,323,313, 8,439,945, 9,050,086, and 9,089,328; U.S. Patent Publication No. 2013/0066365; and PCT application nos. US 2010/000430, US 2011/139912, US 2011/40213, US 2011/34649, and US 2013/067024, the contents of which are incorporated herein by reference. The components of such surgical closure device may also be comprised of, be coated with, or otherwise incorporate one or more of an antifungal, antibacterial, antimicrobial, antiseptic, or medicated material, including but not limited to one or more of the materials listed above.

FIGS. 111A-111H show a method of using a surgical closure device 100a with the injection manifold 150. The surgical closure device 100a may be similar to the surgical closure device 100 described above. For instance, the surgical closure device 100a may comprise a first adhesion patch 102 and a second adhesion patch 104 for placement adjacent the lateral sides of a wound, cut, or incision. The first and second adhesion patches 102, 104 may be coupled together with a plurality of lateral connectors 100b.

Figure 111A:
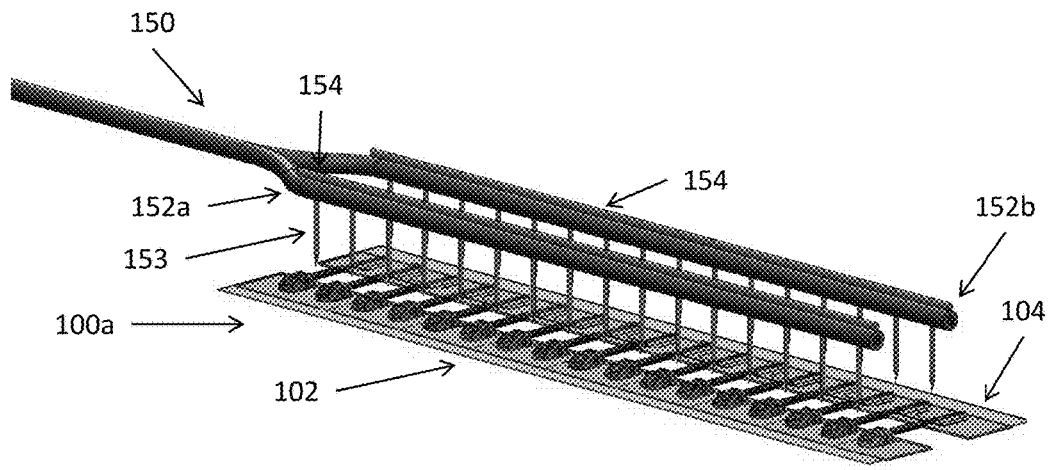
Figure 111B:
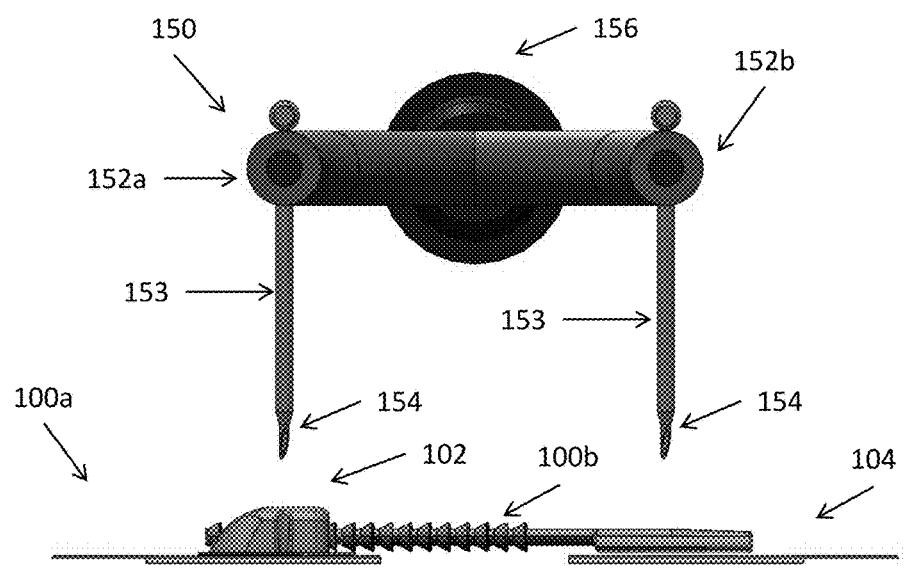

As shown in FIGS. 111A and 111B, the surgical closure device 100a may be separated from the injection manifold 150. The injection manifold 150 may comprise a first main tube 152a corresponding to the first adhesion patch 102 and a second main tube 152b corresponding to the second adhesion patch 104. The first main tube 152a may be coupled to a plurality of fluid injection catheters 153. Similarly, the second main tube 152b may coupled to a plurality of fluid injection catheters 153 as well. The proximal ends of the first and second main tubes 152a, 152b may be coupled together such that a single fluid source may be used to deliver fluid thereto. The injection catheters 153 may be axially aligned to form a comb-like configuration with each of the first and second main tubes 152a, 152b. As described above and herein, an array or plurality of needles 154 in a comb-like configuration may pierce the first and second main tubes 152a, 152b so that the needles 154 are coaxial with and extend through the lumens of the catheters 153. As described above and herein, the catheters 153 and/or other components of the surgical closure device 100a and injection manifold 150 may be coated with various drug(s) or materials such as antiseptic or anticoagulation agents. The inner surfaces of the catheters 153 may be coated with an antiseptic agent or an anticoagulation agent such as heparin, for example.

Figure 111C:
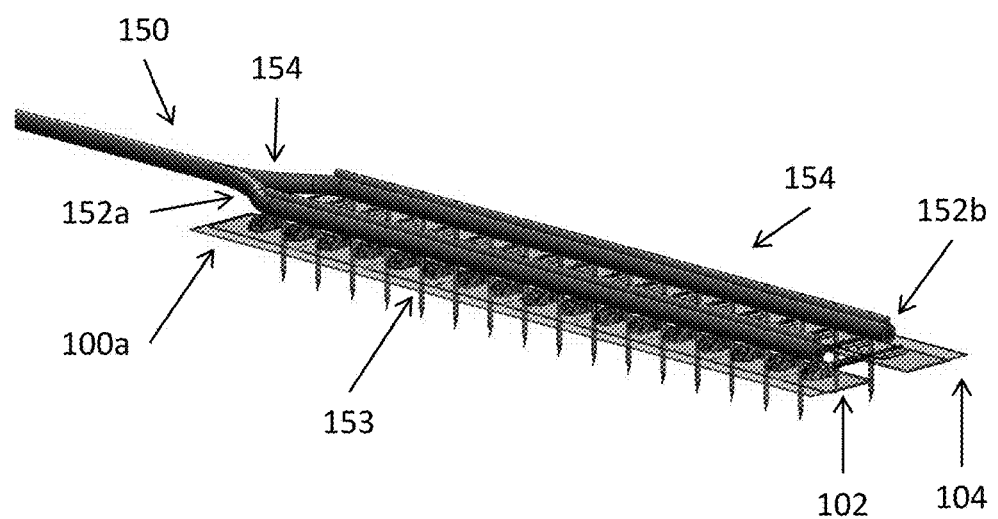
Figure 111D:
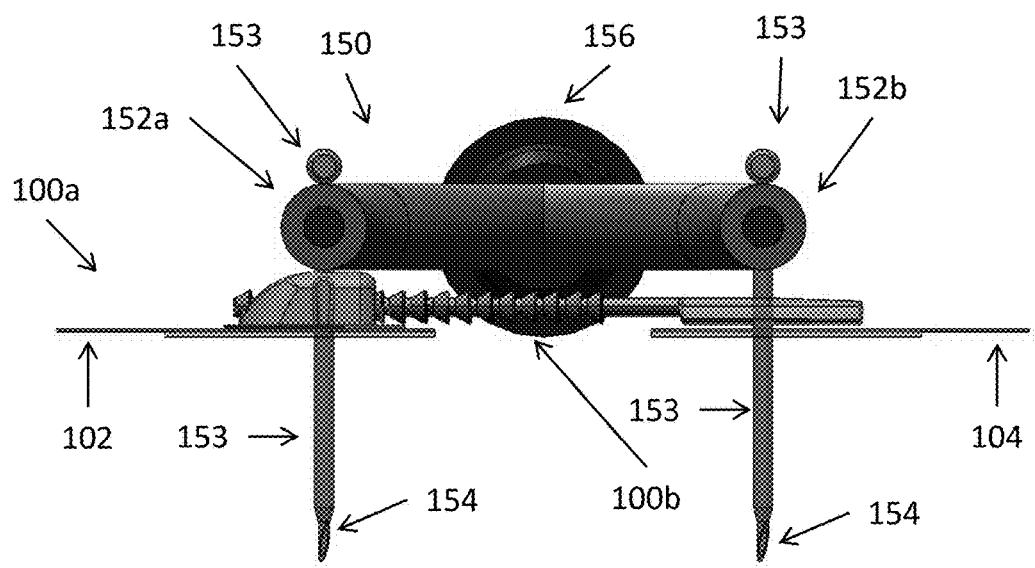

As shown in FIGS. 111C and 111D, the injection manifold 150 may be advanced through the surgical closure device 100a. For instance, the surgical closure device 100a may be first appropriately aligned with and adhered to the skin of a subject before the injection manifold 150 is placed over the surgical closure device 100a and pressed down, advancing the needles 154 and the catheters 153 through the skin. As discussed above, the needles 154 may have a hollow core to remove tissue so as to generate larger punctures or may have a solid core. As discussed above, the needles 154 punctures the tissue to facilitate the advancement of the catheters 153 into the tissue as the catheters 153 may otherwise be too compliant to be advanced into the tissue on their own. Alternatively, the catheters 153 may comprise arrays of flexible needles that can penetrate tissue as well as deliver drug(s) or other fluids such that additional needle arrays 154 may not be required. The needles 154 and the catheters 153 may be advanced into the tissue so that drug(s) or other fluids can be delivered subdermally.

In some embodiments, the injection manifold 150 may be used alone as a drug delivery vehicle. The injection manifold 150 may be pressed down directly onto the skin of a patient without the surgical closure device 100a intervening. Alternatively, other types of bandages or covering aside from the surgical closure devices 100 and 100a may be placed to intervene between the injection manifold 150 and the skin of the patient. As discussed below, the needle arrays 154 may be subsequently removed and the drug(s) or other fluid may be delivered through the catheters 153 of the injection manifold 150 into the tissue. Also as discussed below and herein, the catheters 153 may themselves comprise flexible fluid delivery needles such that needle arrays 154 may not be required to generate the tissue punctures.

Figure 111E:
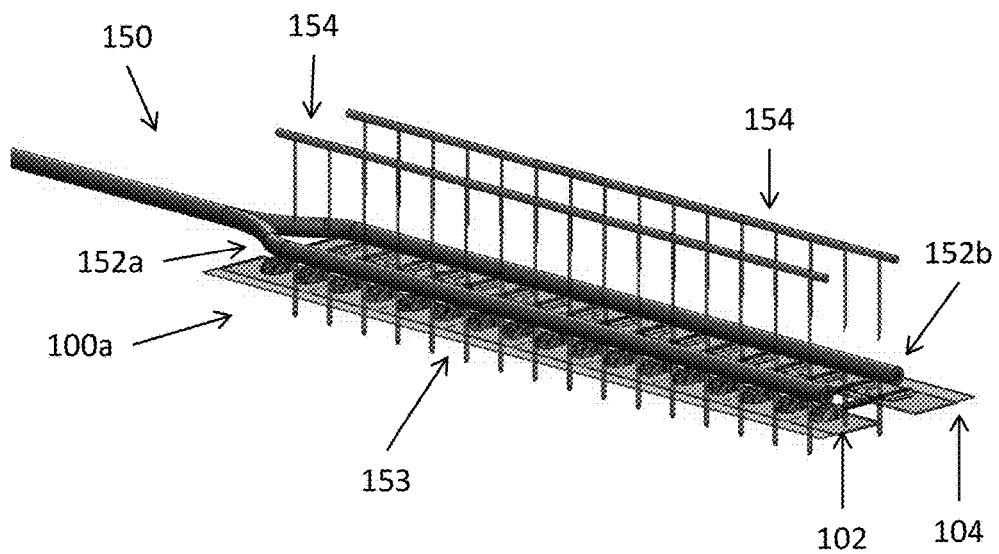
Figure 111F:
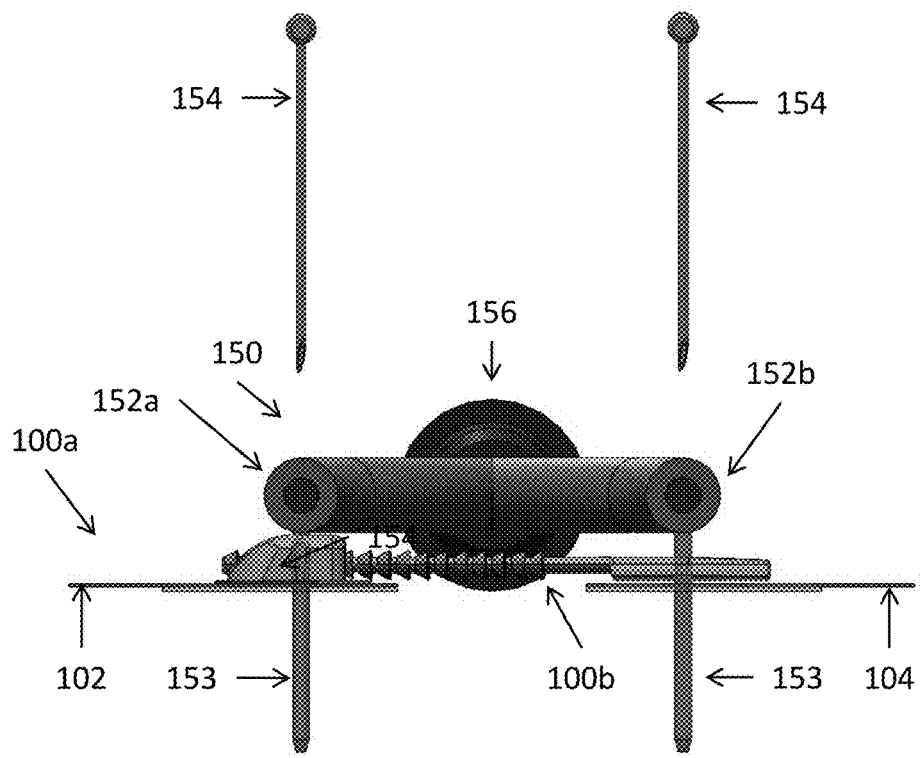

As shown in FIGS. 111E and 111F, the needle arrays 154 may be removed from the injection manifold 150. For instance, after the surgical closure device 100a has been placed over the skin of the subject and the injection manifold 150 has been pressed downward to be advanced into the tissue, the needle arrays 154 may be lifted and withdrawn from the main tubes. As described above and herein, the main tubes 152a, 152b may comprise a self-sealing material such that the punctures to the main tubes 152, 152b from the needle arrays 154 may self-close after the needle arrays 154 are removed.

Figure 111G:
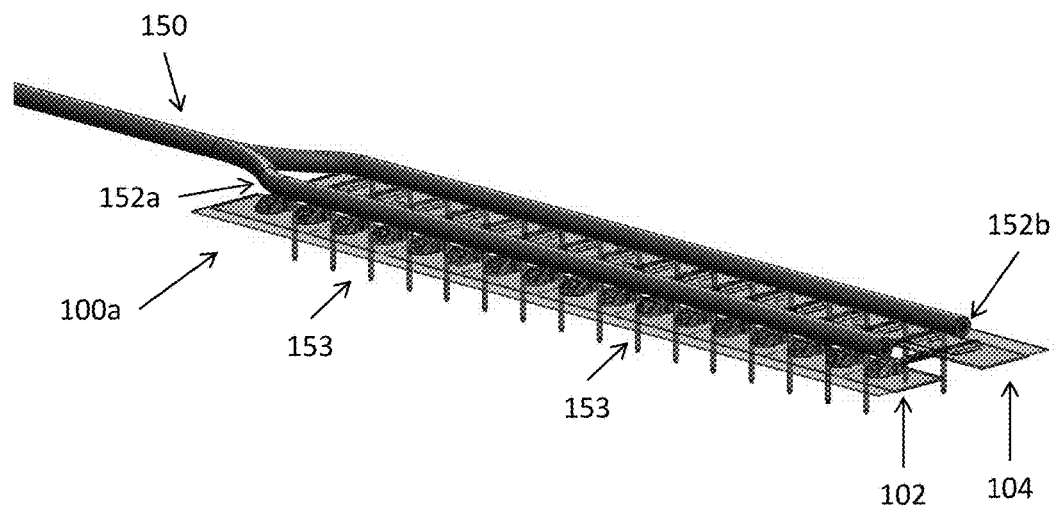
Figure 111H:
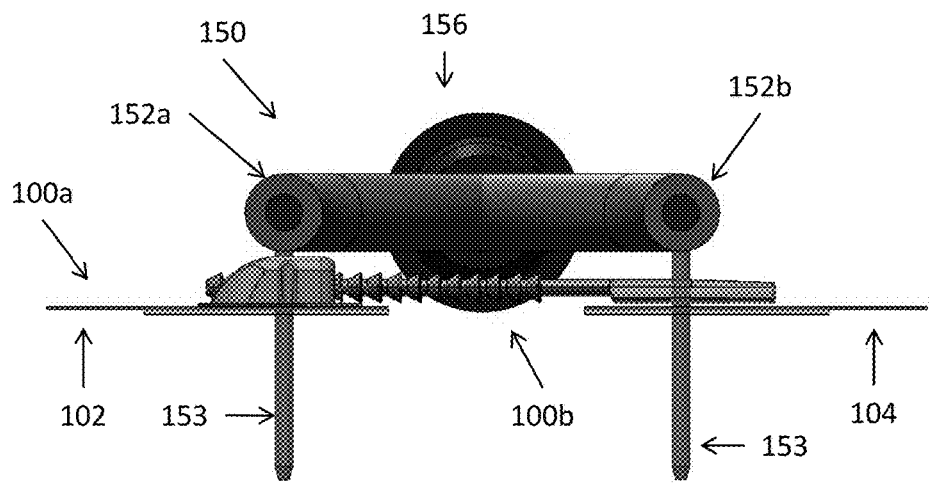

FIGS. 111G and 111H show the final surgical closure device 100a coupled with the injection manifold 150 with the needle arrays 154 removed. With the needle arrays 154 removed, the lumens of the main tubes 152a, 152b and the catheters 153 may be less obstructed from fluid flow. As described above and herein, drug(s) or other fluid may be provided from a fluid source (such as a squeezable ampoule, which may be single use ampoule, or a syringe) coupled to a proximal connector (such as a Luer connector) coupled to the proximal ends of the first and second main tubes 152a, 152b, and the drug(s) or other fluid may be delivered subdermally to the tissue adjacent the wound, cut, or incision subdermally. As described above and herein, for example, the various drug(s) such as local anesthetics, anti-keloid drugs (e.g., steroids), or antibiotics may be delivered. As shown in FIGS. 111A-111H, the proximal ends of the main tubes 152a, 152b may be coupled together to connect to a single Luer connector. Alternatively, the proximal ends of the main tubes 152a, 152b may be separated and connected individual to respective Luer connectors. As described above and herein, the surgical closure device 100a and/or the injection manifold 150 may generate an intra-tissue electric field, such as through the catheters 153, the needles 154, or other conductor(s), to enhance recovery.

Figure 7:
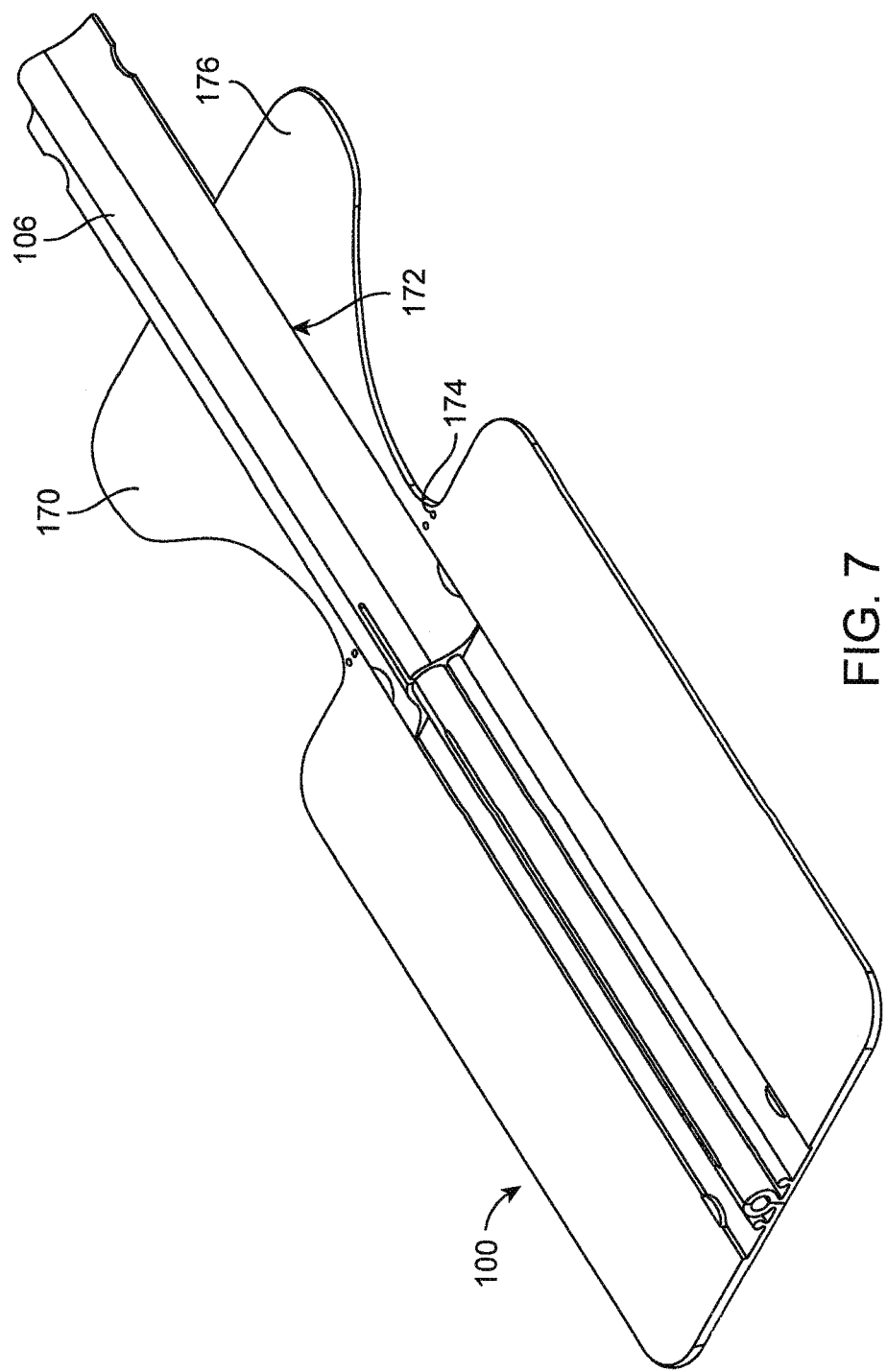
FIG. 7 is a perspective drawing of a surgical closure device with a removable appendage with a rail extension to park the binder during the surgical procedure.
Figure 8:
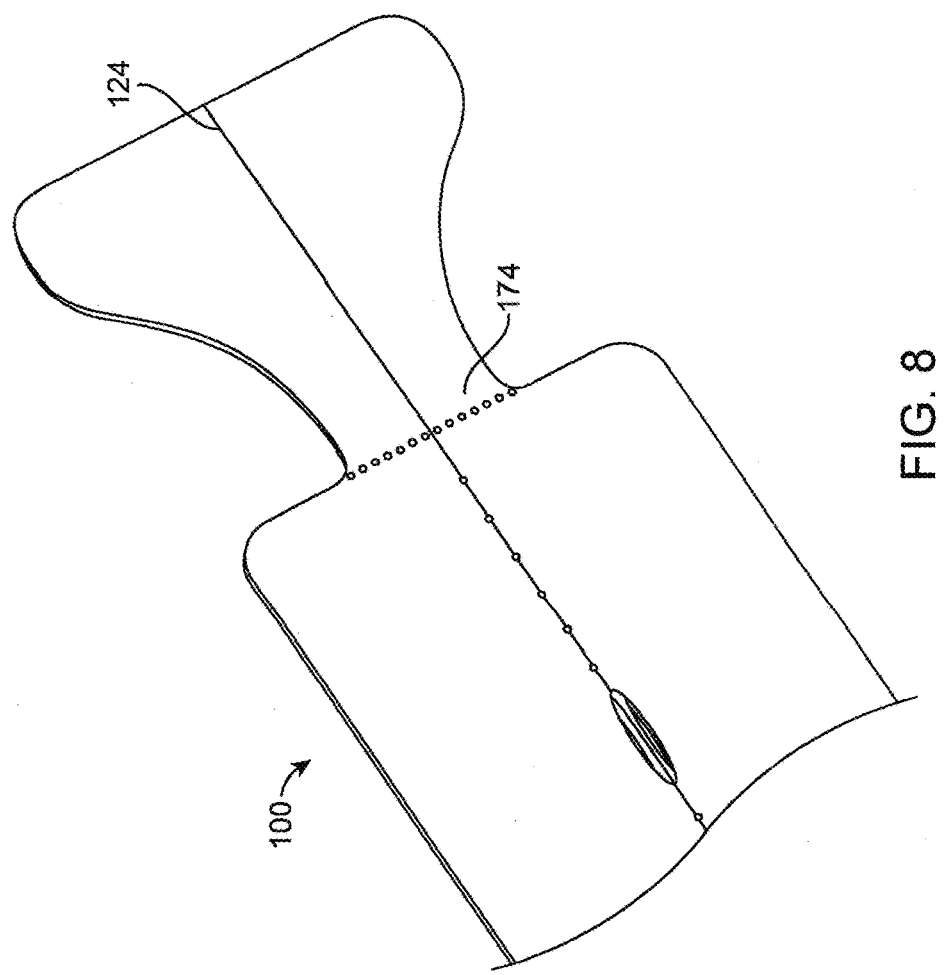
FIG. 8 is a perspective view from the underside of the surgical closure device of FIG. 7 showing the removable appendage.

FIG. 7 is a perspective drawing of a surgical closure device 100 with a removable appendage 170 with a rail extension 172 to park the binder 106 during the surgical procedure. FIG. 8 is a perspective view from the underside of the surgical closure device 100 of FIG. 7 showing the removable appendage 170. The removable appendage 170 is attached at one side of the surgical closure device 100 to both the first adhesion patch 102 and the second adhesion patch 104. There is no adhesive on the underside of the removable appendage 170. The first rail 112 and the second rail 114 extend onto the removable appendage 170 to form a rail extension 172. In use, the binder 106 is slid off of the first rail 112 and the second rail 114 and parked on the rail extension 172 of the removable appendage 170 during the surgical procedure. This has a number of advantages. First, it simplifies the step of closing the incision because the binder 106 is already aligned with and mounted on the first rail 112 and the second rail 114. Second, if the central parting line 124 extends at least part way onto the removable appendage 170, it will allow the incision to be opened wide with a retractor without physically detaching the first adhesion patch 102 from the second adhesion patch 104. Third, because the first adhesion patch 102 and the second adhesion patch 104 are both attached to the removable appendage 170, it assures that the two sides of the incision will be precisely aligned with one another when the surgical closure device 100 is closed at the end of the procedure. After the surgical procedure is completed, the binder 106 is slid back onto the first rail 112 and the second rail 114 to close the incision. The removable appendage 170 will preferably be made with tabs 176 that can be used to grip the surgical closure device 100 to make it easier to slide the binder 106 back onto the first and second rail 112, 114. After the surgical closure device 100 is closed, the appendage 170 may be cut off or may be torn off using perforations 174 that are optionally provided.

Figure 9:
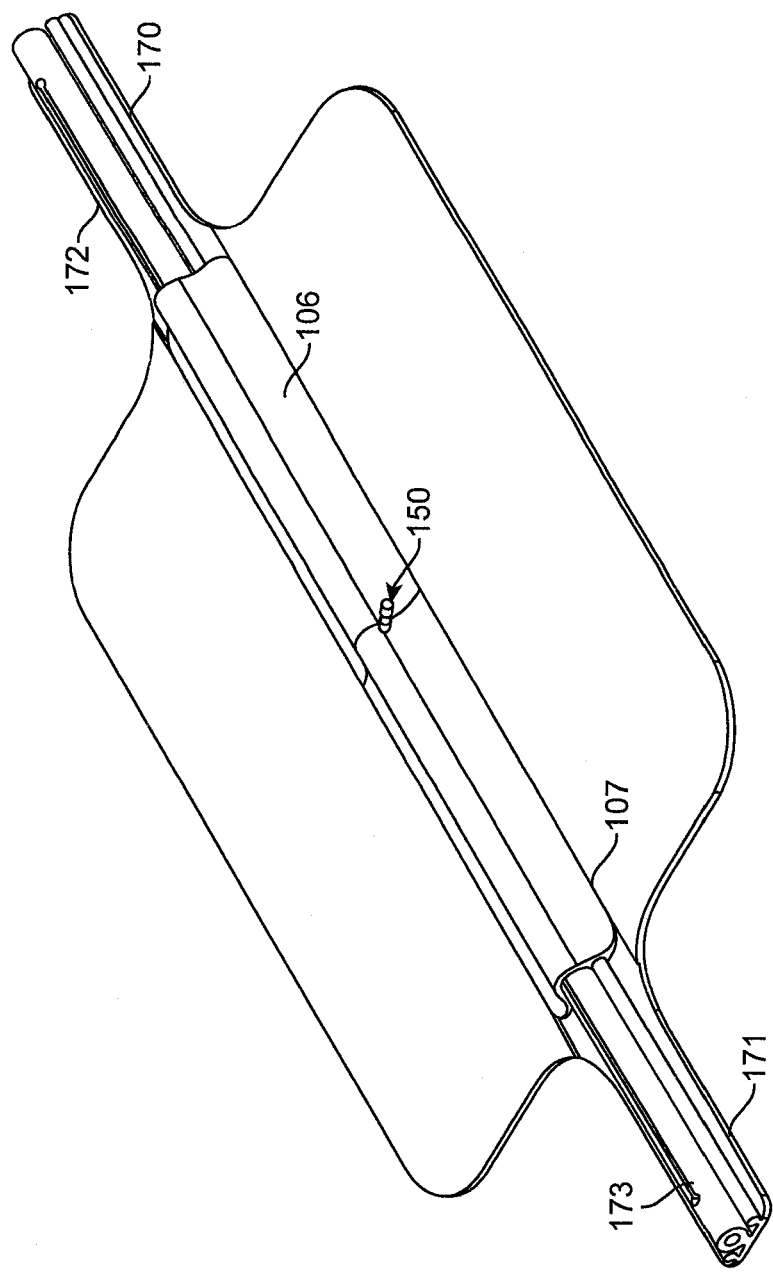
FIG. 9 is a perspective drawing of a one-piece surgical closure device with dual binders and rail extensions.
Figure 10:
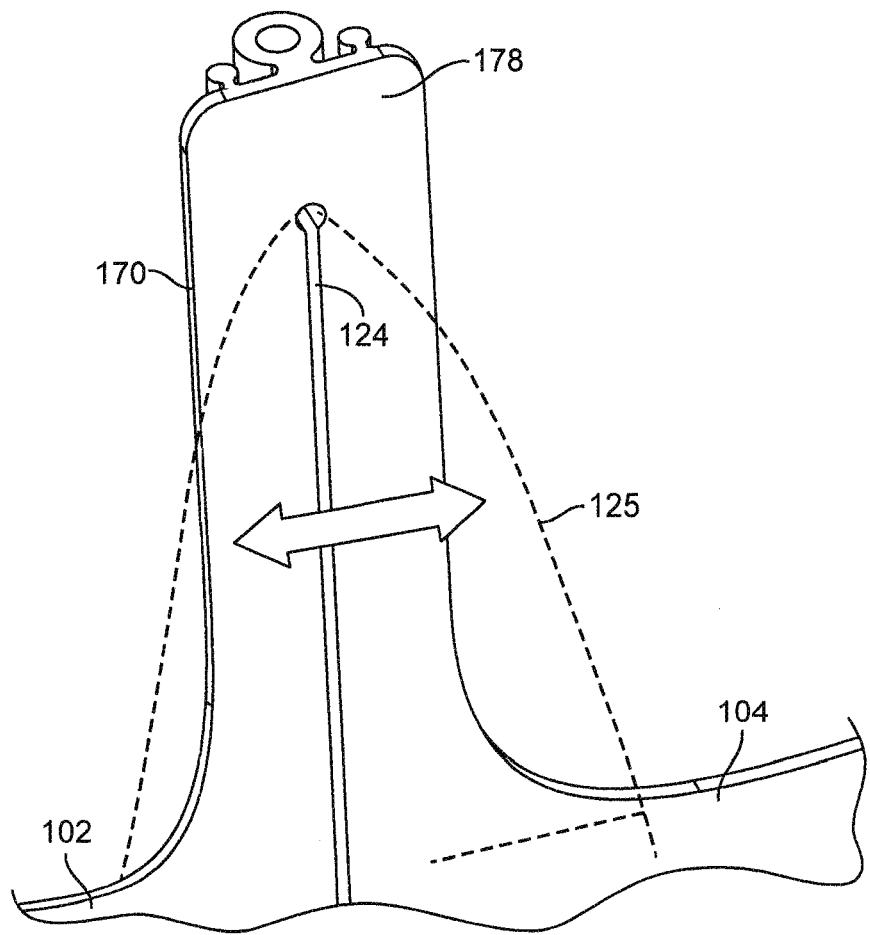
FIG. 10 is a perspective view from the underside of the surgical closure device of FIG. 9 showing construction details of the ends of the device.

FIG. 9 is a perspective drawing of a one-piece surgical closure device 100 with dual binders 106, 107 and appendages 170, 171. FIG. 10 is a perspective view from the underside of the surgical closure device 100 of FIG. 9 showing construction details of the ends of the device 100. This embodiment takes the previous concept one step further by adding a second appendage 171 and a second rail extension 173 on the opposite end of the closure device 100 from the appendage 170 and the rail extension 172 shown in FIGS. 7 and 8. There is no adhesive on the underside of the appendages 170, 171. Optionally, the appendages 170, 171 may include gripping tabs 176 and may have perforations 174 to make them removable as shown in FIGS. 7 and 8. As shown in FIG. 10, the first adhesion patch 102 and the second adhesion patch 104 are joined together by the end portions 178 of the appendages 170, 171. The central parting line 124 of the device stops short of the end portions 178. The central parting line 124 can be easily opened with surgical retractors, as shown by dashed lines 125, while keeping the one-piece device intact. In use, the binders 106, 107 can be parked on the rail extensions 172, 173 of the appendages 170, 171 during the surgical procedure. Because the binders 106, 107 are already aligned with and mounted on the first rail 112 and the second rail 114, it is easier to close the surgical closure device 100 after completion of the surgical procedure.

Optionally, the surgical closure device 100 of FIG. 9 may include a drug injection manifold 150 similar to that shown in FIGS. 4 and 5, except that the proximal connector 156 is located in the center of the main tube 152 between two closed distal ends 158. FIG. 11 shows insertion of a drug injection manifold into the surgical closure device 100 of FIG. 9. The proximal connector 156 is positioned at a right angle to the drug injection needles 154 so that it will have a low profile when it snaps into a slot 180 in the first rail 112.

FIG. 12 shows the surgical closure device 100 of FIG. 9 with the dual binders 106, 107 closing around the proximal connector 156 of the drug injection manifold 150. The binders 106, 107 will preferably have notches 182, 183 cut into their ends so that they will fit around the proximal connector 156 of the drug injection manifold 150 without a gap between them.

Figure 13:
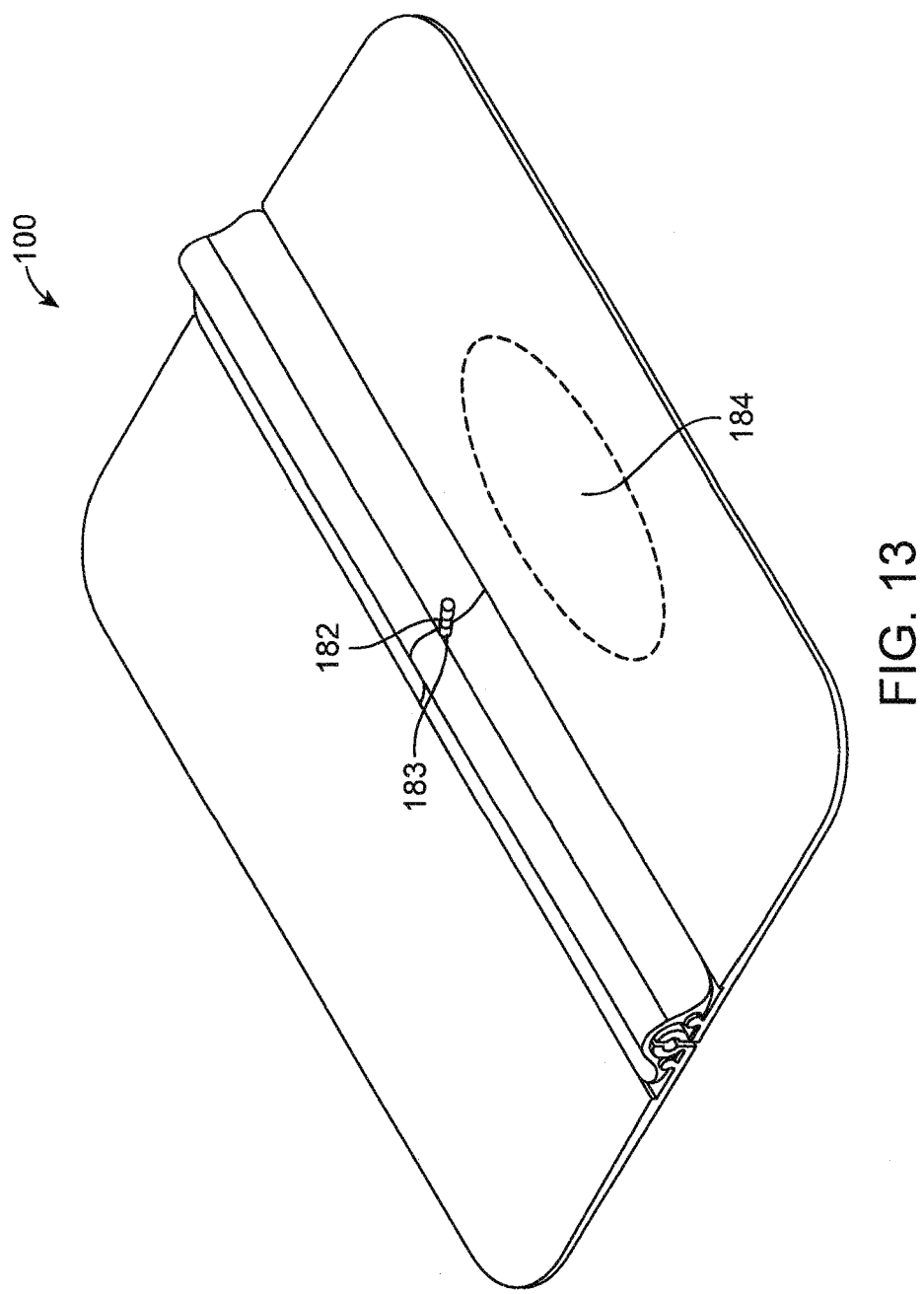
FIG. 13 shows the surgical closure device of FIG. 9 after removal of the rail extensions.

FIG. 13 shows the surgical closure device 100 of FIG. 9 after closure of the surgical incision. The appendages 170, 171 of the surgical closure device 100 have been removed after closing the surgical incision. Reference number 184 indicates a potential position on the device for an integrated drug reservoir.

Figure 14:
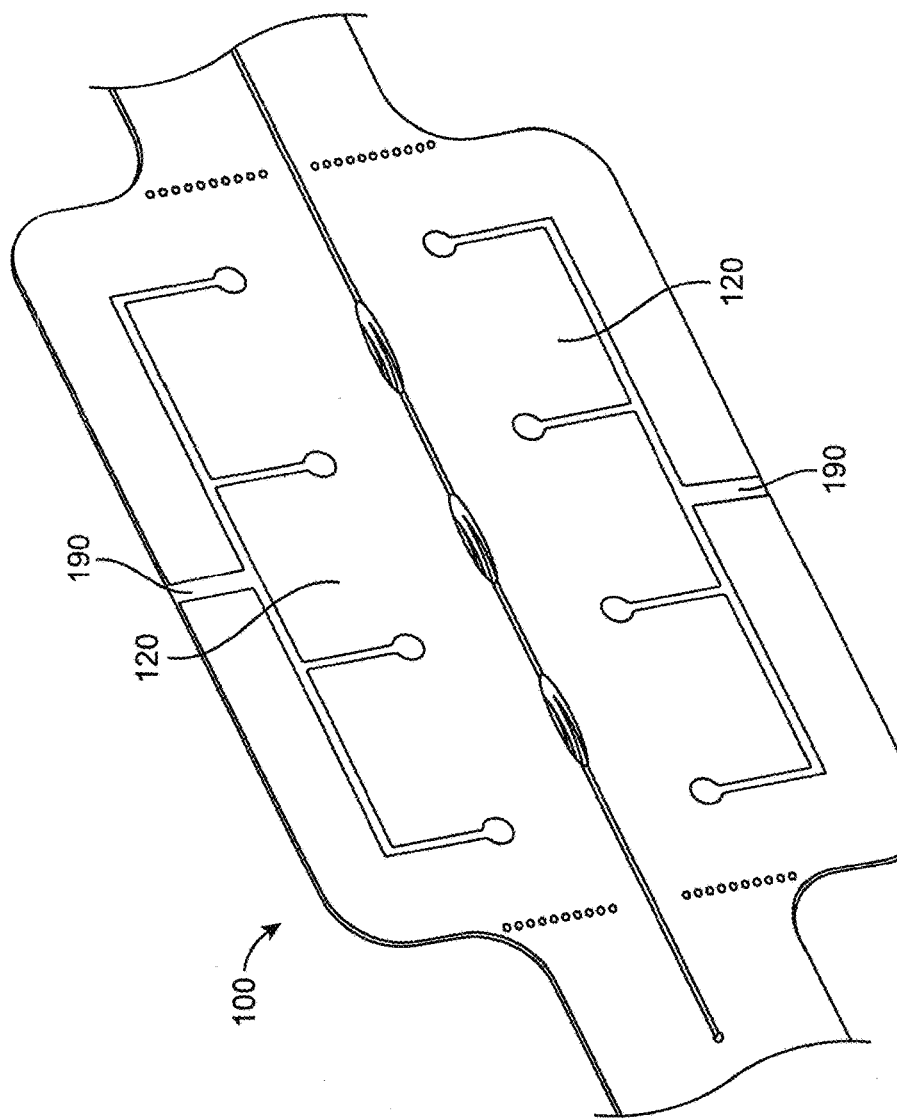
FIG. 14 is a perspective view from the underside of the surgical closure device of FIG. 9 showing an optional feature of utility capillaries.

FIG. 14 is a perspective view from the underside of the surgical closure device 100 of FIG. 9 showing an optional feature of utility capillaries 190 that may be included with any embodiment of the surgical closure device 100 described herein. The utility capillaries 190 may be used to help remove the surgical closure device 100 from the patient's skin after the incision has healed sufficiently. A solvent, such as acetone, can be injected into the capillaries 190 to help dissolve and loosen the adhesive 120 that adheres the closure device 100 to the skin. A solvent can also be applied through pores or holes in the surface of the surgical closure device 1100. Alternatively or in addition, pressurized, air or fluid can be infected into the capillaries 190 to help lift the surgical closure device 100 off of the skin surface.

Figure 15:
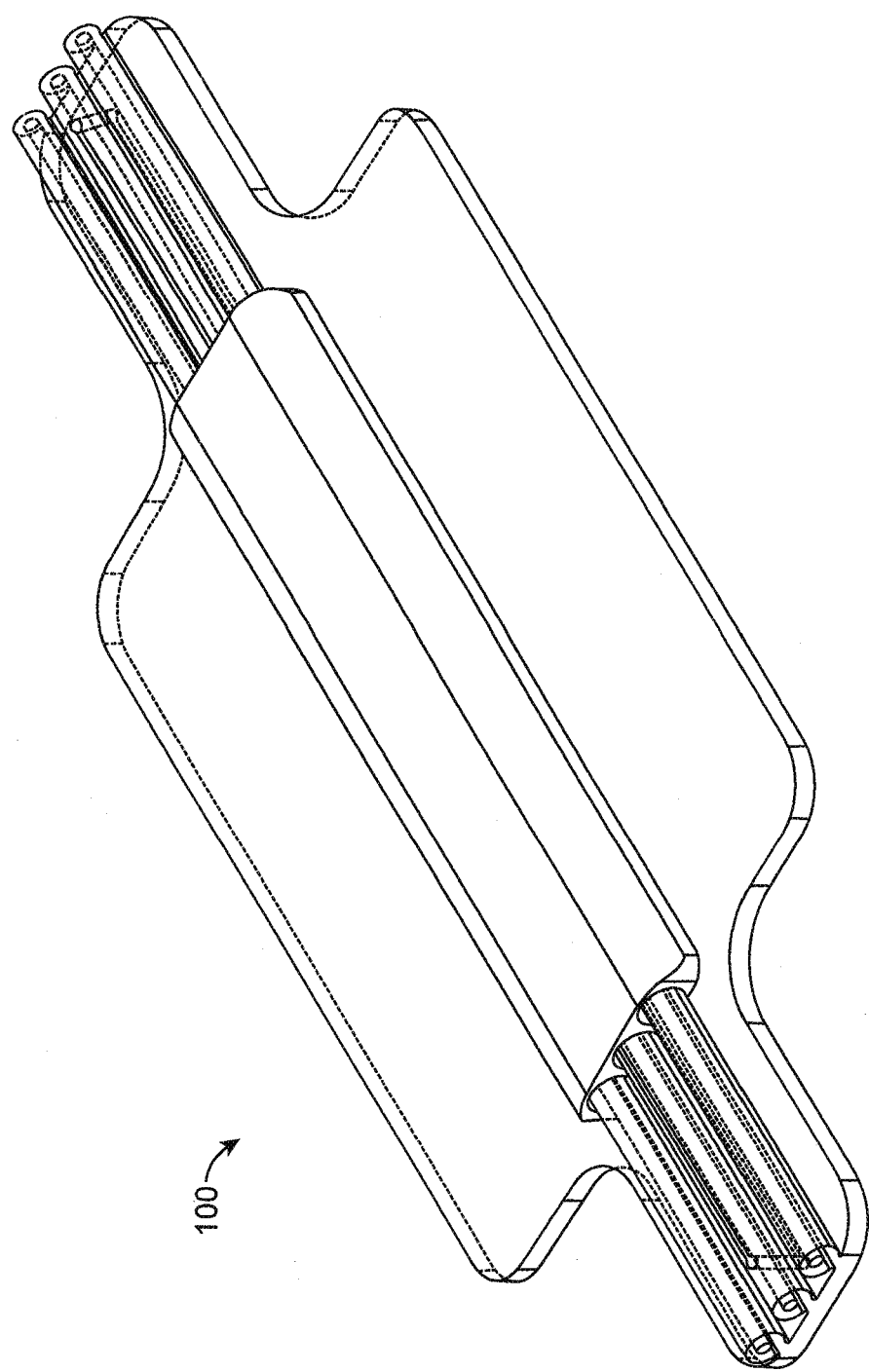
FIG. 15 shows another embodiment of the surgical closure device.

FIG. 15 shows another embodiment of the surgical closure device 100 having additional rails for more stable and secure attachment of the binder.

Figure 16:
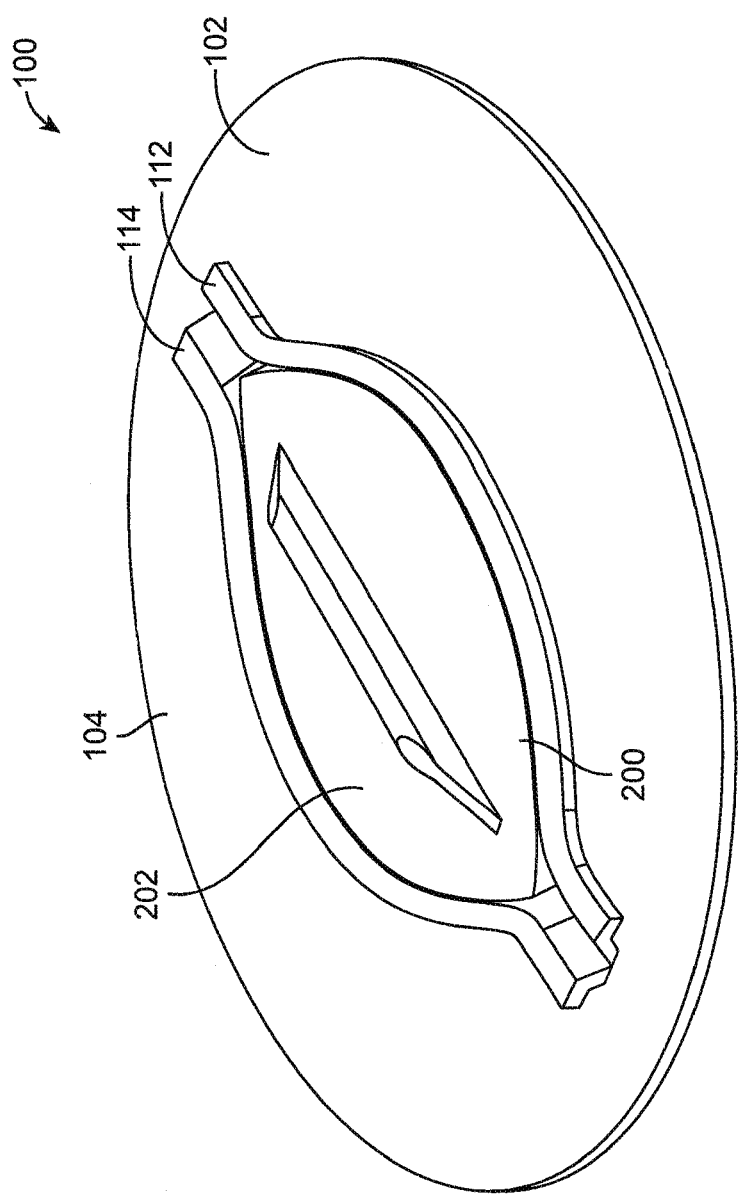
FIG. 16 is a perspective drawing of a surgical closure device for making a shaped incision in a patient's skin.
Figure 17:
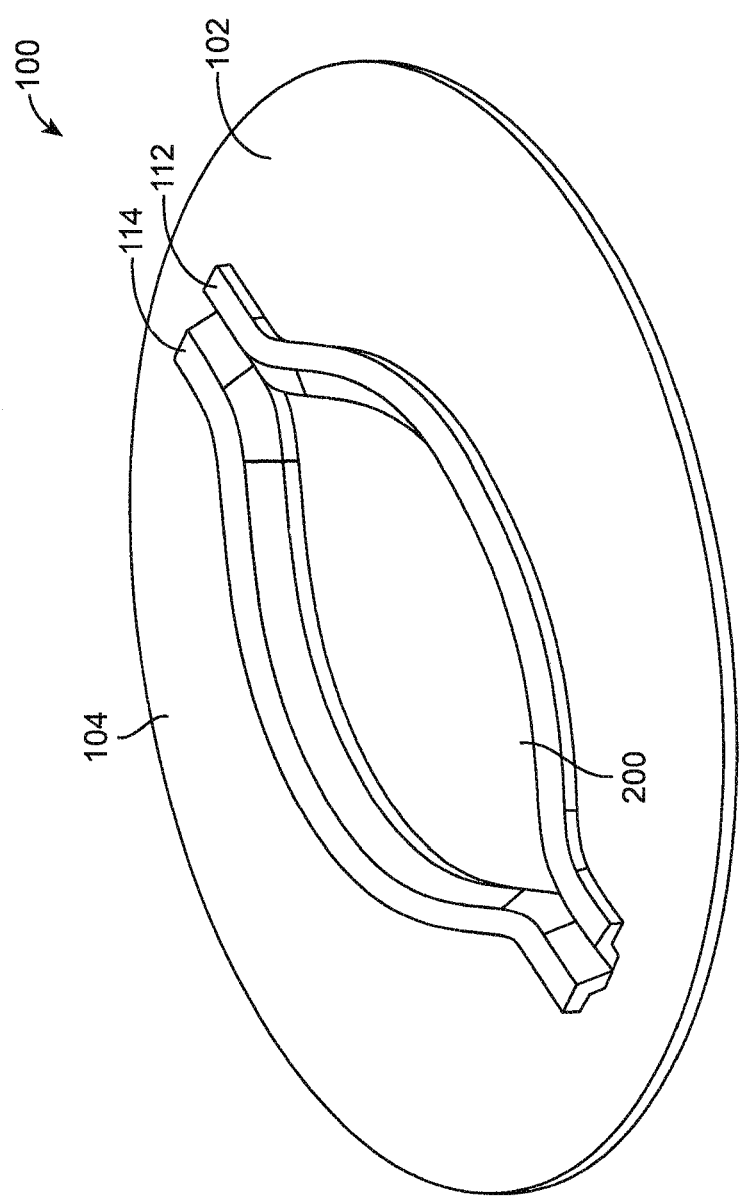
FIG. 17 shows the surgical closure device of FIG. 16 with the shaped insert removed.

FIG. 16 is a perspective drawing of a surgical closure device 100 for making and closing a shaped incision in a patient's skin. A simple device for making and closing a shaped incision in the patient's skin will be useful in a number of common medical procedures including nodule biopsy and removal of skin lesions and well as taking off skin excess in weight reduction procedures or cosmetic procedures. The surgical closure device 100 of FIG. 16 is quite similar to previously described embodiments except that there is a nonlinear shaped opening 200 between the first adhesion patch 102 and the second adhesion patch 104 that defines the shape of the incision. In one particularly preferred embodiment, the shaped opening 200 has the geometry of a rounded lozenge shape somewhat like the shape of an American football or a convex-convex lens. The first rail 112 and the second rail 114 follow the outline of the shaped opening 200. Preferably, the first and second adhesion patch 102, 104 are joined together beyond the ends of the shaped opening 200. Optionally, the opening 200 may be biased toward an open position or a closed position. A removable shaped insert 202 may be used to maintain the shape of the opening 200 during attachment of the surgical closure device 100 to the patient's skin. This is particularly important if the shaped opening 200 is biased toward a closed position. The removable shaped insert 202 may be also used as a guide for a scalpel to cut the skin around the inside of the shaped opening 200 or the shaped insert 202 may be removed before making the incision. FIG. 17 shows the surgical closure device 100 of FIG. 16 with the shaped insert 202 removed. The edges of the shaped opening 200 are preferably beveled at an angle (typically 45-90 degrees) to assist in holding a scalpel at the proper angle to cut out a wedge-shaped skin biopsy sample.

Figure 18:
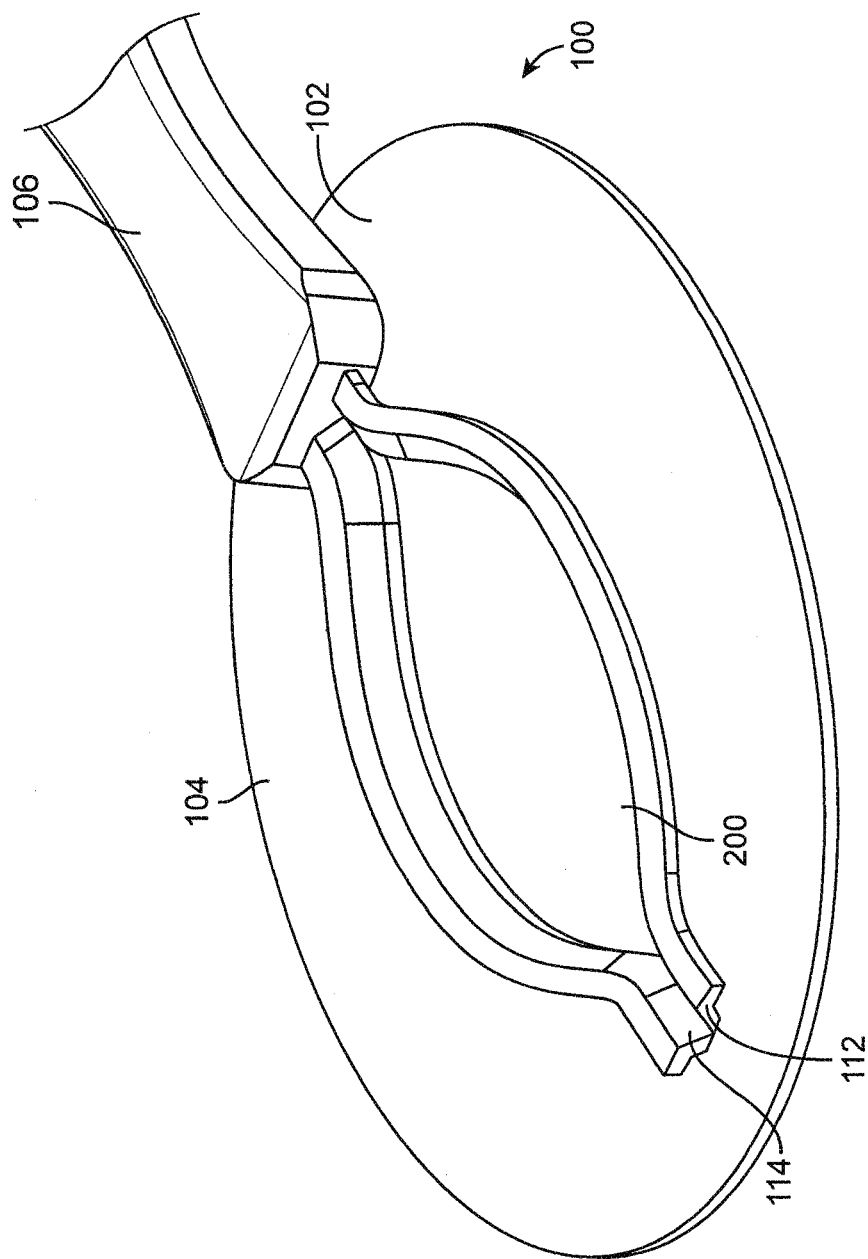
FIG. 18 shows the surgical closure device of FIG. 16 with the binder being applied.
Figure 19:
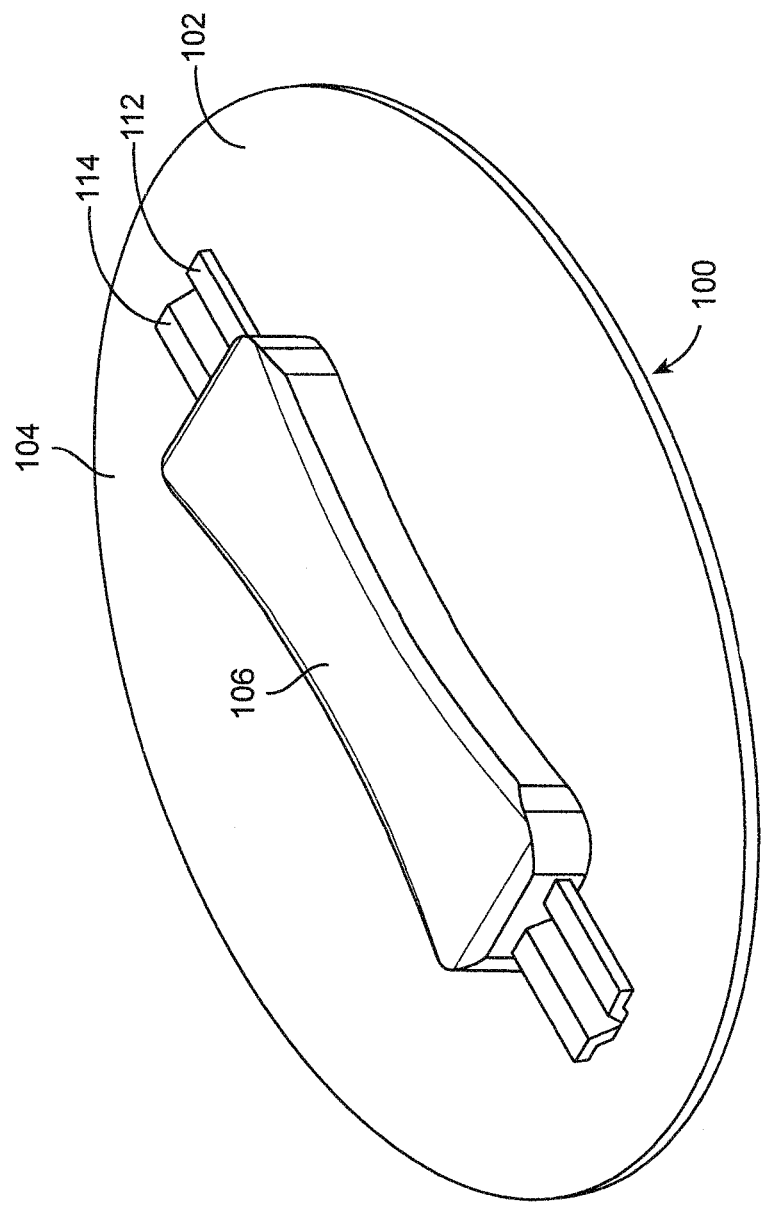
FIG. 19 shows the surgical closure device of FIG. 16 in a closed position.

FIG. 18 shows the surgical closure device 100 of FIG. 16 with the binder 106 being applied to close the incision. FIG. 19 shows the surgical closure device 100 of FIG. 16 in a closed position with the binder 106 in place.

For removal of large skin lesions using the surgical closure device 100 of FIG. 16, there may be a significant skin deficiency that must be made up for so it may be desirable to expand the skin peripheral to the shaped opening 200. Small cuts may be made in a pattern in the skin under and around the surgical closure device 100 so that the skin expands in a lattice pattern that will heal to cover up the skin deficiency. A special device with small skin blades in the desired pattern may be provided for performing this task. An inflatable balloon or other the like can be used to expand the skin prior to biopsy or excision of a lesion in order to make up for the skin deficiency.

Figure 20:
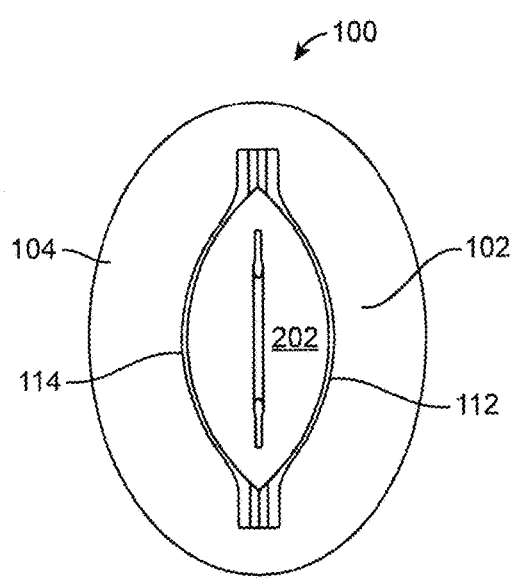
FIG. 20 shows another embodiment of a surgical closure device for making a shaped incision in a patient's skin.

FIG. 20 shows another embodiment of a surgical closure device 100 for making a shaped incision in a patient's skin. The surgical closure device 100 has a shaped opening 200 between the first adhesion patch 102 and the second adhesion patch 104 that defines the shape of the incision. A removable shaped insert 202 may be used to maintain the shape of the opening 200 during attachment of the surgical closure device 100 to the patient's skin. The first rail 112 and the second rail 114 follow the outline of the shaped opening 200.

Figure 21:
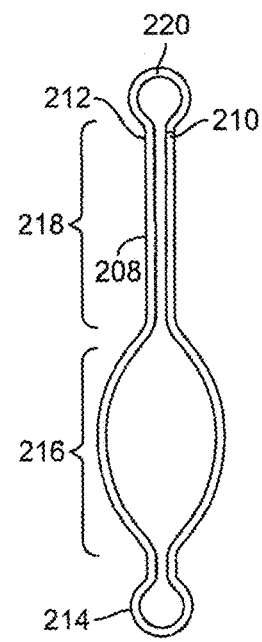
FIG. 21 shows a wire form for the surgical closure device of FIG. 20.
Figure 22:
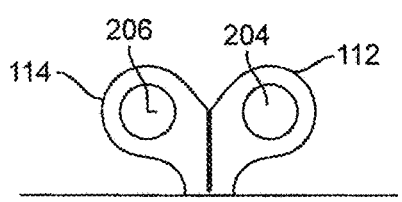
FIG. 22 shows a cross section of the rails of the surgical closure device of FIG. 20.
Figure 23:
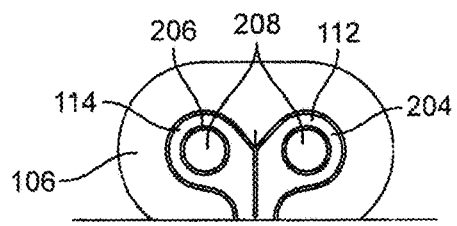
FIG. 23 shows a cross section of the rails of the surgical closure device of FIG. 20 with the wire form and binder in place.
Figure 24:
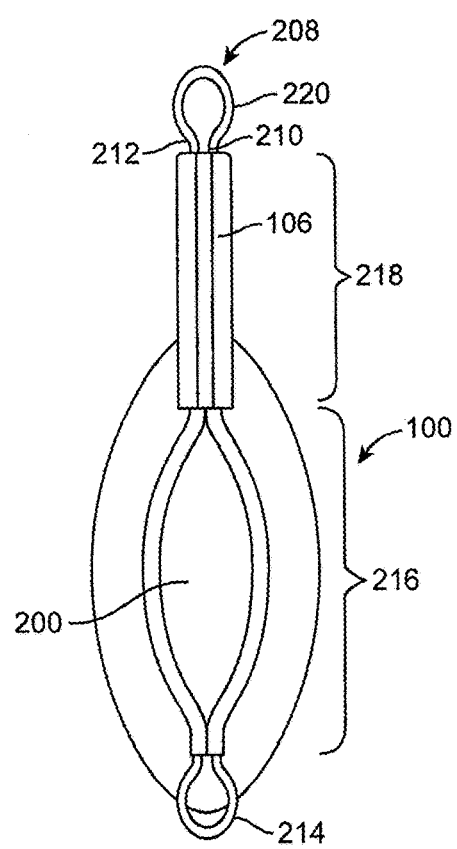
FIG. 24 shows the surgical closure device of FIG. 20 in an open position.
Figure 25:
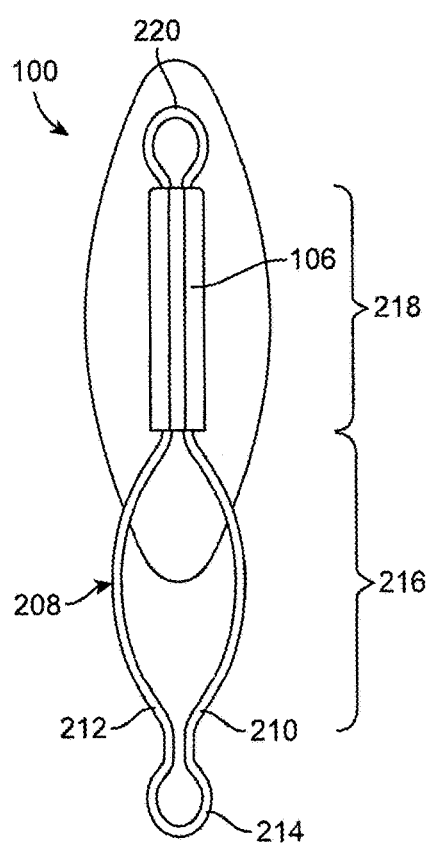
FIG. 25 shows the surgical closure device of FIG. 20 in a closed position.

A wire form 208, shown in FIG. 21, is provided for selectively biasing the surgical closure device 100 toward the open position or the closed position. The wire form 208 has a first leg 210 and a second leg 212 joined together at one end by a first bend 214. The wire form 208 has an open section 216 where the first leg 210 and the second leg 212 are curved outward in a curve similar to the shaped opening 200 between the first adhesion patch 102 and the second adhesion patch 104 and a closed section 218 where the first leg 210 and the second leg 212 are straight, parallel and close together. The wire form 208 is preferably formed from a metal wire, such as a stainless steel, cobalt-chromium or nickel-titanium alloy. Optionally, the first leg 210 and the second leg 212 of the wire form 208 may have a low friction coating, such as PTFE. As shown in cross section in FIG. 22, a first lumen 204 extends longitudinally through the first rail 112 and a second lumen 206 extends longitudinally through the second rail 114 for receiving the first leg 210 and the second leg 212 of the spine wire 208, respectively. FIG. 23 shows a cross section of the first and second rails 112, 114 of the surgical closure device 100 of FIG. 20 with the wire form 208 and the binder 106 in place. After insertion through the first lumen 204 and the second lumen 206, the ends of the first leg 210 and the second leg 212 are joined together, for example by welding, brazing or soldering, to form a second bend 220 located at the other end of the wire form 208, as shown in FIGS. 24 and 25. The first and second bends 214, 220 are preferably shaped to form tabs or handles for easy gripping.

FIG. 24 shows the fully assembled surgical closure device 100 in an open position. The wire form 208 is positioned so that the outwardly curved, open section 216 of the first leg 210 and the second leg 212 surrounds the shaped opening 200, thereby biasing the device 100 toward the open position. Optionally, the binder 106 may be attached to the wire form 208 so that it is positioned around the closed section 218 of the wire form 208.

FIG. 25 shows the surgical closure device 100 of FIG. 24 in a closed position. The wire form 208 has been slid longitudinally to a position where the straight, closed section 218 of the first leg 210 and the second leg 212 surrounds the shaped opening 200, thereby biasing the device 100 toward the closed position. Because it is attached to the wire form 208, the binder 106 will automatically slide over the first and second rails 112, 114 to secure the surgical closure device 100 in the closed position. Alternatively, the binder 106 can be applied in a separate step. As another alternative, the wire form 208 may be constructed to be rigid enough to hold the surgical closure device 100 in a closed position without the binder 106.

Optionally, the open section 216 of the wire form 208 may be trimmed of or broken off after the surgical closure device 100 is in the closed position. Optionally, a clip, staple or other fastener may be applied to the wire form 208 prior to cutting to keep the first leg 210 and the second leg 212 from splaying apart once the open section 216 is removed.

Figure 26:
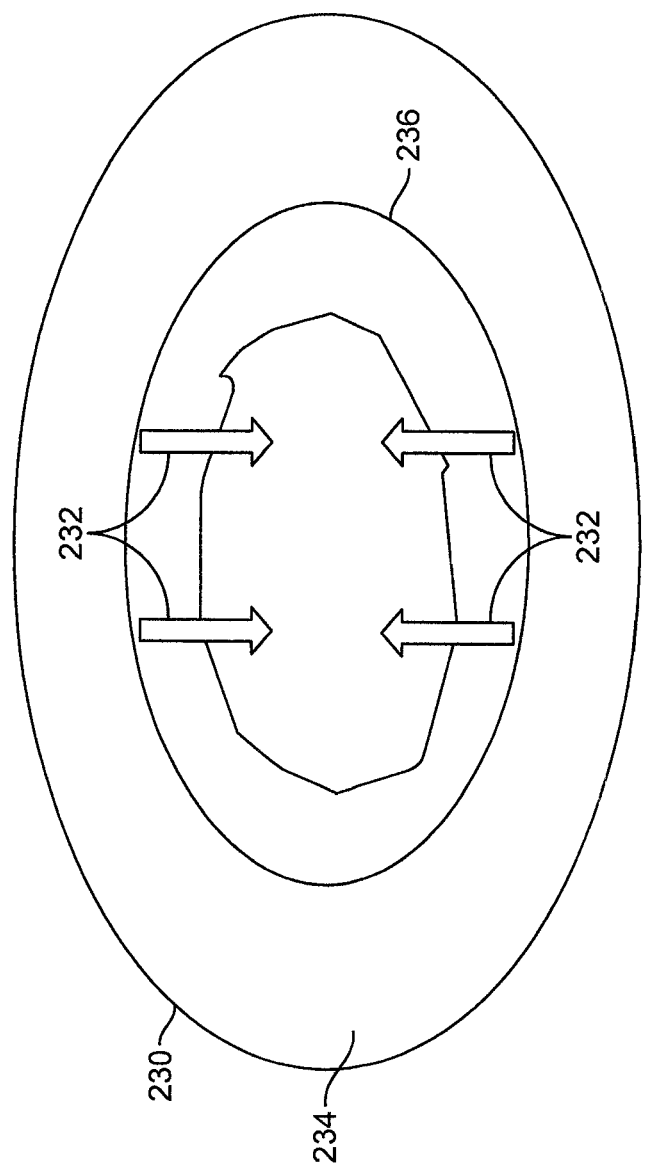
FIG. 26 is a schematic drawing of a surgical closure device for applying a continuous closing force to promote healing of a large skin incision.

In an alternative configuration, the wire form 208 may be made of a malleable material, such as annealed aluminum or copper, so that the surgical closure device 100 can be manually formed into an open or closed position. In addition, a malleable wire form 208 may be used to form the surgical closure device 100 to fit a nonlinear incision or preexisting wound. FIG. 26 is a schematic drawing of a surgical closure device 230 for applying a continuous closing force to promote healing of a large skin incision. After removal of a large biopsy sample or a large skin lesion, there may be a significant skin deficit that needs to be made up before complete healing of the incision can occur. A chronic or continuous closing force can help to promote closure and healing of the incision. A very pliable and flexible adhesion patch 234 with an opening 236 in the middle is applied to the patient's skin surrounding the incision or lesion. The arrows 232 indicate how the closing force is applied to the adhesion patch 234 around the opening 236 to promote closure of the incision.

FIGS. 27A, 27B and 27C show various configurations of tension members 240 for applying a continuous closing force in the surgical closure device 230 of FIG. 26. FIG. 27A shows a tension member 240 that has an elongated body 248 with barbs 246 along the sides of the tension member 240. A first end of the tension member 240 is attached to an anchor member 242 that is permanently or removably attached to the adhesion patch 234. The elongated body 248 of the tension member 240 passes through a catch 244 that is also permanently or removably attached to the adhesion patch 234. The catch 244 cooperates with the barbs 248 along the sides of the tension member 240 to create a type of ratchet mechanism for selectively tightening the tension member 240. The elongated body 248 of the tension member 240 is preferably made of an elastomeric material that will provide the desired range of tension. The tension member 240 of FIG. 27B is similar to that of FIG. 27A, except that the barbs 246 have been replaced with bumps or nubs 250 along the sides of the tension member 240. The tension member 240 of FIG. 27C has waves or undulations 252 that interact with the catch 244 to create a tension adjustment mechanism. The waves or undulations 252 also turn the elongated body 248 into a spring member, therefore the undulated elongated body 248 can be constructed of a metal wire or a less flexible polymer as an alternative to the elastomeric material of the other embodiments. The waves or undulations 252 may be planar or they may be formed in a helix or other three-dimensional shape.

Figure 28:
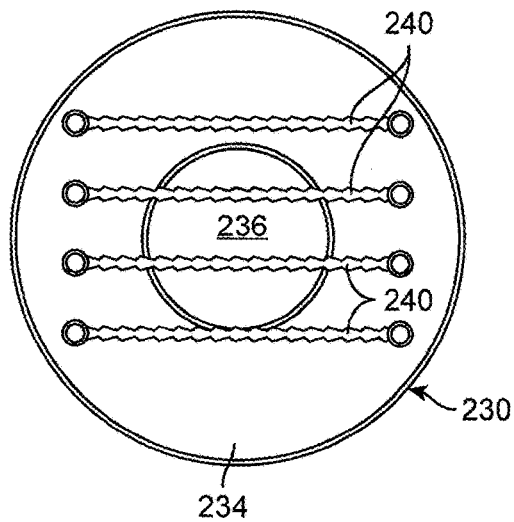
FIG. 28 shows a surgical closure device for applying a unidirectional closing force.
Figure 29:
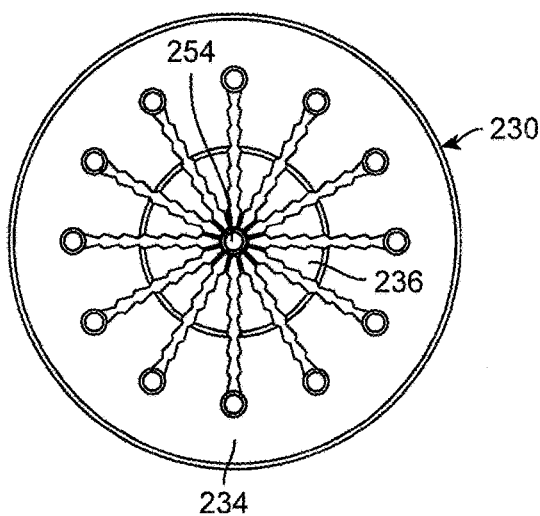
FIG. 29 shows a surgical closure device for applying a radial closing force.

FIG. 28 shows a surgical closure device 230 configured for applying a unidirectional closing force. A plurality of tension members 240 are arranged approximately parallel with one another across the opening 236 of the adhesion patch 234. Tension in each of the tension members 240 can be individually adjusted. FIG. 29 shows a surgical closure device 230 configured for applying a radial closing force. A plurality of tension members 240 radiate from a common attachment point 254 approximately over the center of the opening 236 in the adhesion patch 234. Alternatively, a plurality of tension members 240 can be arranged across the diameter of the opening 236 in the adhesion patch 234. Tension in each of the tension members 240 can be individually adjusted.

Figure 30:
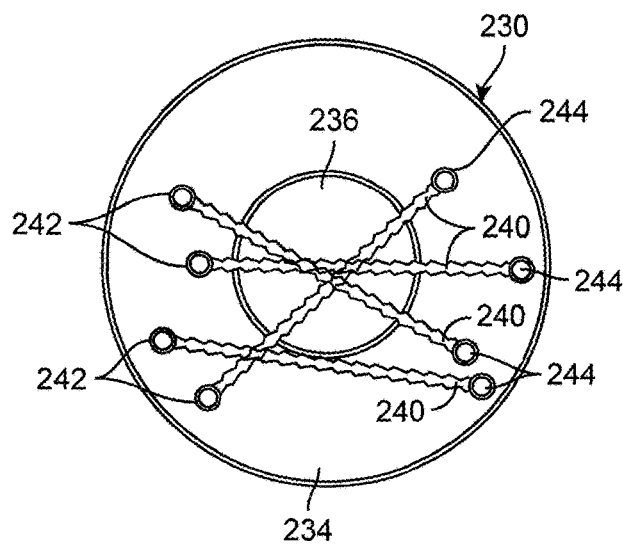
FIG. 30 shows a surgical closure device with tension members in a random or ad hoc configuration.

FIG. 30 shows a surgical closure device 230 with tension members 240 in a random or ad hoc configuration. This arrangement is useful for tailoring the surgical closure device 230 to irregularly shaped incisions or lesions. The positions of each anchor member 242 and catch 244, as well as the tension in each of the tension members 240, may be individually adjustable.

Figure 31:
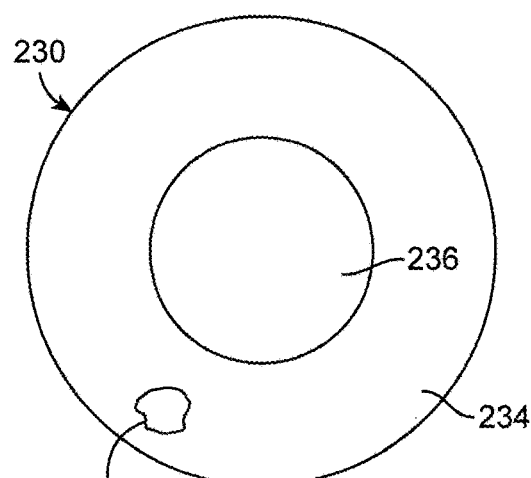
FIG. 31 shows a surgical closure device that allows application of the tension members in any desired pattern.

FIG. 31 shows a surgical closure device 230 that allows application of the tension members 240 in any desired pattern. The flexible adhesion patch 234 is constructed so that the tension members 240 can be easily attached at any point on the surface of the patch 234.

Figure 32:
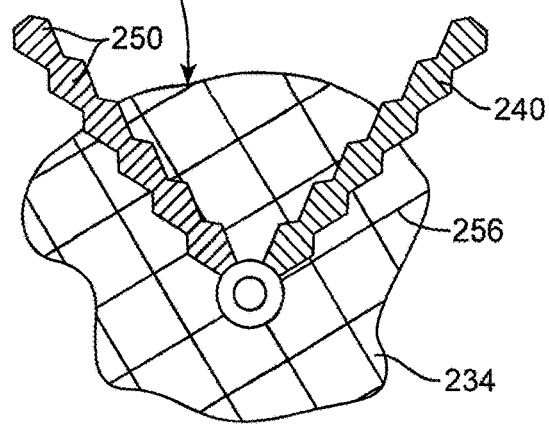
FIG. 32 is a detail drawing of one embodiment of the surgical closure device of FIG. 31.

FIG. 32 is a detail drawing of one embodiment of the surgical closure device 230 of FIG. 31 wherein the surface of the adhesion patch 234 is constructed of a mesh material 256. A tension member 240 with barbs 250 is being inserted through the mesh material 256 and tightened to apply tension to the surgical closure device 230 in the desired pattern. The mesh material 256 performs the functions of the anchor member 242 and/or the catch 244 described above.

Figure 33:
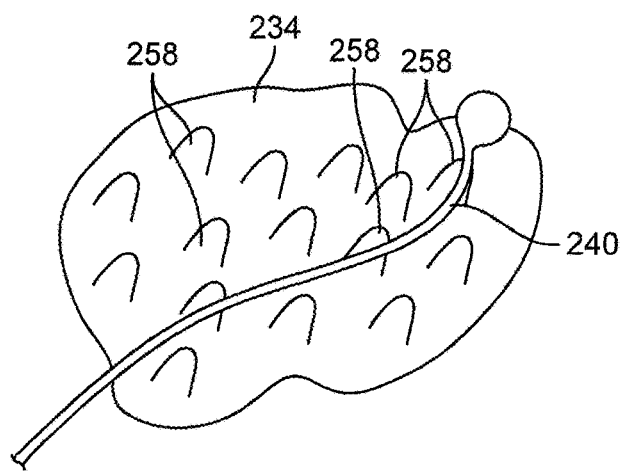
FIG. 33 is a detail drawing of another embodiment of the surgical closure device of FIG. 31.

FIG. 33 is a detail drawing of another embodiment of the surgical closure device 230 of FIG. 31 wherein the adhesion patch 234 is constructed with a multiplicity of loops 258 on its surface. A tension member 240 is being inserted through the loops 258 and tightened to apply tension to the surgical closure device 230 in the desired pattern. The loops 258 perform the functions of the anchor member 242 and/or the catch 244 described above.

Figure 34:
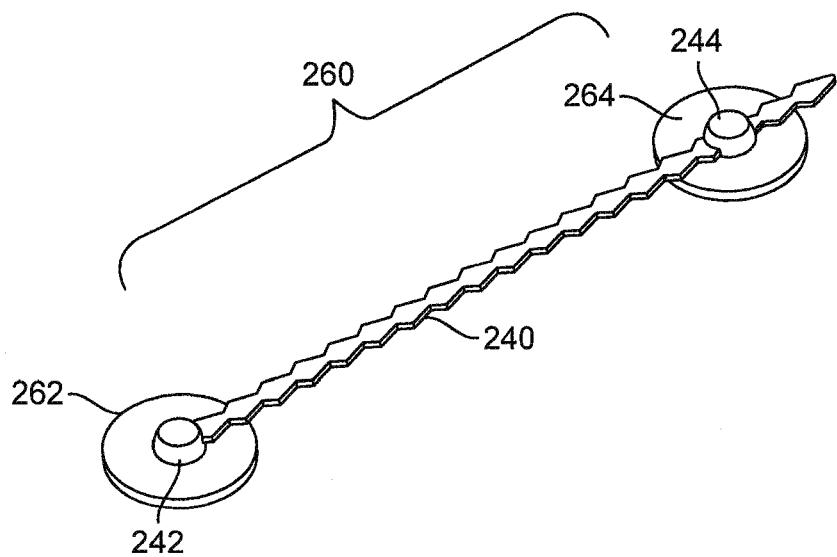
FIG. 34 shows a surgical closure device that uses independent strap patches for attachment of the tension members.

FIG. 34 shows a surgical closure device 260 that uses independent strap adhesion patches 262, 264 for attachment of the tension members 240. The anchor member 242 is attached to a first adhesion patch 262 and the catch 244 is attached to a second adhesion patch 264. This allows even greater flexibility for arranging the tension members 240 in any desired pattern.

Figure 35:
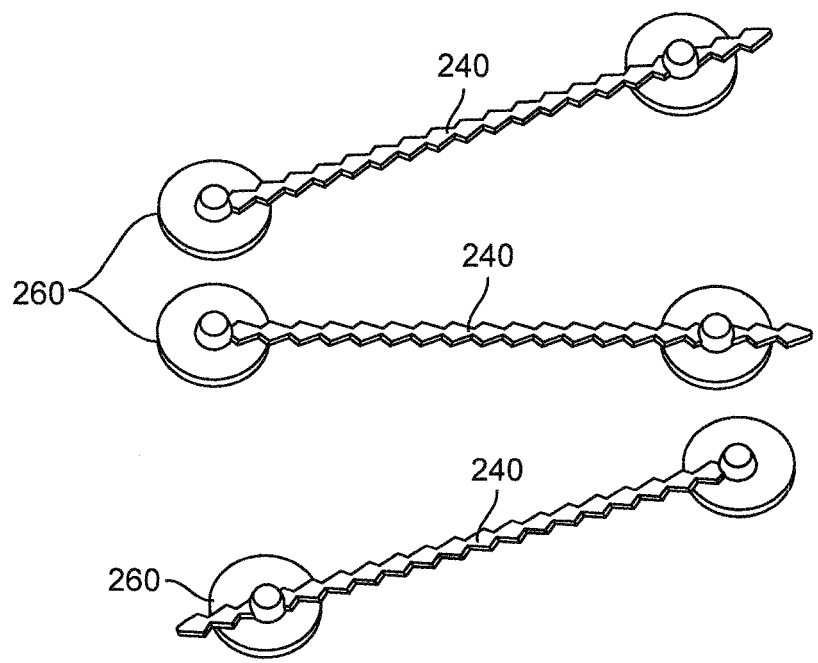
FIG. 35 shows three of the surgical closure devices of FIG. 34 applied to a patient.

FIG. 35 shows three of the surgical closure devices 260 of FIG. 34 applied to a patient. In this example, the tension members 240 are arranged approximately parallel to one another to provide a unidirectional closing force. Many other patterns are also possible.

Figure 36:
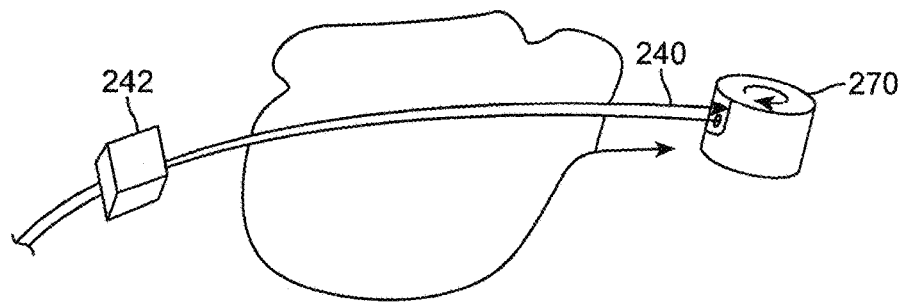
FIG. 36 shows a tension member that utilizes a constant force spring and an anchor member.

FIG. 36 shows a tension member 240 that utilizes a constant force spring 270 and an anchor member 242. The constant force spring 270 has the advantage that it provides approximately constant force no matter what the displacement of the spring is. Thus, the tension in the tension member 240 would not need to be readjusted as the wound begins to close and heal up.

Figure 37:
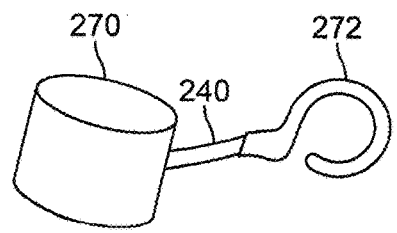
FIG. 37 shows a tension member with the constant force spring retracted.

FIG. 37 shows a tension member 240 with the constant force spring 270 retracted. A hook 272 is attached at the end of the constant force spring 270.

Figure 38:
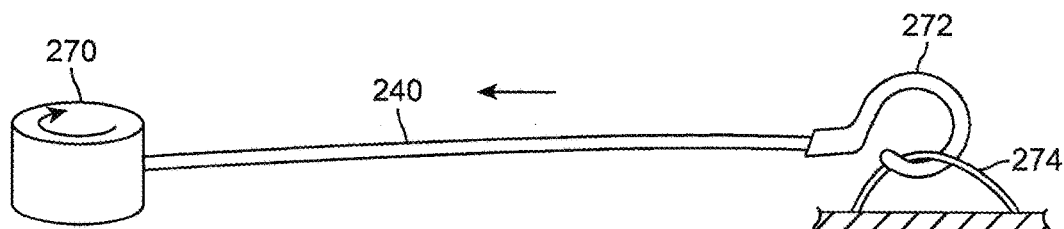
FIG. 38 shows a tension member with the constant force spring extended.

FIG. 38 shows the tension member 240 with the constant force spring 270 extended. The hook 272 is hooked through a loop 274, which may be attached to an anchor member or attached directly to an adhesion patch.

Figure 39:
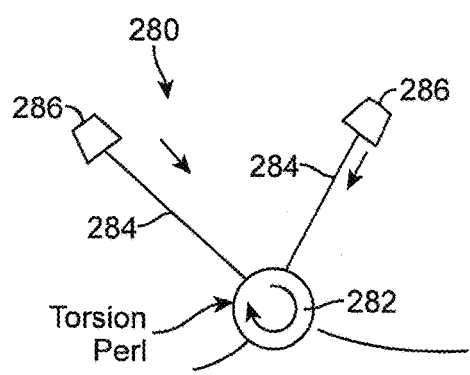
FIG. 39 shows a multidirectional tension device that utilizes a spring reel.

FIG. 39 shows a multidirectional tension device 280 that utilizes a spring reel 282. A multiplicity of radial tension members 284 extend radially from the spring reel 282 and connect to a like number of anchor members 286.

Figure 40A:
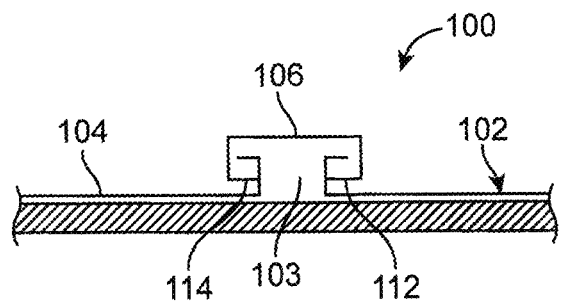
FIGS. 40A, 40B and 40C illustrate a surgical closure device configured for applying adjustable compression to an incision, shown in cross section.
Figure 40B:
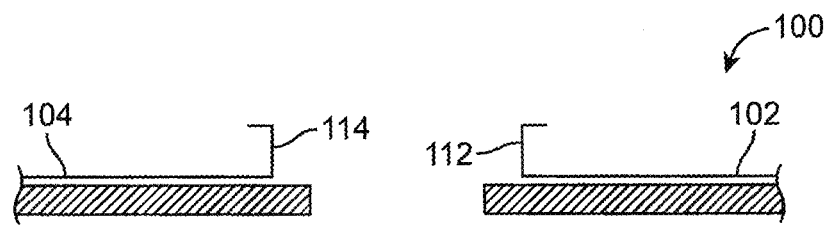
Figure 40C:
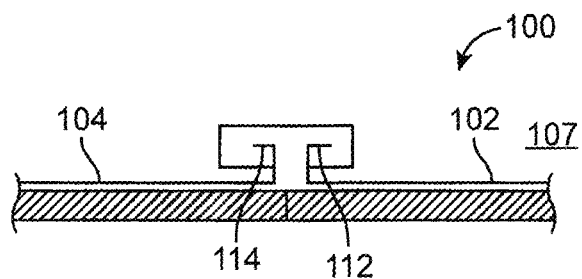

In some cases it is advantageous to apply a controlled amount of compression to an incision after closure in order to encourage healing. FIGS. 40A, 40B and 40C illustrate a surgical closure device 100 configured for applying adjustable compression to an incision. FIG. 40 A shows a cross section of the surgical closure device 100 applied to a patient's skin. The surgical closure device 100 includes a first adhesion patch 102, a second adhesion patch 104 and a first channel-shaped binder 106 that is configured to slide over the first and second track or rail 112, 114 to hold the first and second adhesion patch 102, 104 together with a controlled-width gap 103 in between.

An incision is made between the first adhesion patch 102 and second adhesion patch 104 and the incision is opened for performing a surgical operation, as shown in FIG. 40B. It should be noted that the edges of the incision extend past the edges of the first and second rails 112, 114.

FIG. 40C shows the incision after closure with the surgical closure device 100. A second channel-shaped binder 107 has been slid over the first and second rails 112, 114 to hold the first and second adhesion patch 102, 104 together. The second channel-shaped binder 107 has a channel width that is less than the channel width of the first channel-shaped binder 106, which creates a controlled amount of compression at the incision line.

Figure 41:
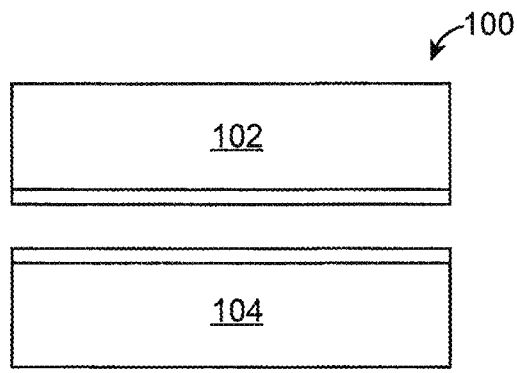
FIG. 41 illustrates a surgical closure device where the first and second adhesion patches separate completely when in an open position.

FIG. 41 illustrates a surgical closure device 100 where the first and second adhesion patches 102, 104 separate completely when in an open position. This configuration is advantageous when a very large surgical access is required for performing an operation. Markings, detents or other alignment mechanisms would be included to assure proper alignment and apposition of the incision during closure.

Figure 42:
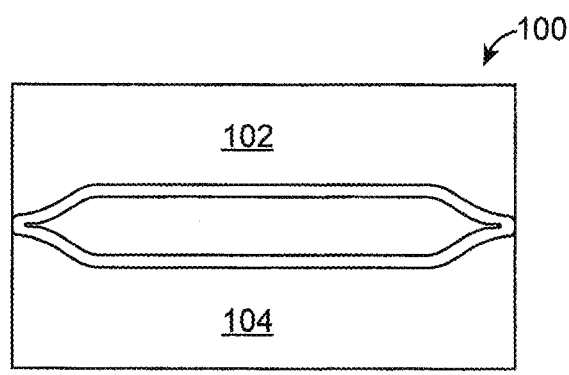
FIG. 42 illustrates a surgical closure device where the first and second adhesion patches are permanently attached at both ends.

FIG. 42 illustrates a surgical closure device 100 where the first and second adhesion patches 102, 104 are permanently attached at both ends. This configuration has the advantage that the incision will be automatically aligned in proper apposition when the incision is closed. Alternatively, just one end of the first and second adhesion patches 102, 104 can be permanently attached.

Figure 43:
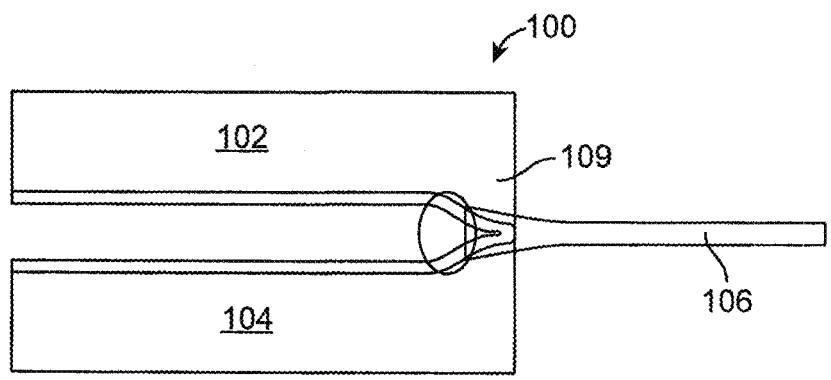
FIG. 43 illustrates a surgical closure device with a binder having a Y-shaped end to facilitate closure of the device.

FIG. 43 illustrates a surgical closure device 100 with a binder 106 having a Y-shaped end 109 to facilitate closure of the device. The tapered entry of the Y-shaped end 109 on the binder 106 reduces the force required for applying the binder 106 to close the incision.

Figure 44:
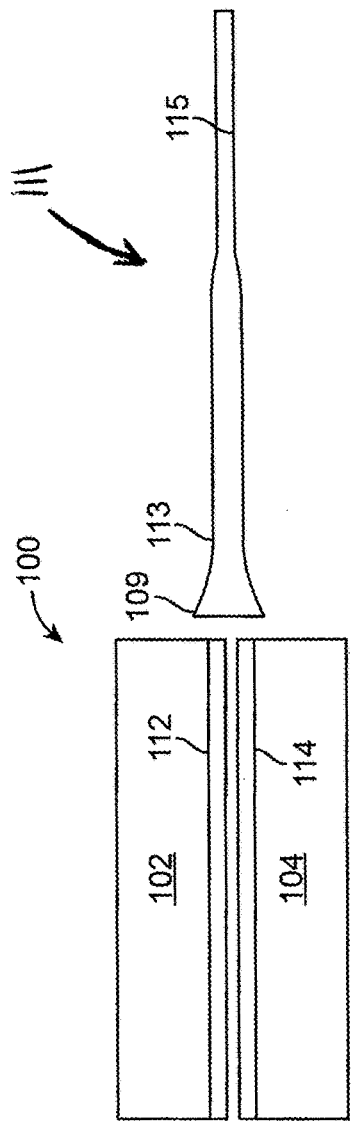
FIG. 44 illustrates a surgical closure device with a binder configured for sequential closure of the device.

FIG. 44 illustrates a surgical closure device 100 with a binder 111 configured for sequential closure of the device. This configuration facilitates the method described above in FIGS. 40A, 40B and 40C by integrating the first binder 106 and the second binder 107 into a single component. Optionally, the binder 111 may have a tapered Y-shaped end 109 as in the embodiment previously described. After the surgical operation is completed, the incision is closed by sliding the first part of the binder 113 over the first and second rails 112, 114, then sliding the second, narrower part of the binder 115 over the first and second rails 112, 114. The second, narrower part of the binder 115 may be configured to provide a. controlled amount of compression to the incision after closure.

Figure 45:
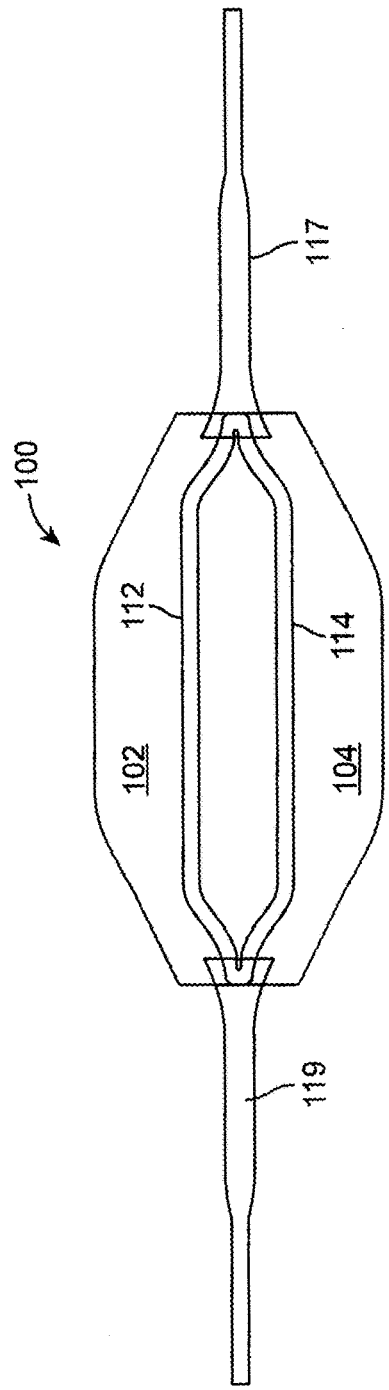
FIG. 45 illustrates a surgical closure device with a first and second binder configured for sequential closure of the device.

FIG. 45 illustrates a surgical closure device 100 with a first and second binder 117, 119 configured for sequential closure of the device. The second binder 119 is narrower than the first binder 117. The surgical closure device 100 is closed sequentially by sliding the first binder 117 over the first and second rails 112, 114 from one end, then sliding the second, narrower binder 119 over the first and second rails 112, 114 from the opposite end while backing the first binder 117 off. The advantage of sequential closing is reduced force and shear by closing the surgical closure device 100 in a stepwise fashion. Multiple steps may be used, optionally including binders with channels wider even than the first binder.

Figure 46:
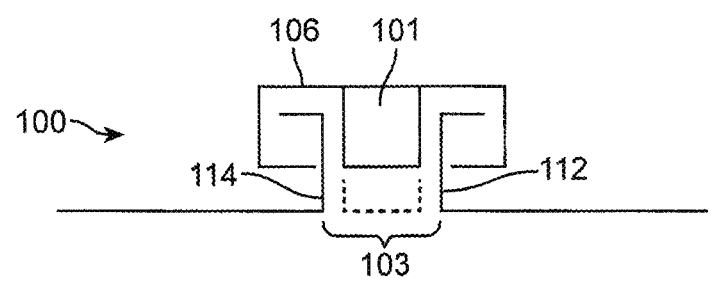
FIG. 46 is a cross section of a surgical closure device with a binder having a middle ridge for precise spacing of the first and second rails.

FIG. 46 is a cross section of a surgical closure device 100 with a binder 106 having a middle ridge 101 for precise spacing of the first and second rails 112, 114. This configuration is advantageous for performing the method described above in FIGS. 40A, 40B and 40C because it holds the first and second rails 112, 114 in careful alignment with a controlled gap 103 in between.

Figure 47:
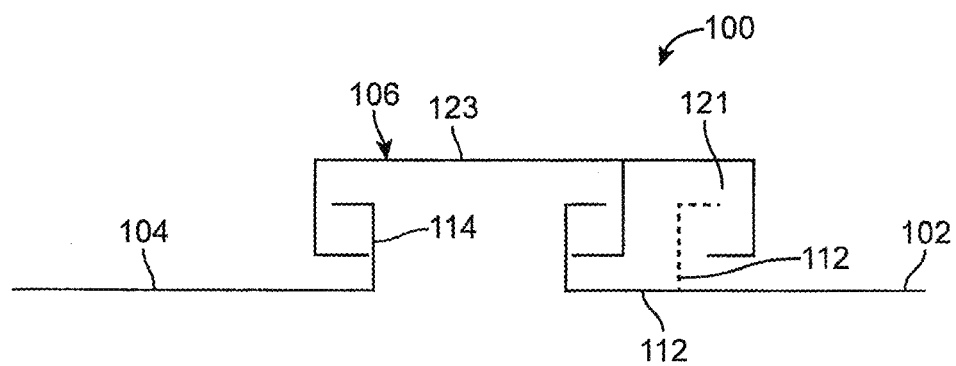
FIG. 47 is a cross section of a surgical closure device with a binder having a first and a second channel for applying adjustable compression to an incision.

FIG. 47 is a cross section of a surgical closure device 100 with a binder 106 having a first channel 121 and a narrower, second channel 123 for applying adjustable compression to an incision. This configuration is advantageous for performing the method described above in FIGS. 40A, 40B and 40C. The surgical closure device 100 can be initially applied to the patient with the first channel 121 positioned over the first and second rails 112, 114. After the surgery is completed, the binder 106 can be reapplied with the narrower, second channel 123 positioned over the first and second rails 112, 114 to apply a controlled amount of compression to the incision.

Figure 48:
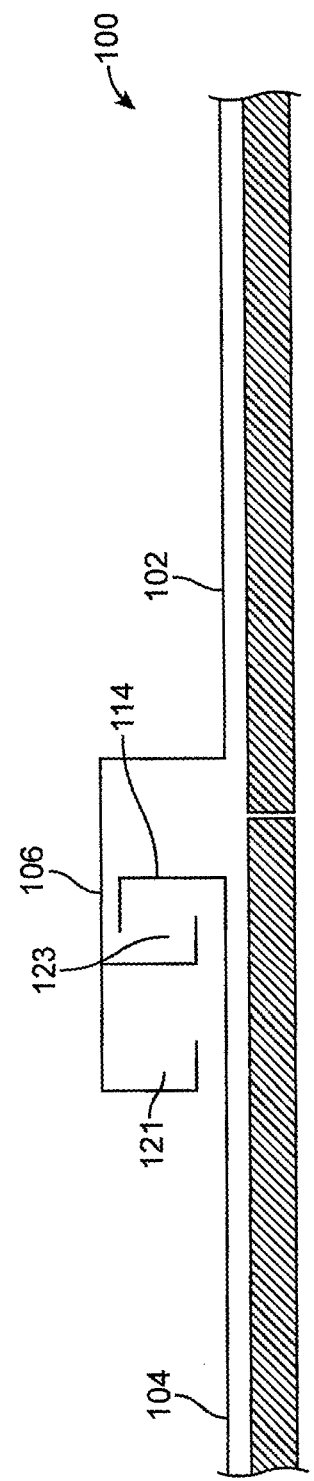
FIG. 48 is a cross section of a surgical closure device with a binder integrated into one of the adhesion patches.

FIG. 48 is a cross section of a surgical closure device 100 with a binder 106 integrated into one of the adhesion patches. Like the previously described embodiment, the binder 106 has a first channel 121 and a narrower, second channel 123 for applying adjustable compression to an incision. Multiple widths of channels are also possible. Closure of the surgical closure device 100 requires a slight lifting of the binder 106 to place it over the single rail 114 on the opposite side.

Figure 50:
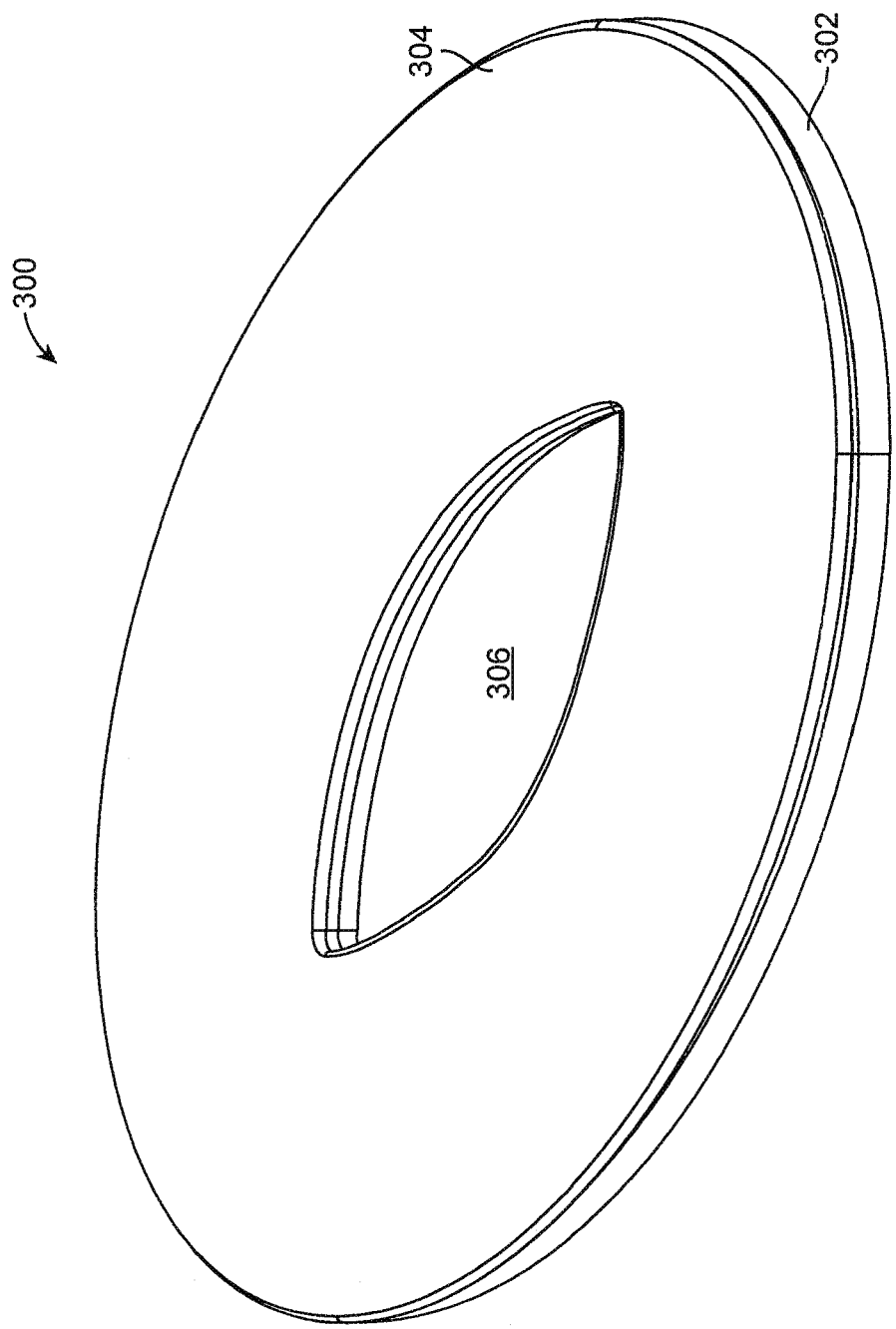
FIG. 50 is an assembly drawing of a surgical closure device that uses compression to apply a continuous closing force to help promote closure and healing of the incision.

FIGS. 50-54 illustrate an embodiment of the surgical closure device 300 that uses compression, rather than tension, to apply a chronic or continuous closing force to help promote closure and healing of the incision. This is particularly useful for large incisions and/or incisions where a portion of the skin and tissue has been removed, for example a nodule biopsy. FIG. 50 is an assembly drawing of the surgical closure device 300. The surgical closure device 300 has two main parts: an adhesive patch 302 that attaches to the patient's skin and a retainer 304 that is used to hold the adhesive patch 302 in a compressed state while it is being applied to the patient's skin.

Figure 51:
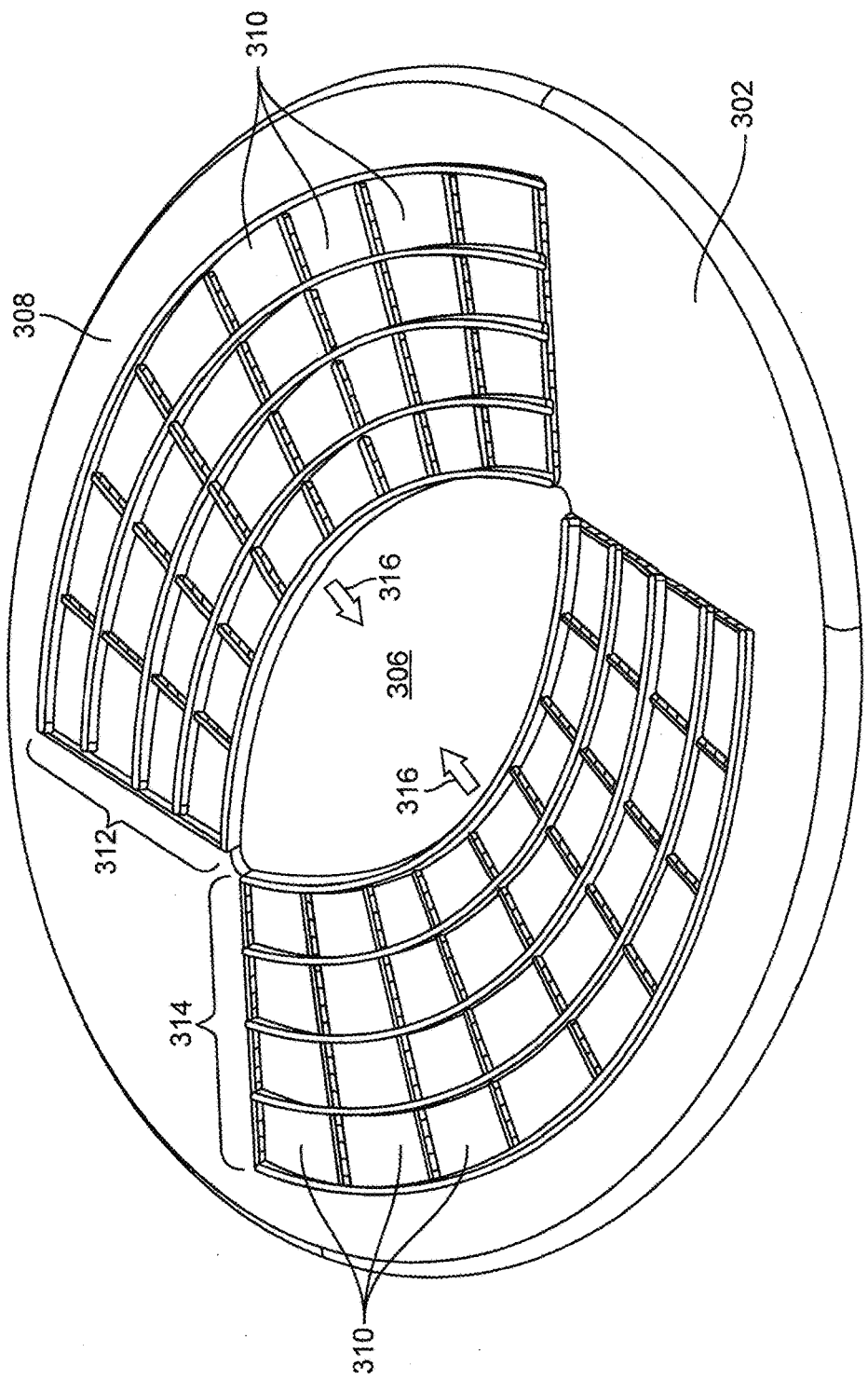
FIG. 51 shows the adhesive patch of the surgical closure device of FIG. 50.

The adhesive patch 302, which is shown by itself in FIG. 51, has a central opening 306 and a peripheral ring 308. The central opening 306 may be lozenge shaped, as in the example shown, or it may be circular, oval or another desired shape. The adhesive patch 302 surrounding the central opening 306 is made from a flexible, elastic material, whereas the peripheral ring 308 is made from a material that has a higher tensile strength in order to resist expansion. Between the central opening 306 and the peripheral ring 308, the surgical closure device 300 has a grid 312, 314 of expansion cells 310 attached to the adhesive patch 302. The expansion cells 310 in their natural state have a tendency to expand, however because they are constrained by the peripheral ring 308, the expansion of the cells 310 causes the central opening 306 to close. For a lozenge-shaped central opening 306, as in the example shown, it is advantageous to arrange the grid of expansion cells 310 in two sections 312, 314, one on either side of the opening 306, so that the inward expansion of the expansion cells 310 will be in the direction of the arrows 316.

Figure 52:
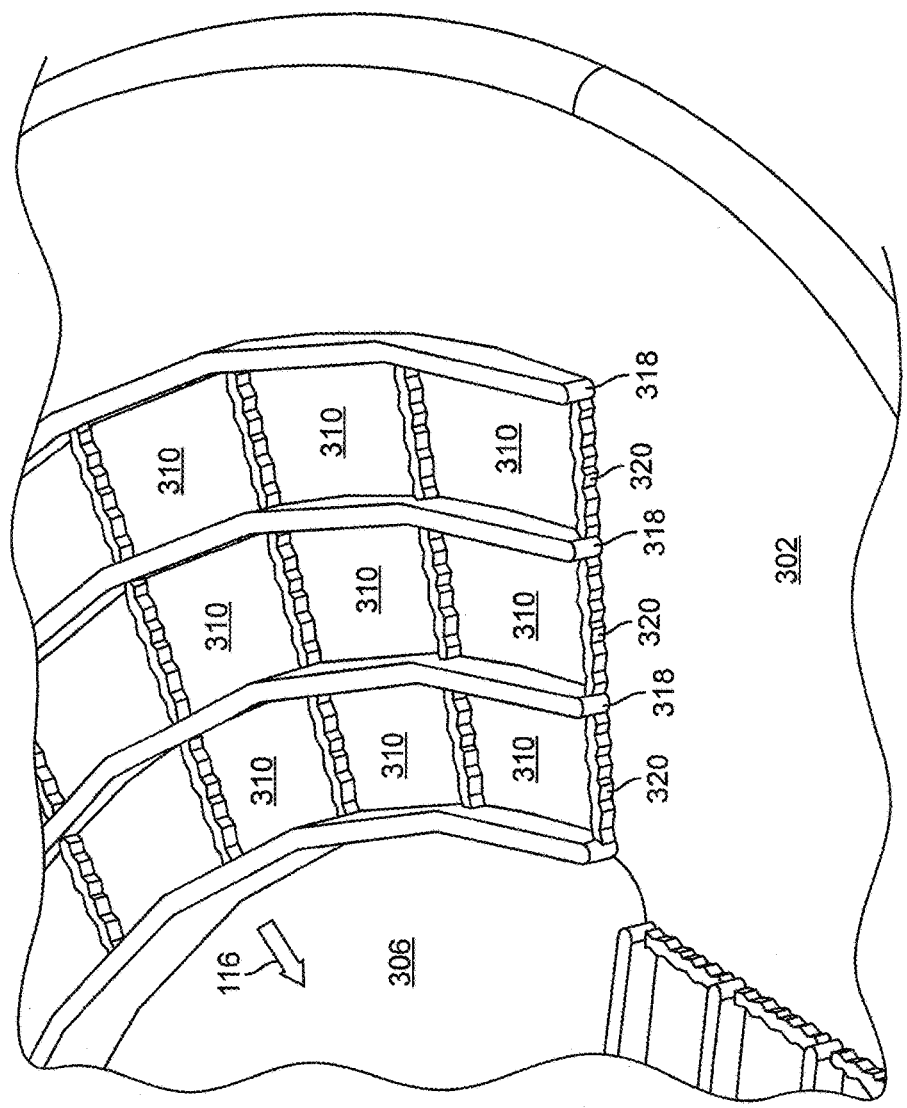
FIG. 52 shows an enlarged view of the expansion cells of the surgical closure device of FIG. 50.

FIG. 52 shows an enlarged view of an exemplary construction of the expansion cells 310. A plurality of circumferentially-oriented arcuate ribs 318 are attached to the adhesive patch 302 on both sides of the opening 306. Positioned between the ribs 318 are a plurality of compression spring members 320, which are biased to push apart the adjacent ribs 318. Since the peripheral ring 308 resists expansion, the net effect of the compression spring members 320 is to urge the central opening 306 toward a closed position, as indicated by the arrow 316. The compression spring members 320 may be metal compression springs, e.g. stainless steel or a nickel-titanium alloy, elastomeric compression spring members, e.g. rubber, neoprene, Santoprene, ethylene vinyl acetate, etc. or resilient foam compression spring members made from an elastomer or other resilient polymer. FIG. 52 shows just one of many possible configurations for the expansion cells 310.

Figure 53:
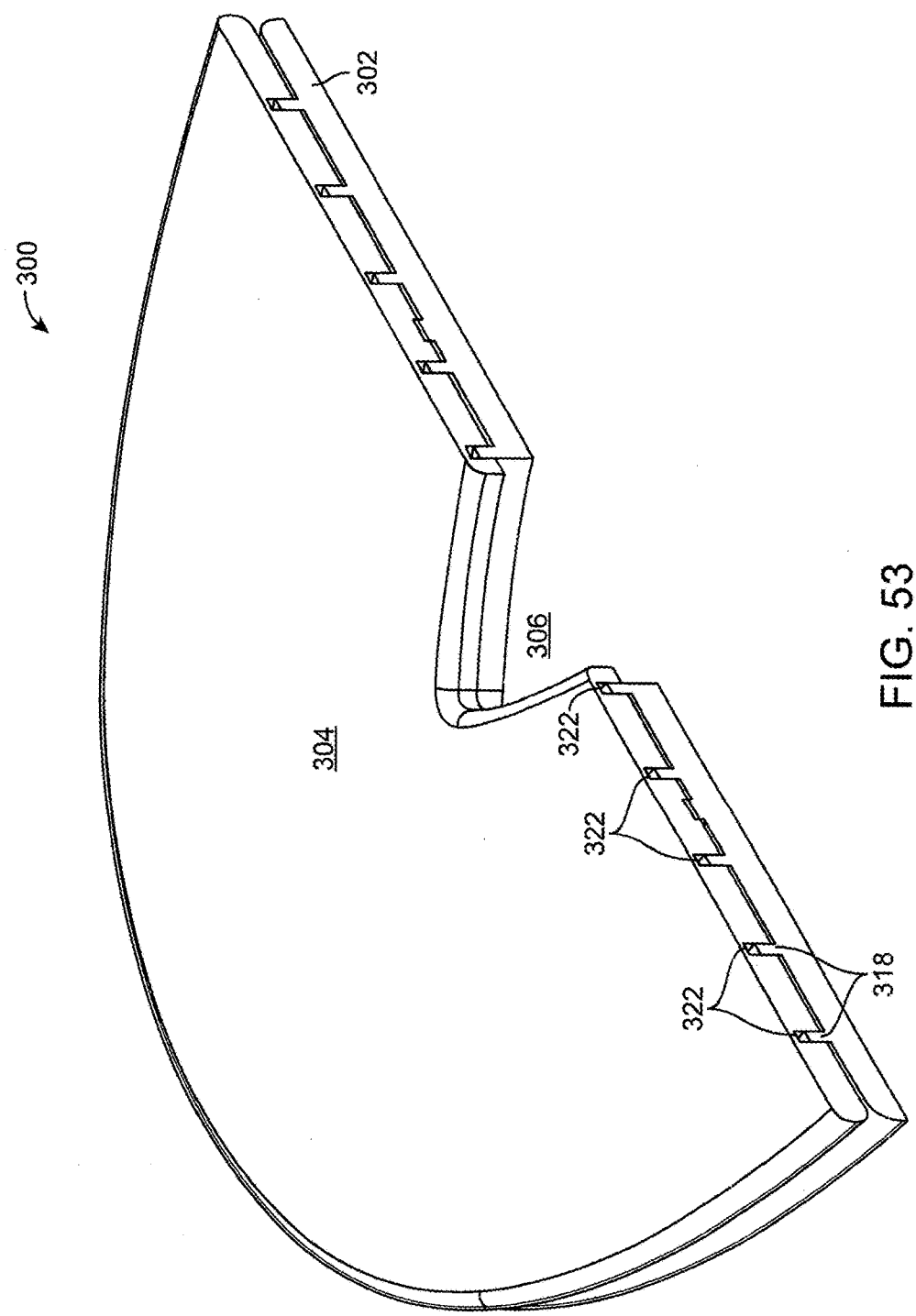
FIG. 53 is a cutaway view showing one half of the surgical closure device of FIG. 50.
Figure 54:
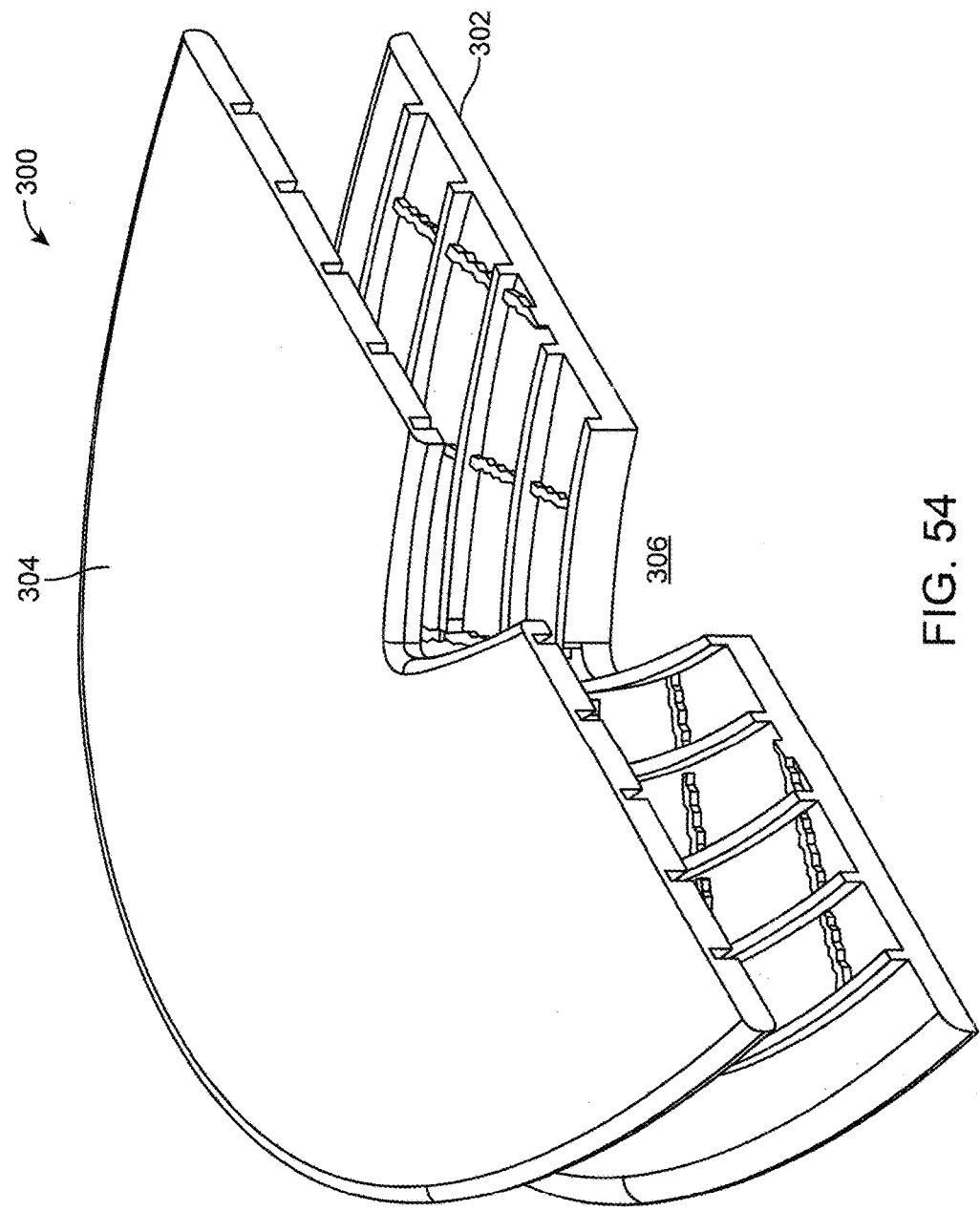
FIG. 54 is a cutaway view of the surgical closure device of FIG. 50 with the retainer lifted off the device.

FIG. 53 is a cutaway view showing one half of the surgical closure device 300 with the retainer 304 assembled to the adhesive patch 302. The retainer 304 has a plurality of grooves 322 that interlock with the arcuate ribs 318 on the adhesive patch 302 to hold the adhesive patch 302 in an expanded position with the compression spring members 320 in a compressed state. The retainer 304 is preferably molded from a polymer material that is stiff enough to resist the combined force of the compression spring members 320.

The assembled surgical closure device 300, as shown in FIG. 50, is adhered to the patient's skin with the central opening 306 positioned around the intended incision site. The inner edge of the retainer 304 may be used as a guide for cutting a wedge-shaped biopsy sample or portion of tissue with a lesion to be removed. When it is desired to close the incision, the retainer 304 is lifted off of the adhesive patch 302, as shown in the cutaway view in FIG. 54, leaving the adhesive patch 302 adhered to the skin, as shown in FIG. 51. The ribs 318 on the adhesive patch 302 are no longer constrained by the grooves 322 on the retainer 304, so the compression spring members 320 will urge the central opening 306 toward a closed position.

In one optional configuration of the surgical closure device 300, the compression spring members 320 and/or the adhesive patch 302 may be made of a viscoelastic material that slowly urges the central opening 306 toward a closed position. Optionally, the viscoelastic material may be activated by the patient's body heat.

Figure 55:
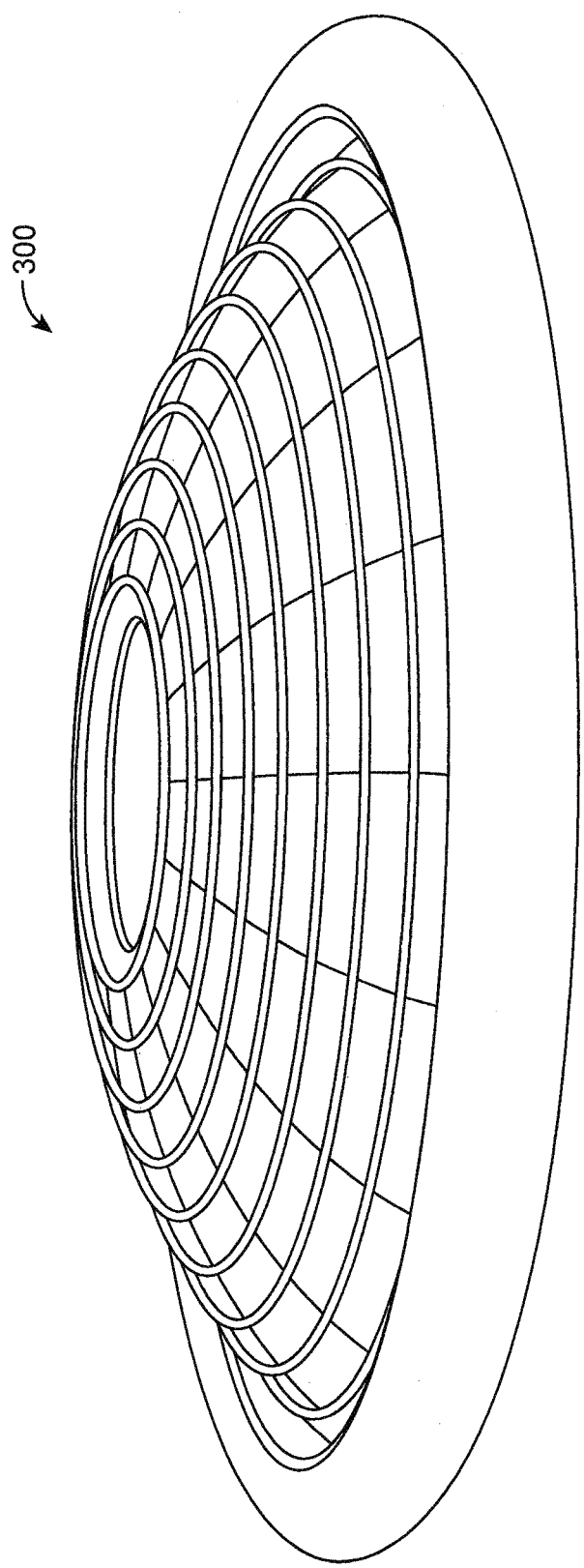
FIG. 55 is a perspective view of a dome-shaped surgical closure device.

FIG. 55 shows an optional feature that may be used with the surgical closure device 300 of FIGS. 50-54 or with any embodiment of the surgical closure device described herein. The surgical closure device 300 is configured with a nonplanar or three-dimensional contour for fitting to a body part. In the example shown, the surgical closure device 300 is shaped like a dome for a better fit on a patient's scalp or other convexly curved portion of the body. Other configurations are also possible.

Figure 56:
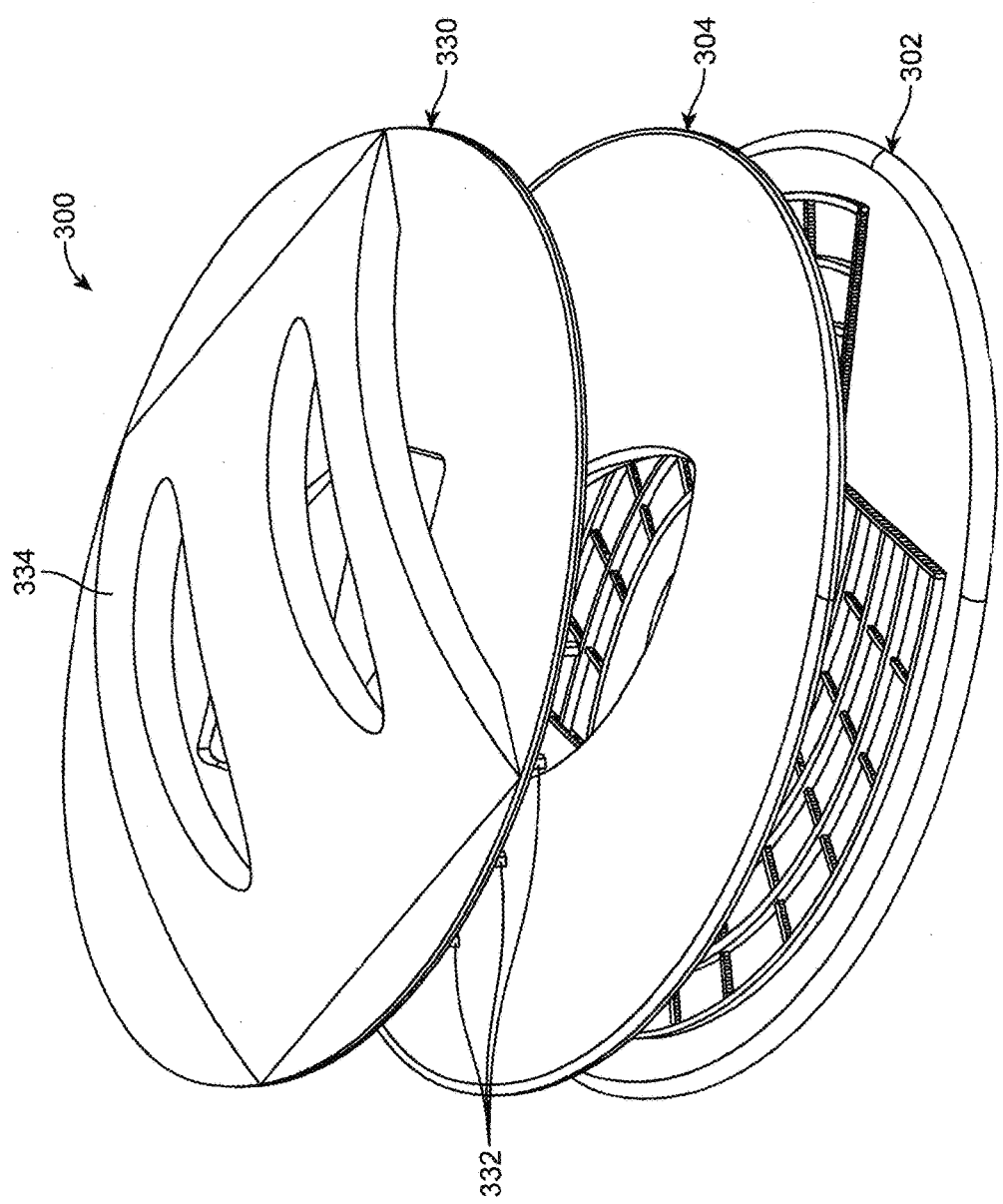
FIGS. 56 and 57 show top and bottom exploded views of a surgical closure device with a skin cutting device.
Figure 57:
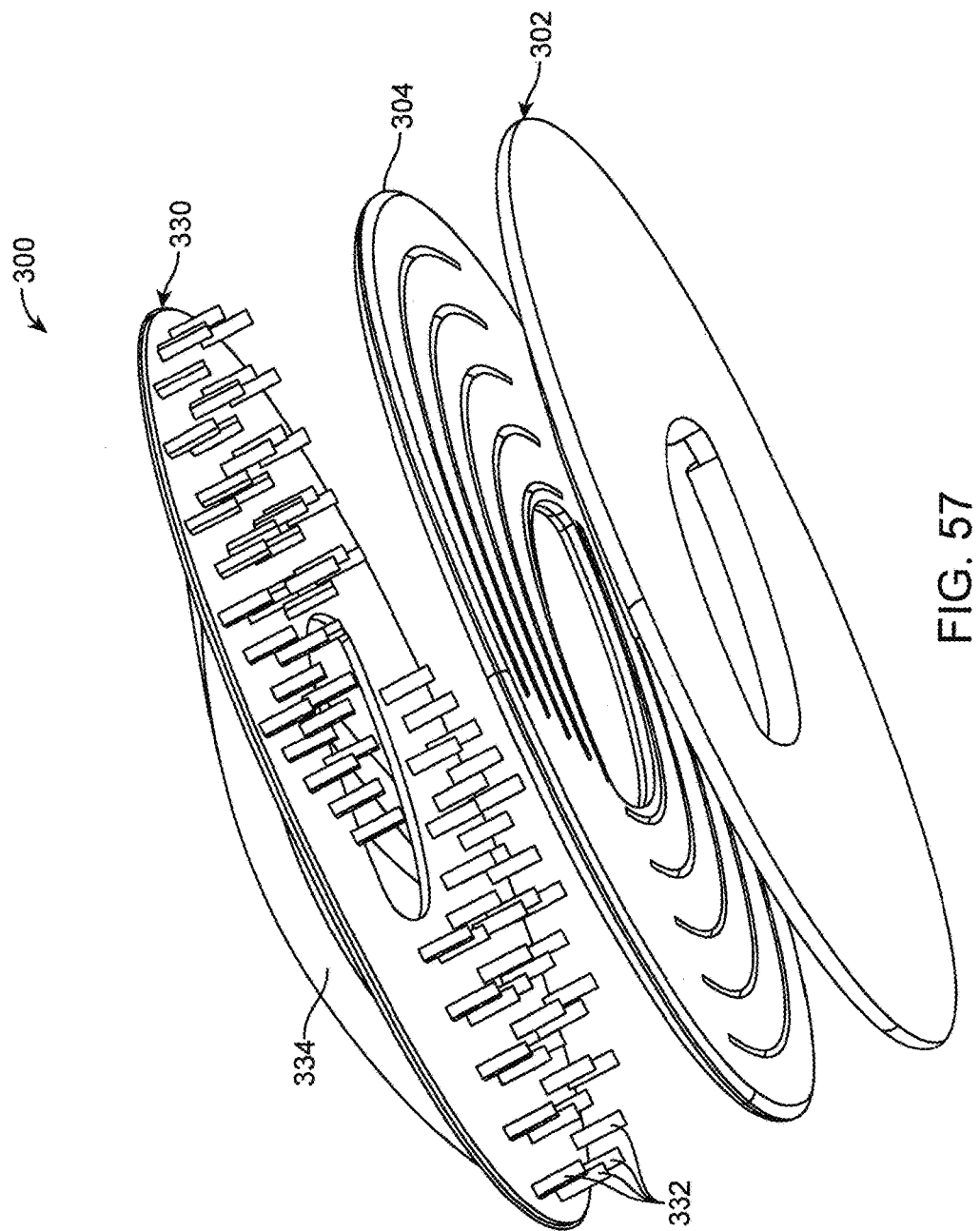
Figure 58:
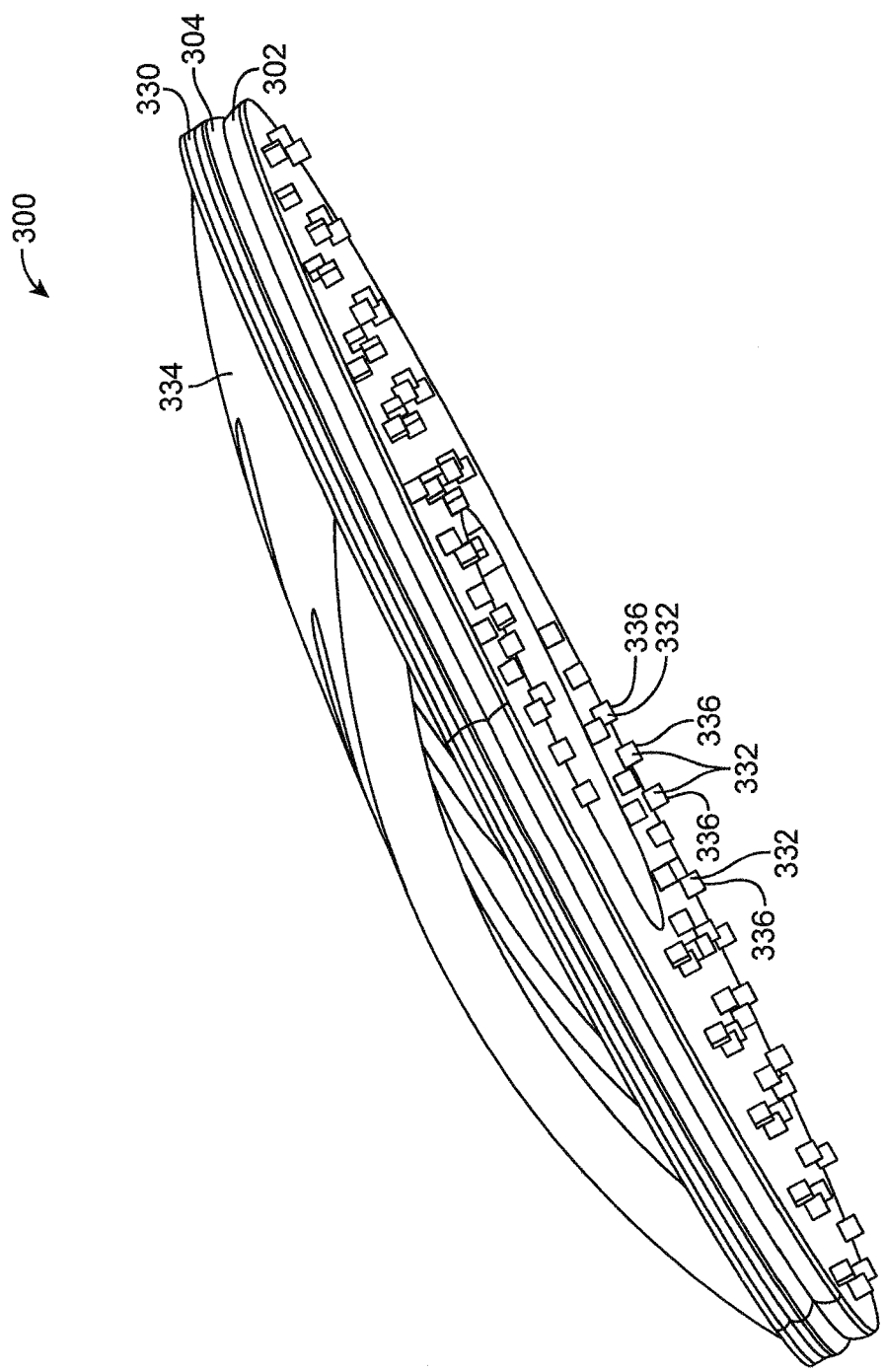
FIG. 58 is an assembly drawing of the surgical closure device with a skin cutting device shown in FIGS. 56 and 57.

FIGS. 56-58 show another optional feature that may be used with the surgical closure device 300 of FIGS. 50-54 or with any embodiment of the surgical closure device described herein. The surgical closure device 300 includes a skin cutting device 330 having a multiplicity of cutter blades 332 attached to a handle 334. FIGS. 56 and 57 show top and bottom exploded views of the surgical closure device 300 with the skin cutting device 330. The skin cutting device 330 fits over the top of the surgical closure device 300 with the cutter blades 332 extending through slots in the adhesive patch 302 and the retainer 304. The sharpened ends 336 of the cutter blades 332 extend a short distance past the surface of the adhesive patch 302, as shown in the assembly drawing of FIG. 58, so that they can cut approximately 1-2 mm deep into the skin. Preferably, the cutter blades 332 are arranged so that they will cut the skin in a mesh pattern around the incision so that it can expand to make up the skin deficit created by removing a portion of the skin and underlying tissue. The small cuts will heel more quickly and with less scarring than the large incision where a lesion has been removed. The skin cutting device 330 is removed after the skin has been perforated.

The skin cutting device 330 may be applied to the skin at the same time as the adhesive patch 302 and the retainer 304 or alternatively, the skin cutting device 330 may be applied after the adhesive patch 302 and the retainer 304 have already been adhered to the skin. In another alternative configuration, the cutter blades 332 may be integrated into the retainer 304 so that the cutter blades 332 are applied to the skin at the same time that the surgical closure device 300 is adhered to the patient.

Figure 59:
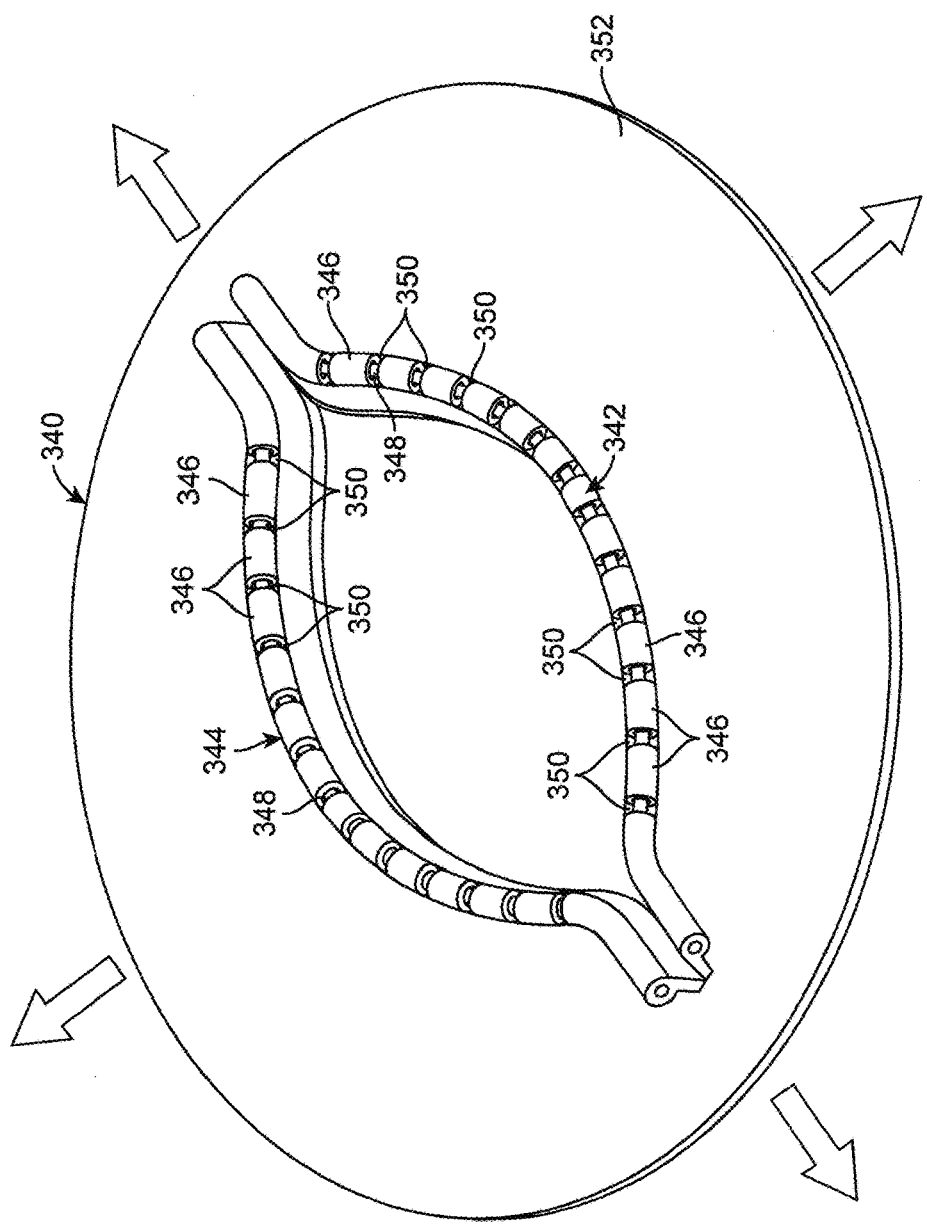
FIG. 59 is a perspective view of a surgical closure device with segmented rails.
Figure 60:
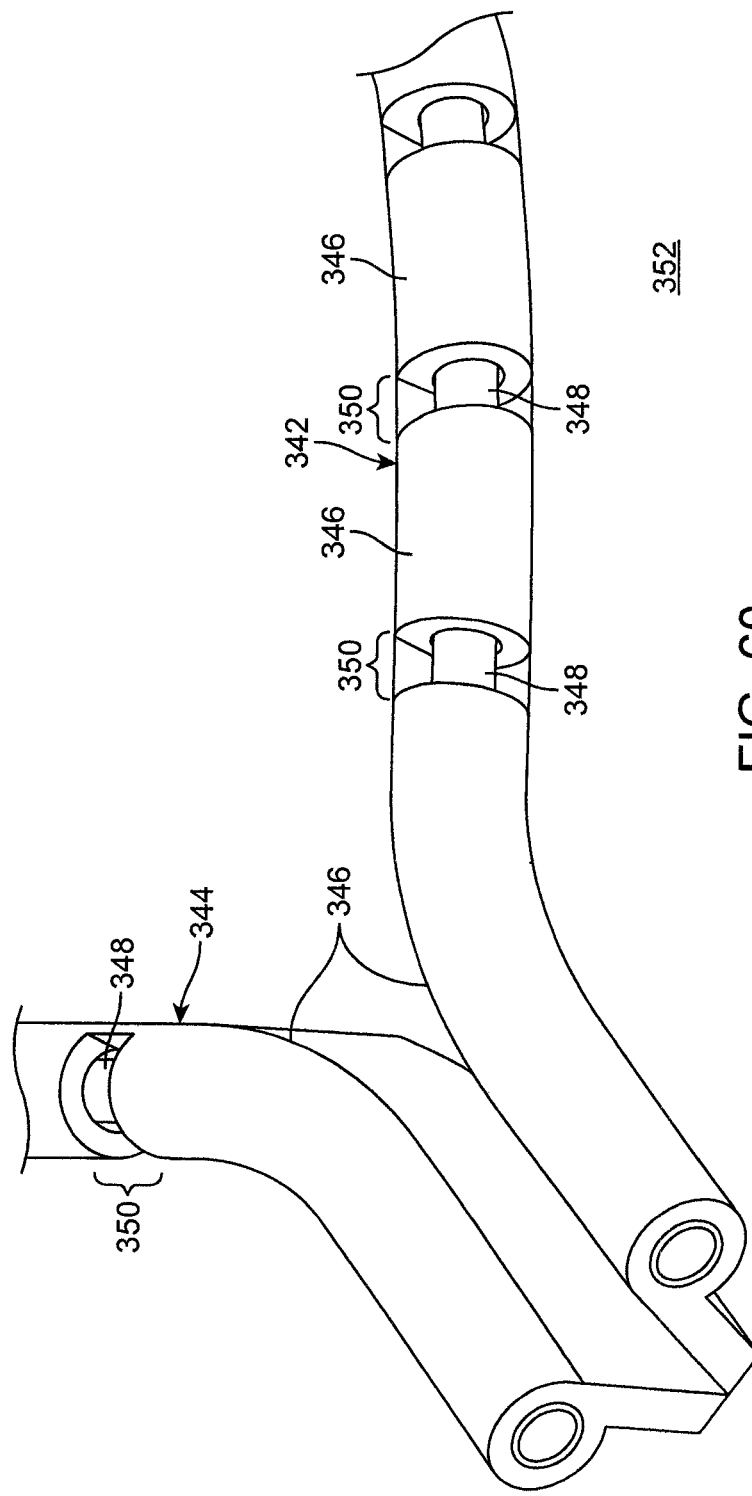
FIG. 60 is an enlarged view of the segmented rails in the surgical closure device of FIG. 59.

FIGS. 59 and 60 illustrate an optional feature that can be used with any of the embodiments of the surgical closure device described herein. FIG. 59 is a perspective view of a surgical closure device 340 with segmented rails 342, 344 that facilitate retraction of the incision for improved surgical access. Each of the rails 342, 344 is constructed with a plurality of segments 346 that are linked together by an elastic cord 348, or the like. When the incision and the surgical closure device 340 are subjected to retraction threes, for example using one or more surgical retractors, the segments 346 separate, forming gaps 350 between the segments 346 as shown in FIG. 59. FIG. 60 is an enlarged view of the segmented rails 342, 344 with the segments 346 separated and the elastic cord 348 visible through gaps 350. The elasticity of the adhesion patch 352 allows it to expand as the incision is retracted.

When the retraction forces are released, the elastic cord 348 pulls the segmented rails 342, 344 back to their normal continuous configuration, similar to the configuration shown in FIG. 17. When it is time to close the surgical incision, a binder 106 may be applied, as shown in FIGS. 18 and 19.

Figure 61:
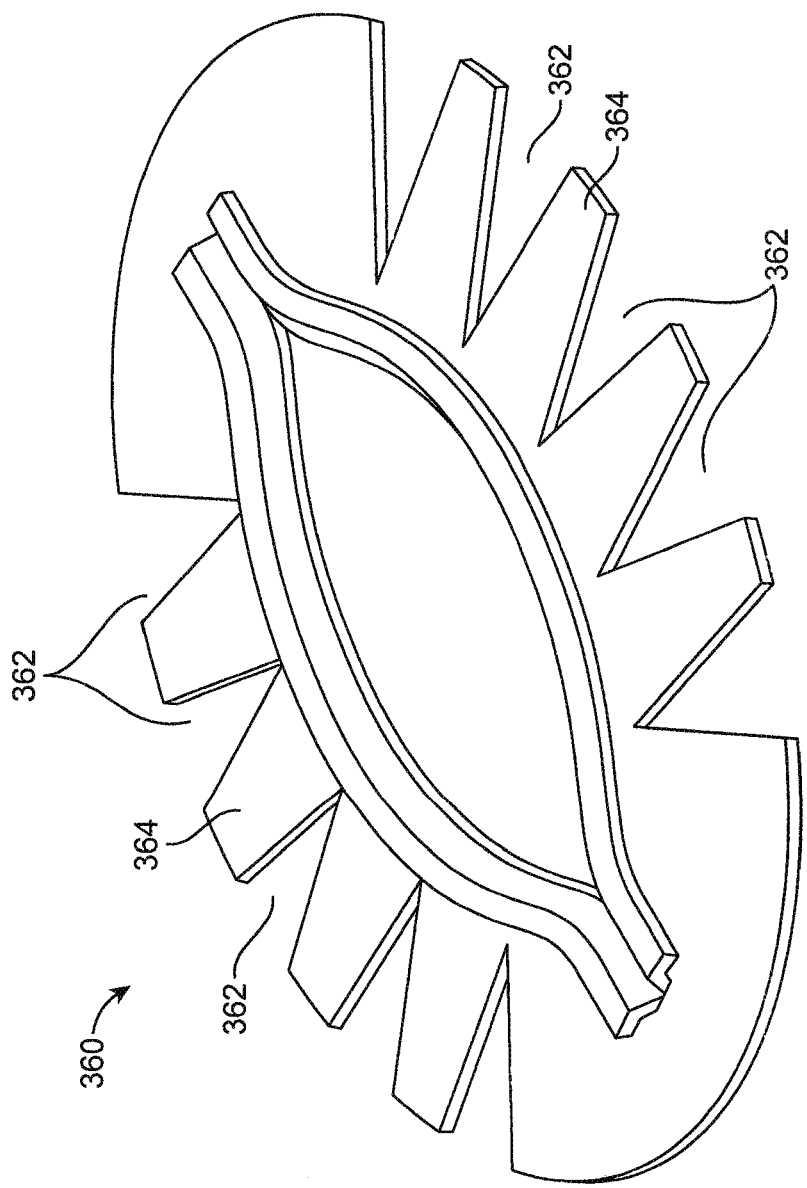
FIG. 61 is a perspective view of a surgical closure device with lateral slots in the adhesion patch.
Figure 66D:
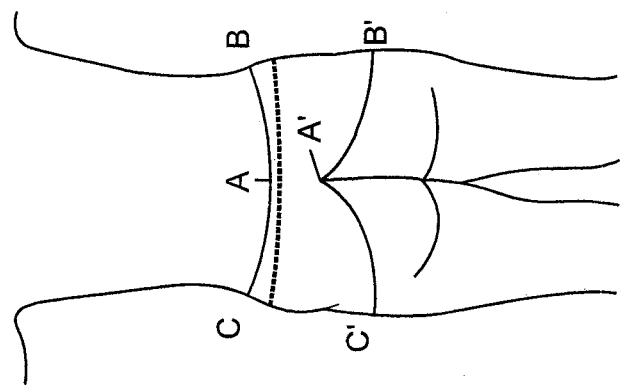
FIGS. 66A-66D show incision lines that are frequently used in surgical removal of redundant skin following successful bariatric surgery.
Figure 66C:
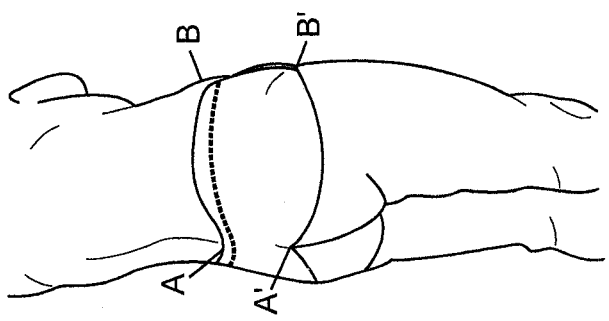
Figure 66B:
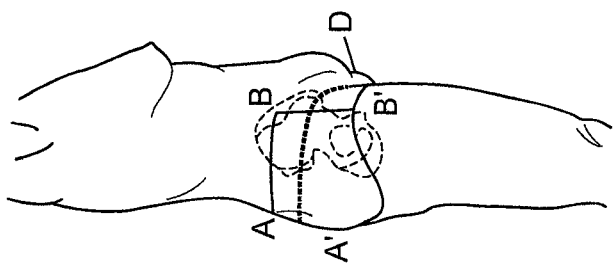
Figure 66A:
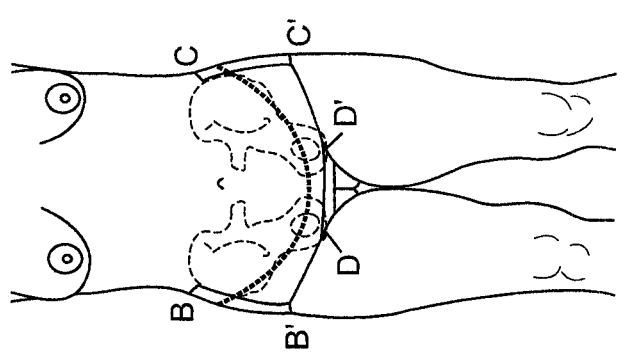

FIG. 61 show another optional feature that can be used with any of the embodiments of the surgical closure device described herein, including the embodiment shown in FIGS. 59 and 60. FIG. 61 is a perspective view of a surgical closure device 360 with lateral slots 362 in the adhesion patch 364. The lateral slots 362 allow the adhesion patch 364 to expand when a retraction force is applied. The lateral slots 362 also allow the adhesion patch 364 to conform to the closed position of the surgical closure device, as shown in FIG. 19. Because of the lateral slots 362, less flexibility or deformation of the adhesion patch 364 material is required to accommodate the changes in shape during retraction or closure of the surgical closure device 360.

Another optional feature that can be used with any of the embodiments of the surgical closure device described herein is to construct the surgical closure device 100 with one or more heat exchanger passages within the first and second adhesion patches 102, 104 for circulating cold water or another heat exchange fluid to help control pain and inflammation as the incision heals. The heat exchanger passages may be laid out in a serpentine pattern or other configuration to improve heat exchange efficiency. The surgical closure device 100 may have ports for connecting the heat exchanger passages to an external pump. Alternatively, other means of heat exchange may be used in conjunction with the surgical closure device 100 to raise or lower the temperature, at the incision site.

FIGS. 62-65 illustrate another embodiment of a surgical closure device 400 that is configured for making and subsequently closing a shaped incision in the patient's skin, for example a wedge biopsy incision. The surgical closure device 400 is similar in many respects to the embodiment of FIG. 16. There is a nonlinear shaped opening 408 between the first adhesion patch 402 and the second adhesion patch 404 that defines the shape of the incision in one particularly preferred embodiment, the shaped opening 408 has the geometry of an ellipse or a rounded lozenge shape somewhat like the shape of an American football or a convex-convex lens. The first rail 412 and the second rail 414 follow the outline of the shaped opening 408. Preferably, the first and second adhesion patches 402, 404 are joined together beyond the ends of the shaped opening 408. The first adhesion patch 402, the second adhesion patch 404, the first rail 412 and the second rail 414 are made of flexible materials that allow the shaped opening 408 to move from an open position to a closed position. Optionally, the shaped opening 408 may be biased toward the open position or the closed position.

The surgical closure device 400 has two separate binders, an open binder 406 shown in FIG. 62 and a closed binder 410 shown in FIG. 65. The open binder 406 has two channels 416, 418 on the underside that follow the contours of a shaped opening 420 similar in shape to the opening 408 on the device 400 between the first adhesion patch 402 and the second adhesion patch 404. Preferably, an inner edge 422 of the shaped opening 420 in the open binder 406 is beveled at an angle (typically 45-90 degrees) to provide a cutting guide for a scalpel 424 when making a wedge biopsy incision. The open binder 406 is preferably made of a material, such as a polymer and/or metal, that is more rigid than the adhesion patches 402, 404 and the rails 412, 414. When the open binder 406 is attached to the surgical closure device 400, the channels 416, 418 engage the first r it 412 and the second rail 414 and hold the shaped opening 408 of the device 400 in an open position, as shown in FIG. 62. For the convenience of the medical practitioner, the surgical closure device 400 is preferably supplied in a sterile package with the open binder 406 already attached. The closed binder 410 has two channels 426, 428 on the underside that are substantially straight and parallel to one another. The closed binder 410 is preferably made of a material, such as a polymer and/or metal, that is more rigid than the adhesion patches 402, 404 and the rails 412, 414. When the closed binder 410 is attached to the surgical closure device 400, the channels 426, 428 engage the first rail 412 and. the second rail 414 and hold the shaped opening 408 of the device 400 in a closed position, as shown in FIG. 65.

In use, the first adhesion patch 402 and the second adhesion patch 404 of the surgical closure device 400, with the open binder 406 attached, are adhered to the patient's skin with the shaped openings 408, 420 positioned around a suspected lesion, as shown in FIG. 62. An incision is made with a scalpel 424 or other cutting instrument, using the beveled inner edge 422 of the shaped opening 420 in the open binder 406 as a cutting guide, as shown in FIG. 63. The open binder 406 provides an additional benefit in that it protects the edges of the surgical closure device 400 adjacent to the shaped opening 408 from being accidentally cut during the incision step. The excised portion of tissue is removed, as shown in FIG. 64, and the open binder 406 is removed by lifting it off of the rails 412, 414. The closed binder 410 is attached to the surgical closure device 400 by sliding the channels 426, 428 over the rails 412, 414 to close the shaped opening 408 and incision in the skin, as shown in FIG. 65. Optionally, the device 400 may be configured to apply a desired amount of compression to the incision when the closed binder 410 is attached in order to promote healing.

FIGS. 67-71 illustrate an embodiment of a surgical closure device 440 that is configured for closing a large incision in a patient's skin. One example of a procedure that would benefit from the use of such a device is the removal of redundant skin following successful bariatric surgery. Over 200,000 bariatric surgeries are currently performed each year and the number is growing. Removal of redundant skin is a very time consuming procedure with approximately 2000 stitches in predictable places over straight lines guided by anatomical landmarks. To make it go quicker, this procedure is typically performed by a team of surgeons. FIGS. 66A-66D show the incision lines that are frequently used in surgical removal of redundant skin.

FIG. 67 shows the surgical closure device 440 in an open position. The surgical closure device 440 may be a single device that will surround the entire circumference of the patient or, alternatively, the device may be modular and made up of either separate or interconnected segments. The surgical closure device 440 has a first rail 442 and a second rail 444 with a contact adhesive backing for adhering them to the patient's skin. In one preferred embodiment, the first rail 442 and the second rail 444 are as long as or slightly longer than the length of the incision. In the case of redundant skin removal after bariatric surgery, the first rail 442 and the second rail 444 may be long enough to completely encircle the patient. Alternatively, the first rail 442 and the second rail 444 may be in shorter segments that can be adhered to the patient's skin and joined end-to-end when closing the incision. Optionally, a first end of the first rail 442 and the second rail 444 may be permanently joined together to facilitate closing the device.

FIG. 68 shows the surgical closure device 440 of FIG. 67 in an open position and adhered to a patient's abdomen. The first rail 442 and the second rail 444 are placed along the intended incision lines with the excess skin to be removed positioned between the first rail 442 and the second rail 444. FIG. 69 shows the patient with the redundant skin and fascia excised. Small margins of fascia are left for reattachment using conventional suture methods.

FIG. 70 shows the surgical closure device 440 in a partially closed position with the first rail 442 and the second rail 444 approximated to one another so that the edges of the skin will be properly approximated. A binder 446 has been started on the first end of the first rail 442 and the second rail 444. FIG. 71 shows the surgical closure device 440 on the patient's abdomen in the partially closed position.

FIG. 72 shows the surgical closure device 440 on the patient's abdomen in a closed position. The binder 446 has been slid onto the first rail 442 and the second rail 444. Optionally, the excess length of the first 442 and the second rail 444 may be removed.

FIGS. 73A-73E illustrate an optional feature that may be combined with the surgical closure device 440 of FIGS. 67-72 or any of the other surgical closure devices described herein. FIG. 73A shows short sample sections of the first rail 442 and the second rail 444 adhered to the patient's skin. After the excess tissue has been excised, alignment cords 448 are inserted through premade holes 450 in the first rail 442 and the second rail 444. Then, the alignment cords 448 are pulled to approximate the first rail 442 and the second rail 444 to one another. Optionally, the alignment cords 448 may have barbs, ratchet teeth or other features to lock the first, rail 442 and the second rail 444 together in this position. The binder 446 is then slid onto the first rail 442 and the second rail 444 to secure the closure. Optionally, the excess length of the alignment cords 448 may be removed at this time. FIG. 74 is an enlarged view of the surgical closure device 440 of FIGS. 73A-73E in the closed position.

Other surgeries that require a large incision or any incision that might leave a visible scar would also benefit from the use of such a device, including laparotomy, thoracotomy, cesarean section, facelift, and breast implant surgery.

One of the challenges in closing large incisions, such as those encountered during removal of redundant skin in bariatric patients, is the prevention of "dog ears" in the closed incision. Dog ears occur when one side of the incision is longer than the other or when one side of the incision is inadvertently stretched while closing the incision. If care is not taken to make sure that the additional length of the longer side is evenly distributed along the shorter side during apposition and suturing, the skin will bunch up along one side of the incision and pucker out in a shape that sometimes resembles a dog's ear. For good cosmetic results, the sutures must be undone and the incision must be resutured. It can be very time consuming for the surgeon to correct this mistake.

The surgical closure device of the present invention can be very helpful in preventing the occurrence of dog ears. One approach is to make the rails of the surgical closure device in multiple segments along one or both sides of the closure. Spaces between the segments along the longer side of the incision can be compressed to provide even distribution of the additional length of skin along the shorter side during apposition. The pull cords described above can be used to assure even apposition between the two sides of the incision during closure of the device. Alternatively or in addition, longitudinal pull cords may be provided along one or both sides of the surgical closure device. The longitudinal pull cord on the longer side of the incision can be pulled to shorten the longer side of the incision evenly prior to apposition and closure of the device. Optionally, the segments along the longer side of the incision can be made shorter than the segments on the shorter side to facilitate even apposition. Another approach is to deliberately stretch the skin on the shorter side of the incision prior to applying the adhesive patches of the surgical closure device to the patient's skin. This will assure even apposition and closure of the incision when the binder is applied to the surgical closure device.

Figure 75:
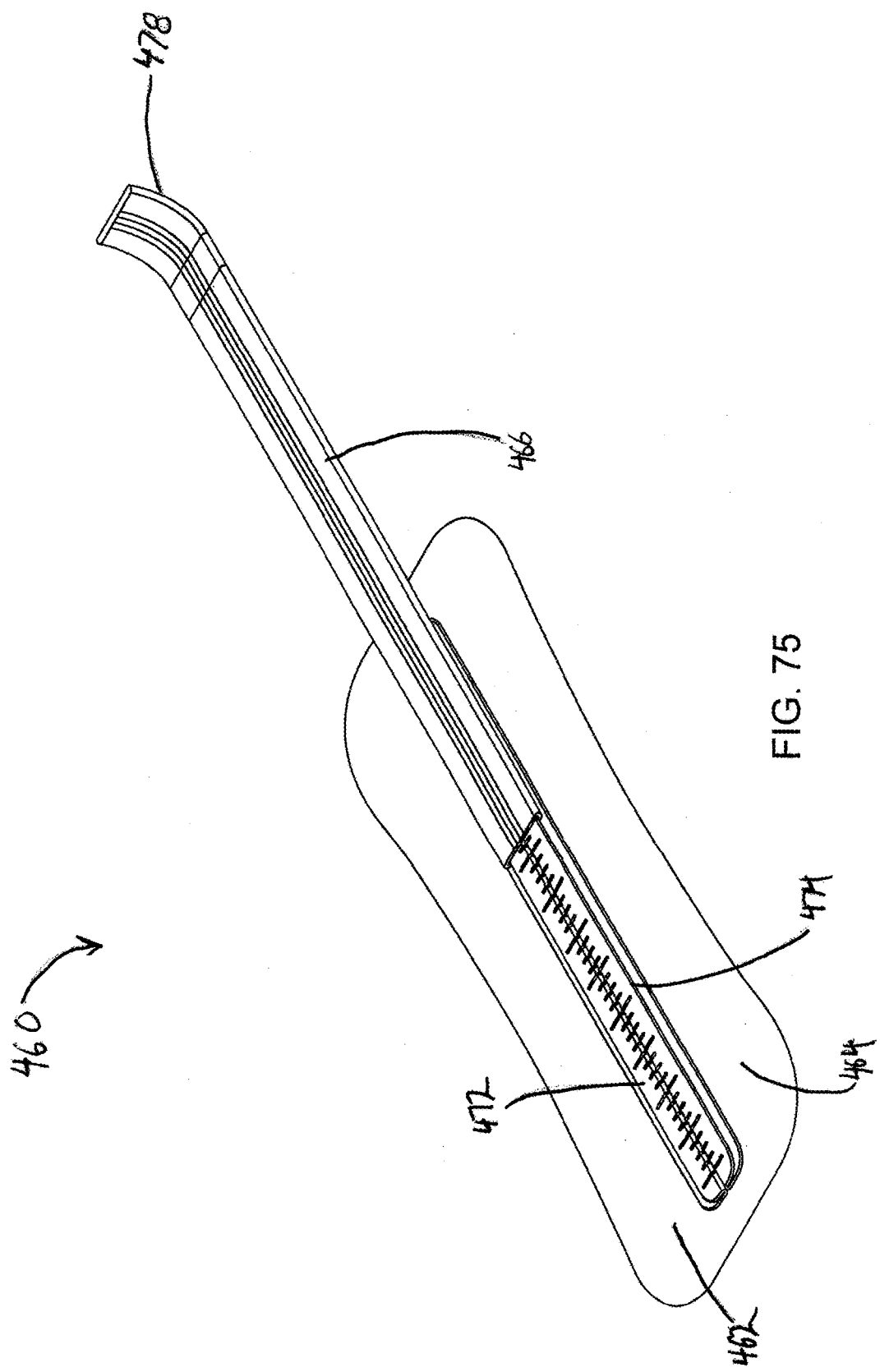

The surgical closure device can be made in one or more standard configurations based on common incision geometries. Alternatively, the surgical closure device can be customized based an individual patient's measurements. FIG. 75 shows a low-profile embodiment of a surgical closure device 460 that will be more comfortable and less conspicuous for patients to wear. The surgical closure device 460 has a first adhesion patch 462 with a first rail 472 attached and a second adhesion patch 464 with a second rail 474 attached. Optionally, the first and second adhesion patches 472, 474 may be joined together beyond the ends of the rails 472, 474 as shown. Preferably, the adhesion patches 462, 464 are made from a breathable and flexible material, such as a flexible fabric or a perforated flexible polymer sheet (optionally reinforced), with a contact adhesive applied to the underside. Optionally, the first and second adhesion patches 472, 474 may be made from or coated with a hydrophobic material to resist absorbing or being stained by the patient's blood. A flexible binder 466 is sized and configured to slide over the rails 472, 474 to bind the first adhesion patch 462 and the second adhesion patch 464 together.

Figure 76:
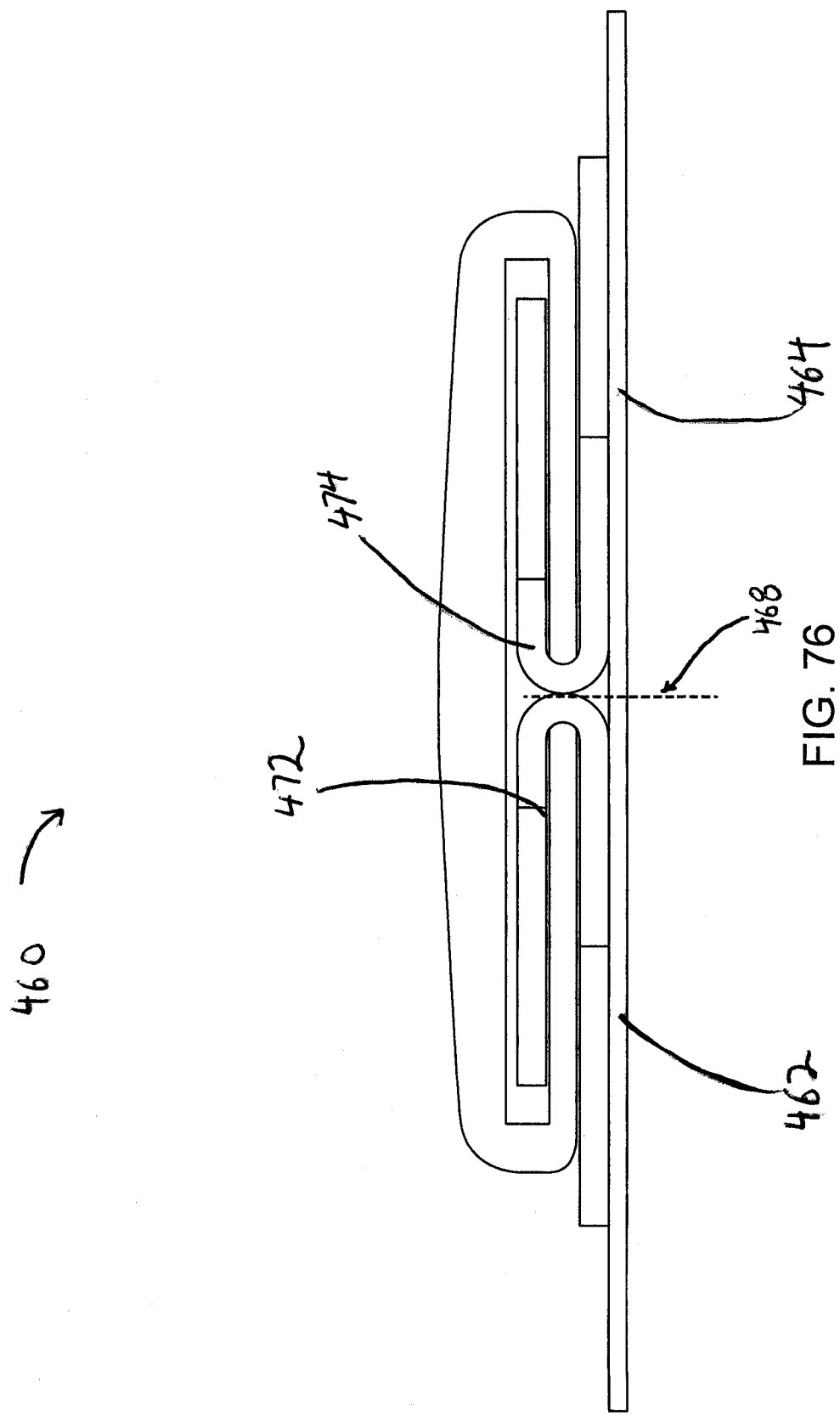
Figure 77:
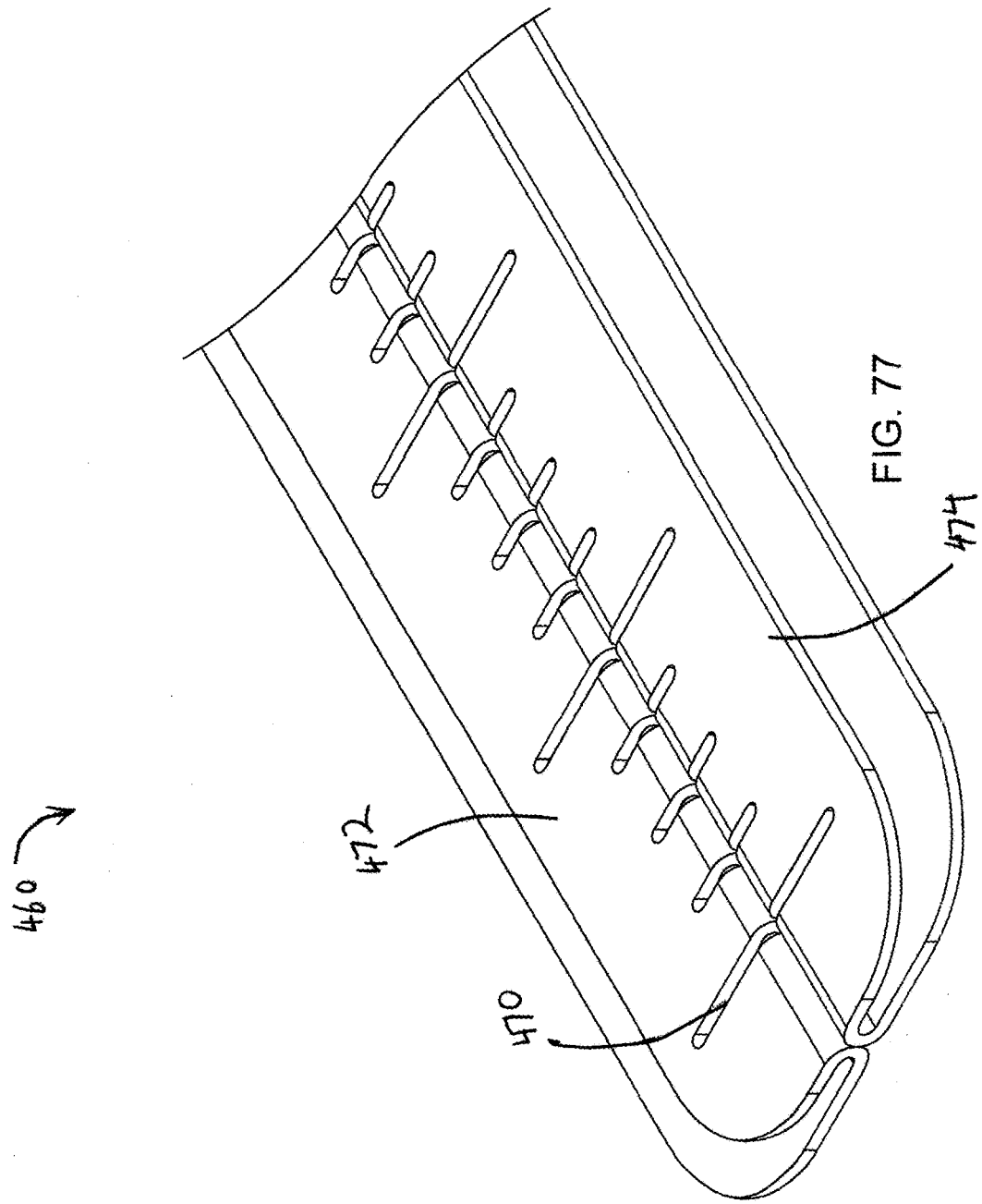
Figure 78:
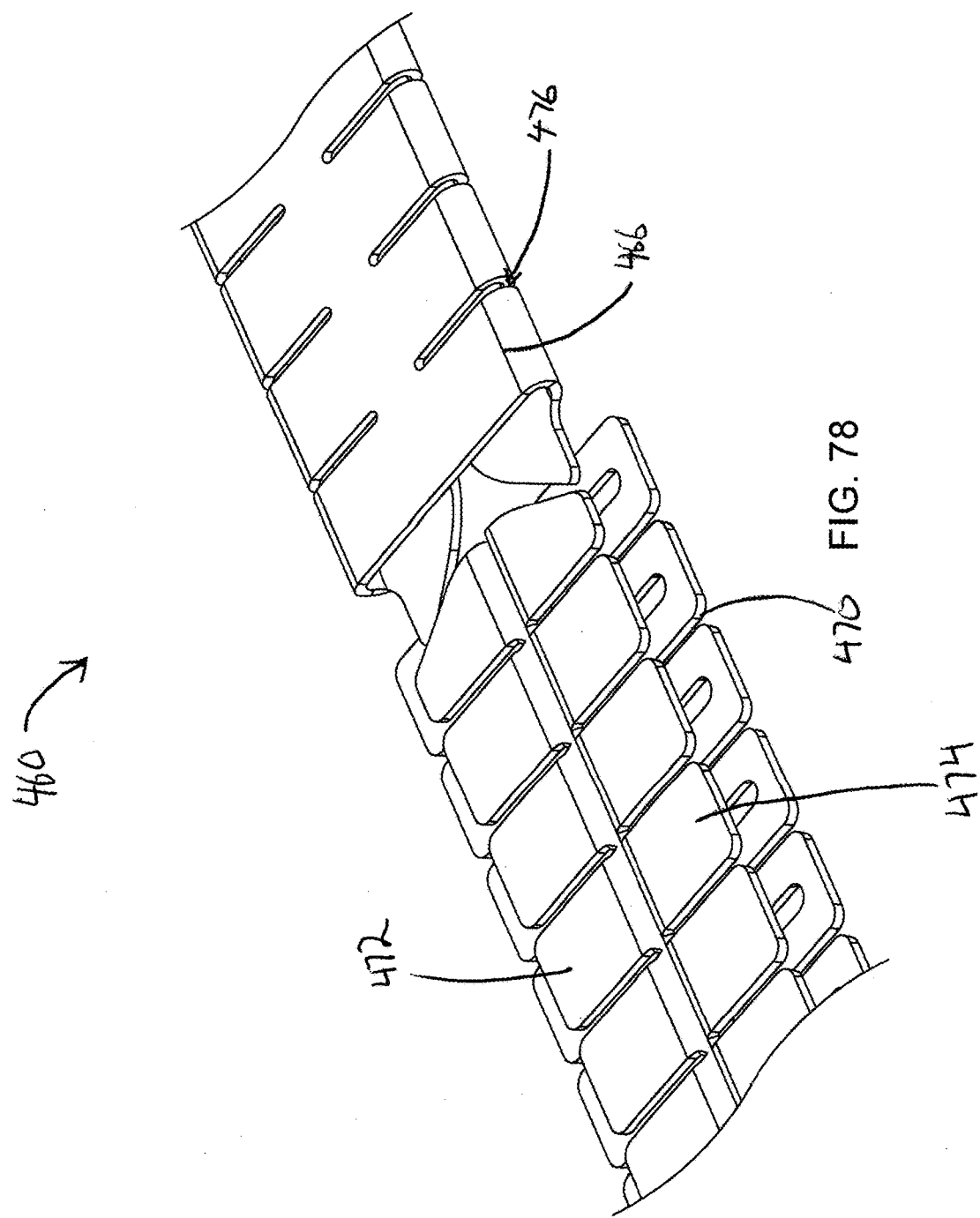

FIG. 76 is a cross section of the low-profile surgical closure device 460 of FIG. 75. An incision plane 468 is defined between the first rail 472 and the second rail 474. Optionally, the surgical closure device 460 may be cut through at the incision plane 468 between the first and second adhesion patches 462, 464 or it may be intact so that the surgeon will cut through it at the time of making the skin incision. Alternatively, the surgical closure device 460 may be perforated or partially cut through at the incision plane 468. The first rail 472 and the second rail 474 are preferably U-shaped or J-shaped in cross section and positioned with their bends adjacent to the incision plane 468. Preferably, the first rail 472 and the second rail 474 are made of a metal, for example stainless steel, that has been cut or etched with a pattern of slots 470 to make it flexible, while retaining the strength of the U-shaped or J-shaped configuration. Examples of possible slot 470 geometries are shown in close-up drawings in FIGS. 77, 78 and 79. The flexible binder 466 is preferably C-shaped in cross section for a close fit around the first rail 472 and the second rail 474. Preferably, the flexible binder 466 is made of a metal, for example stainless steel, that has been cut or etched with a pattern of slots 476 to make it flexible, while retaining the strength of the C-shaped configuration. Examples of possible slot 476 geometries are shown in close-up drawings in FIGS. 78 and 79. Optionally, the flexible binder 466 may be covered or coated with a flexible polymer with a low coefficient of friction. Optionally, the flexible binder 466 may have a break-off handle 478 (See FIG. 75) that can be removed to minimized the profile of the device 460 after the binder 466 has been installed. FIG. 78 illustrates an optional feature of the low-profile surgical closure device 460 of FIG. 75. An end of the rails 472, 474 and/or an end of the flexible binder 466 may be formed with a tapered configuration to facilitate insertion of the rails 472, 474 into the binder 466.

FIGS. 79-80 illustrate another optional feature of the low-profile surgical closure device 460 of FIG. 75. The rails 472, 474 and the flexible binder 466 may be formed with interlocking features that will securely lock the binder 466 to the rails 472, 474 once it has been installed. In the example shown, the interlocking features include a pair of tabs 480 formed on the end of the flexible binder 466 that interlock with a pair of spring detents 482 formed on the ends of the rails 472, 474.

FIGS. 81-86 illustrate another low-profile embodiment of a surgical closure device 490. As shown in FIG. 82, the surgical closure device 490 has a first adhesion patch 492 and a second adhesion patch 494 that meet along an opening 493 that defines an incision line. The first adhesion patch 492 and the second adhesion patch 494 may be separate or, optionally, may be joined together beyond the ends of the opening 493. A first sleeve 496 is connected to the first adhesion patch 492 along one edge of the opening 493 and a second sleeve 498 is connected to the second adhesion patch 494 along the opposite edge of the opening 493. Preferably, the first adhesion patch 492, the first sleeve 496, the second adhesion patch 494 and the second sleeve 498 are made of a flexible, breathable fabric. The sleeves 496, 498, which are shown in cross section in FIG. 83, can be formed by adhesive bonding, sewing or welding the fabric. The sleeves 496, 498 may be continuous, as shown, or they may be configured in intermittent segments to make the surgical closure device 490 more flexible.

The sleeves 496, 498 of the surgical closure device 490 serve the same function as the rails in other embodiments described herein. The function of the binder is served by an elongated fork-shaped binder 500, shown in FIG. 84, having a first tine 502 and a second tine 504 that are configured for a sliding fit within the first and second sleeves 496, 498, respectively. The first tine 502 and the second tine 504 of the fork-shaped binder 500 are attached at one end by a cross member 503. The fork-shaped binder 500 is preferably formed of a metal, such as stainless steel, nickel-titanium or other suitable alloy by any suitable process, such as machining, stamping, photoetching, etc. Alternatively, the fork-shaped binder 500 may be formed of a rigid polymer or a fiber-reinforced polymer composite. In one particularly preferred embodiment, the fork-shaped binder 500 is configured with a partially-open section 506 where the first tine 502 and the second tine 504 are spaced apart by a small gap 505 and a closed section 508 where the first tine 502 and the second tine 504 are side-by-side with little or no gap in between. Additionally, there may be an end section 507 where the first tine 502 and the second tine 504 are tapered to facilitate insertion into the first and second sleeves 496, 498. Optionally, there may be a cover seal 510 attached to the fork-shaped binder 500. The cover seal 510 may be made from the same material as the fork-shaped binder 500 or a different material.

Figure 81:
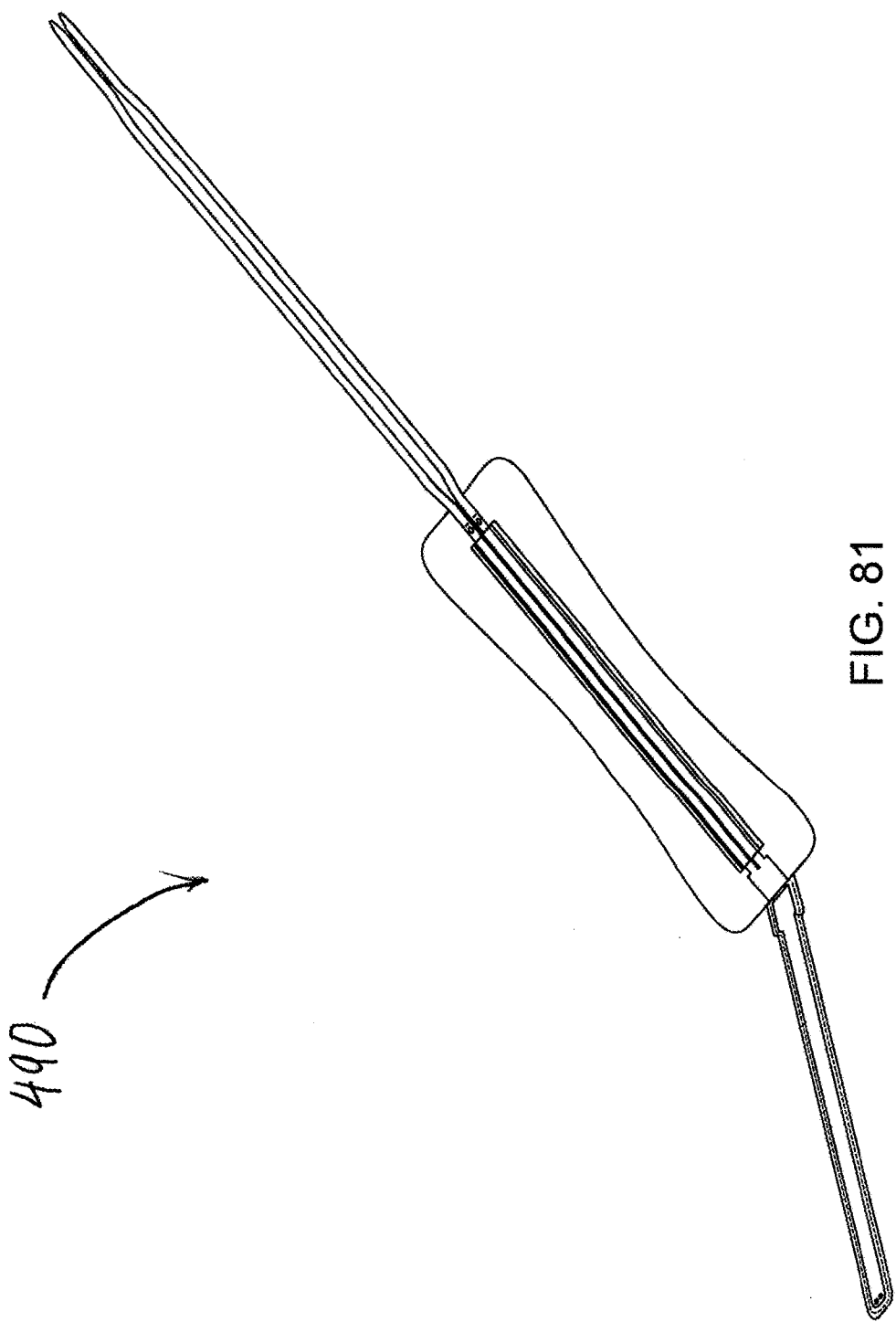

In use, the surgical closure device 490 is adhered to the patient's skin with a contact adhesive on the underside of the first adhesion patch 492 and the second adhesion patch 494. The closed section 508 of the fork-shaped binder 500 is positioned within the first and second sleeves 496, 498 to hold the surgical closure device 490 in a closed position, as shown in FIG. 81. Next, the fork-shaped binder 500 is slid longitudinally so that the partially open section 506 of the fork-shaped binder 500 is positioned within the first and second sleeves 496, 498 to hold the surgical closure device 490 in a partially open position. While the surgical closure device 490 in the partially open position, an incision is made in the skin through the opening 493 formed between the first adhesion patch 492 and the second adhesion patch 494. After the incision is made, the fork-shaped binder 500 may be temporarily removed from the first and second sleeves 496, 498 to allow the opening 493 and the tissue below to be retracted for performing surgery through the incision. After the surgery has been completed, the fork-shaped binder 500 is reinserted and moved to the closed position to close the opening 493 between the first adhesion patch 492 and the second adhesion patch 494. The tissue will be precisely apposed in the same position as before the surgery. Optionally, the fork-shaped binder 500 may apply a compressive force on the incision in the dosed position. The sections 506, 507 of the fork-shaped binder 500 that are no longer needed are preferably removed by bending the tines 502, 504 upward and breaking them off at a score line 509 on the underside of the tines 502, 504 or, alternatively, by cutting the tines 502, 504 off with a cutting device. Next, the cover seal 510 is folded over the first and second sleeves 496, 498 and the closed section of the fork-shaped binder 500 to lock and seal the surgical closure device 490 in the closed position, as shown in FIGS. 85-86. Optionally, the cover seal 510 may have a pair of locking pins 512 that interlock with a pair of holes 514 in the first and second tines 502, 504 to secure the fork-shaped binder 500 in the closed position. Alternatively or in addition, the cover seal 510 may have a contact adhesive to lock and seal the surgical closure device 490 in the dosed position.

FIG. 87 illustrates an optional incision template 590 that can be used with the surgical closure device 490 in FIGS. 81-86. The incision template 590 fits over the surgical closure device 490 when it is in a closed or partially-open position. A central slot 592 has downwardly-extending lips 594 that extend into the opening 493 to protect the first sleeve 496 and the second sleeve 498 from being cut when the incision is being made. The incision template 590 is preferably made of a rigid or semi-rigid polymer or metal that will resist being cut by a scalpel or other cutting device. The incision template 590 is also adaptable for use with other embodiments of the surgical closure device described herein.

FIG. 88 illustrates a variation of the fork-shaped binder 500 that has an inwardly convex, arcuate or bowed curvature to the tines 502, 504 so that, when the fork-shaped binder 500 is locked in a closed position, an increased closing pressure is applied over the center of the incision.

Figure 84:
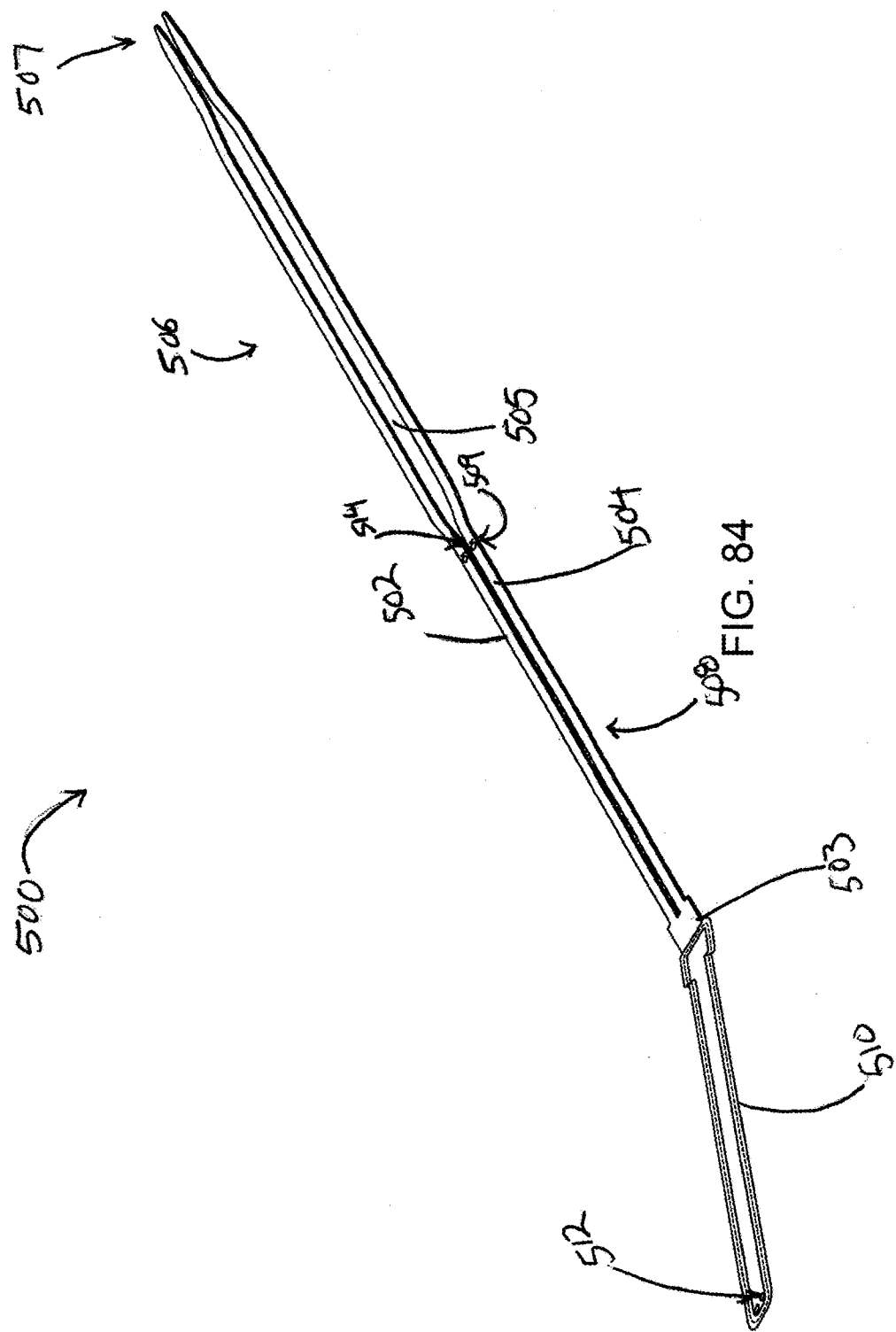

FIG. 89 illustrates a variation of the fork-shaped binder 500 that serves a similar function to the partially-open section 506 of the fork-shaped binder 500 shown in FIG. 84. This variation of the fork-shaped binder 500 has a gap 505 between the tines 502, 504 to apply a spreading force to the opening 493 in the surgical closure device 490 and to the skin underneath to facilitate making an incision through the opening 493.

Figure 90:
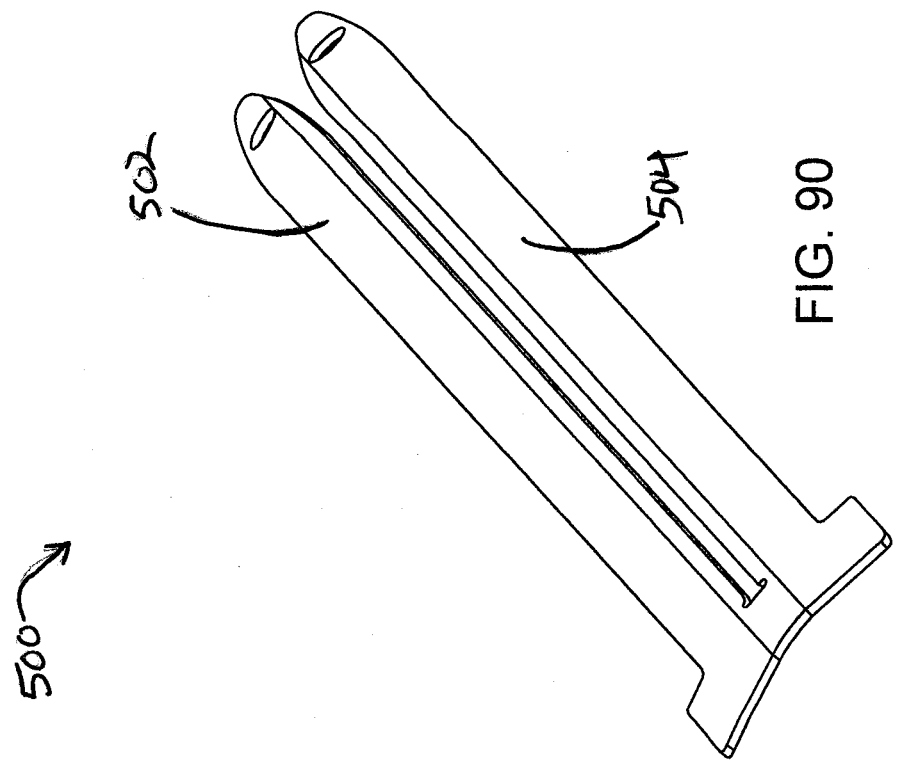
FIG. 90 illustrates a fork-shaped binder configured to lift the tissue adjacent to the incision when the surgical closure device is in a closed position.

FIG. 90 illustrates a variation of the fork-shaped binder 500 that is configured to lift the tissue adjacent to the incision when the surgical closure device 490 is in a closed position. The first tine 502 and the second tine 504 are angled upward so that, when the fork-shaped binder 500 is inserted into the first sleeve 496 and the second sleeve 498, the tissue adjacent to the incision is lifted up. Lifting the tissue adjacent to the incision is intended to reduce subsidence or retraction of the tissue that frequently occurs during the healing process. This should result in reduced scar formation and improved cosmesis. Similarly, other styles of binders that are described herein can also be configured to lift the tissue adjacent to the incision when the surgical closure device is in a closed position.

Figure 91:
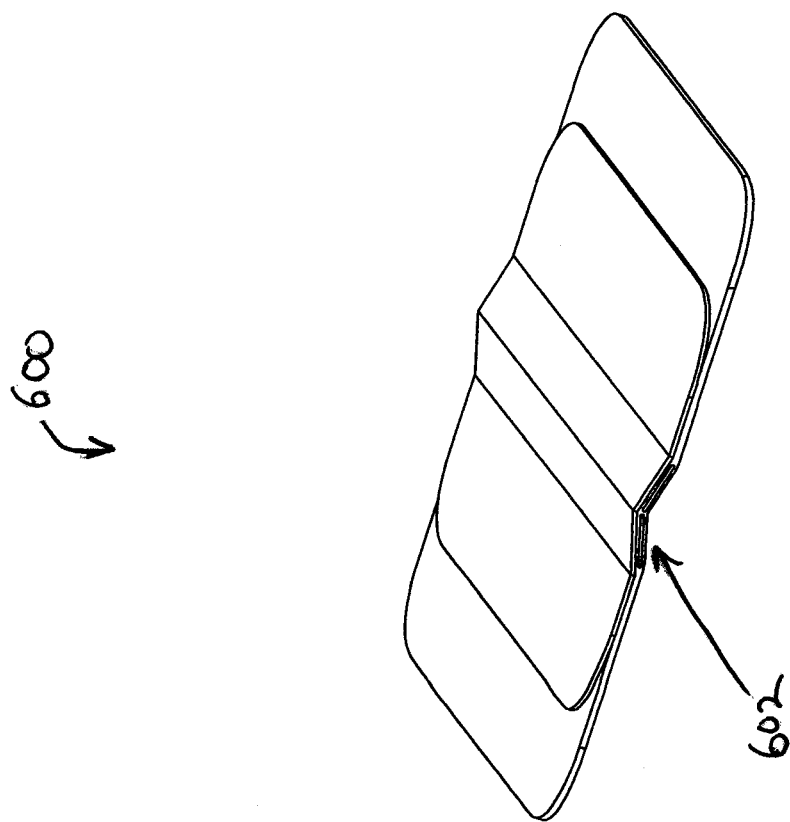
FIG. 91 illustrates an adhesive protective cover with a tent-like structure that can be applied along the incision line to raise the tissue adjacent to the incision.

FIG. 91 shows another optional feature that can be used to raise the tissue adjacent to the incision when the surgical closure device is in a closed position. An adhesive protective cover 600 has a tent-like structure 602 that can be applied along the incision line to raise the tissue adjacent to the incision. The tent-like structure 602 may be made of a polymer or metal of sufficient stiffness to raise the tissue adjacent to the incision. The protective cover 600 can be applied at the time the incision is closed or may be applied later after initial healing has taken place. For example, once initial healing has taken place, the binder can be removed and the protective cover 600 can be applied over the surgical closure device. Optionally, the tent-like structure 602 may be made of a material that is resilient enough that it can be flattened to apply it over the surgical closure device using a contact adhesive. Then, when it is released, the elastic resilience of the tent-like structure 602 lifts the tissue adjacent to the incision.

Figure 92:
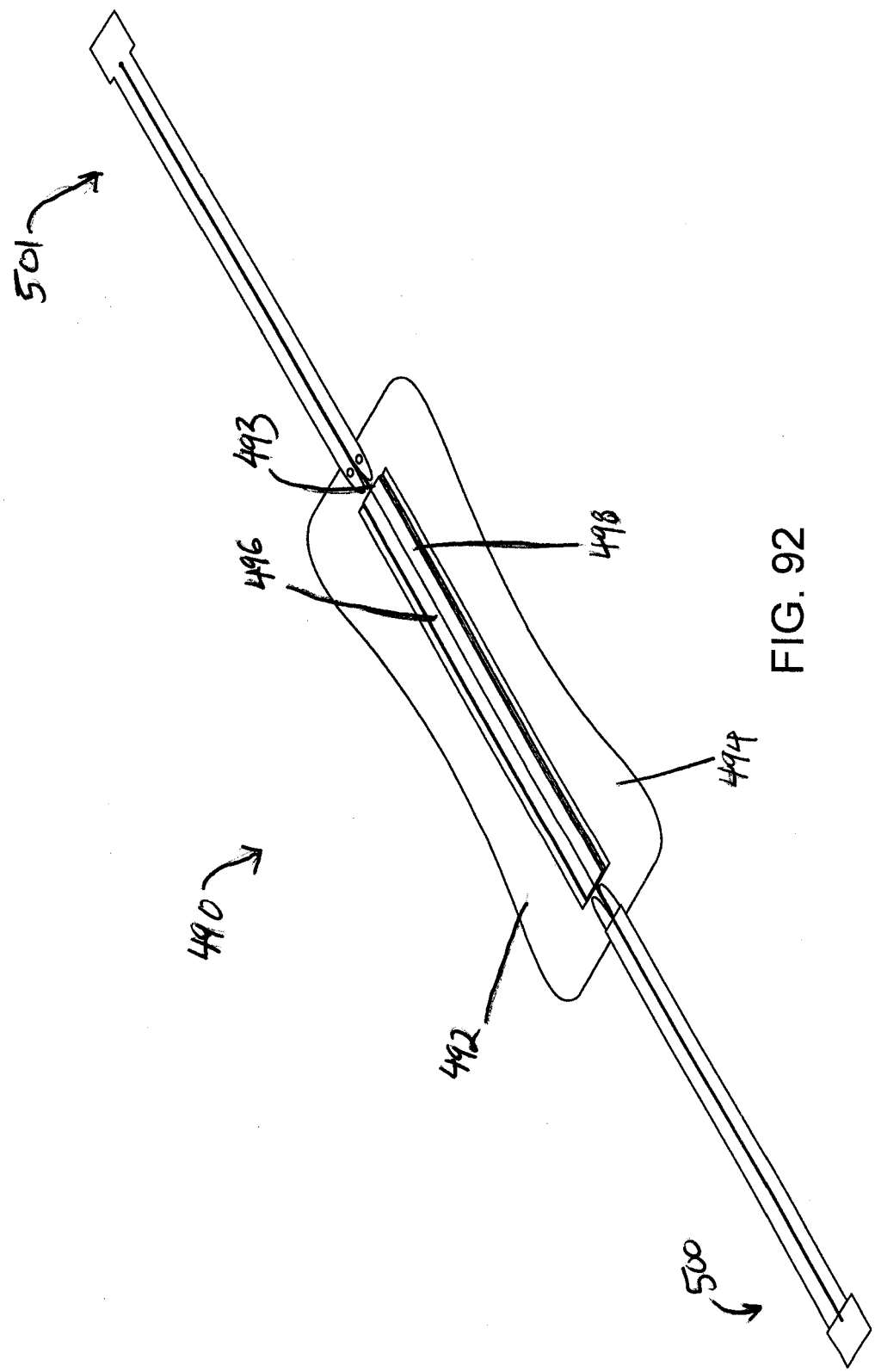
FIGS. 92-94 illustrate a surgical closure device with two fork-shaped binders that are inserted from opposite ends of the sleeves to hold the surgical closure device in a closed position.
Figure 93:
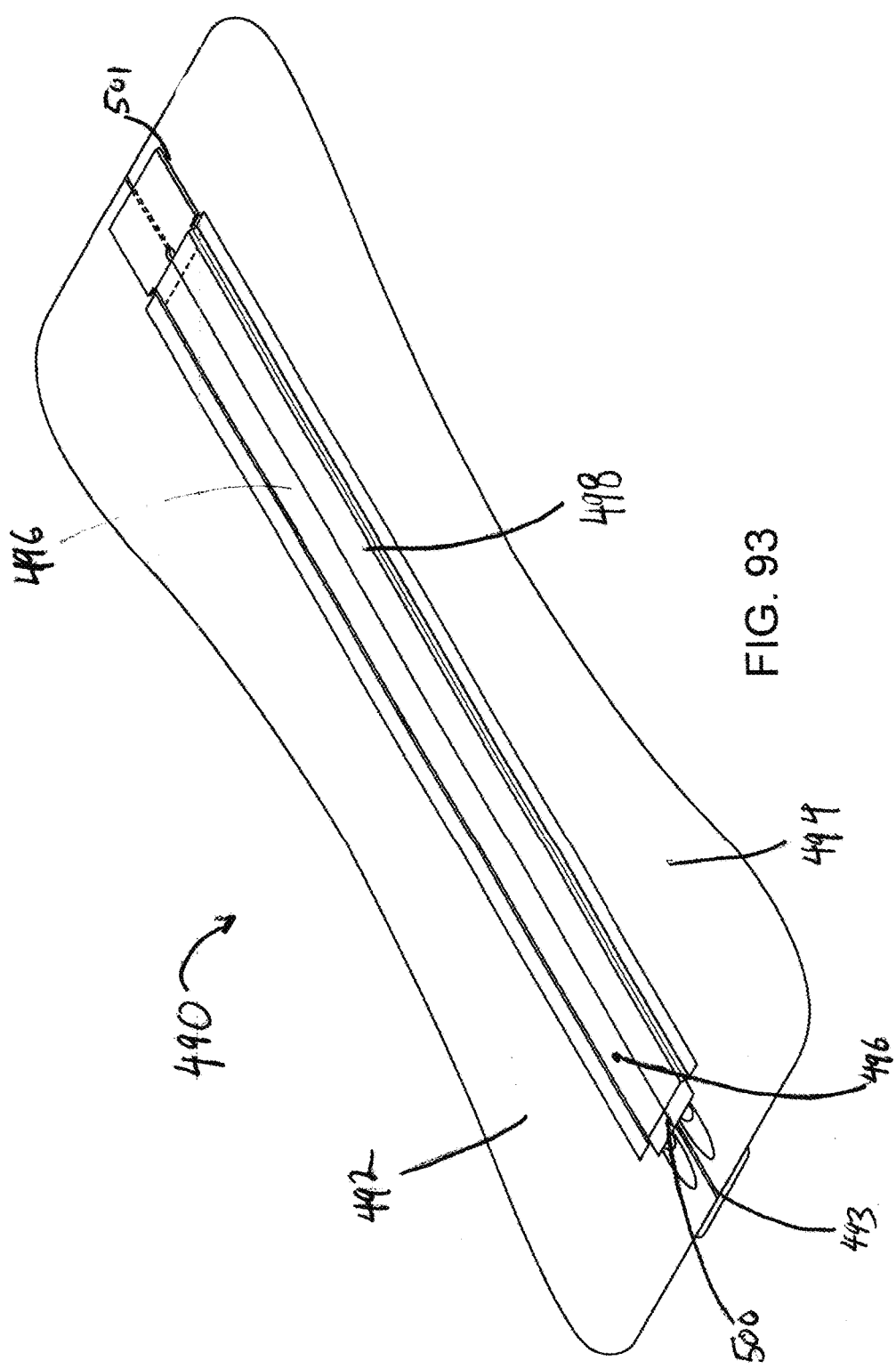
Figure 94:
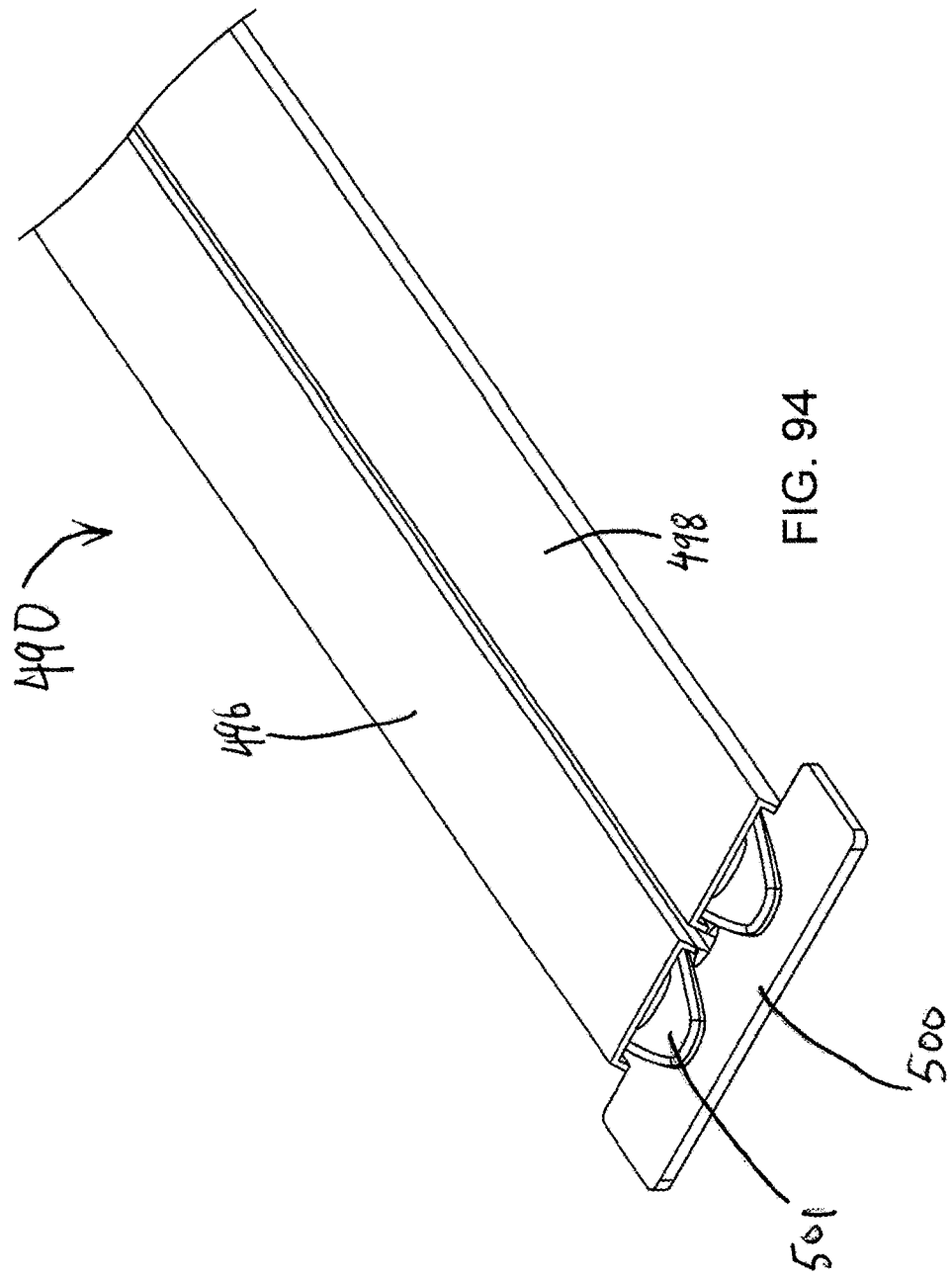

FIGS. 92, 93 and 94 illustrate another variation of the surgical closure device 490 of FIGS. 81-86 that utilizes first and second fork-shaped binders 500, 501 that are inserted from opposite ends of the first and second sleeves 496, 498 to hold the surgical closure device 490 in a closed position. FIG. 92 shows the surgical closure device 490 prior to insertion of the first and second fork-shaped binders 500, 501 and FIG. 93 shows the surgical closure device 490 in the closed position, after insertion of the first and second fork-shaped binders 500, 501. Using two fork-shaped hinders 500, 501 provides additional security to the surgical closure device 490 in the closed position. Optionally, the first and second fork-shaped binders 500, 501 may fit together telescopically, as shown in FIG. 94, and/or may have locking features to lock the first and second fork-shaped binders 500, 501 together.

The first and second fork-shaped binders 500, 501 can also be used to provide a surgical closure device 490 with customizable length. The first adhesion patch 492 and the second adhesion patch 494 may be cut to the desired length to fit the intended incision or an existing incision or wound. A fork-shaped binder 500 of the appropriate length may be inserted into the cut ends of sleeves 496, 498 to hold the cut end of the opening 493 together. If desired, the first and second fork-shaped binders 500, 501 may be different lengths. For example, a very short first fork-shaped binder 500 may be just long enough to hold the cut end of the of sleeves 496, 498 and opening 493 together until the second fork-shaped binder 501 is inserted to close the incision.

Figure 95:
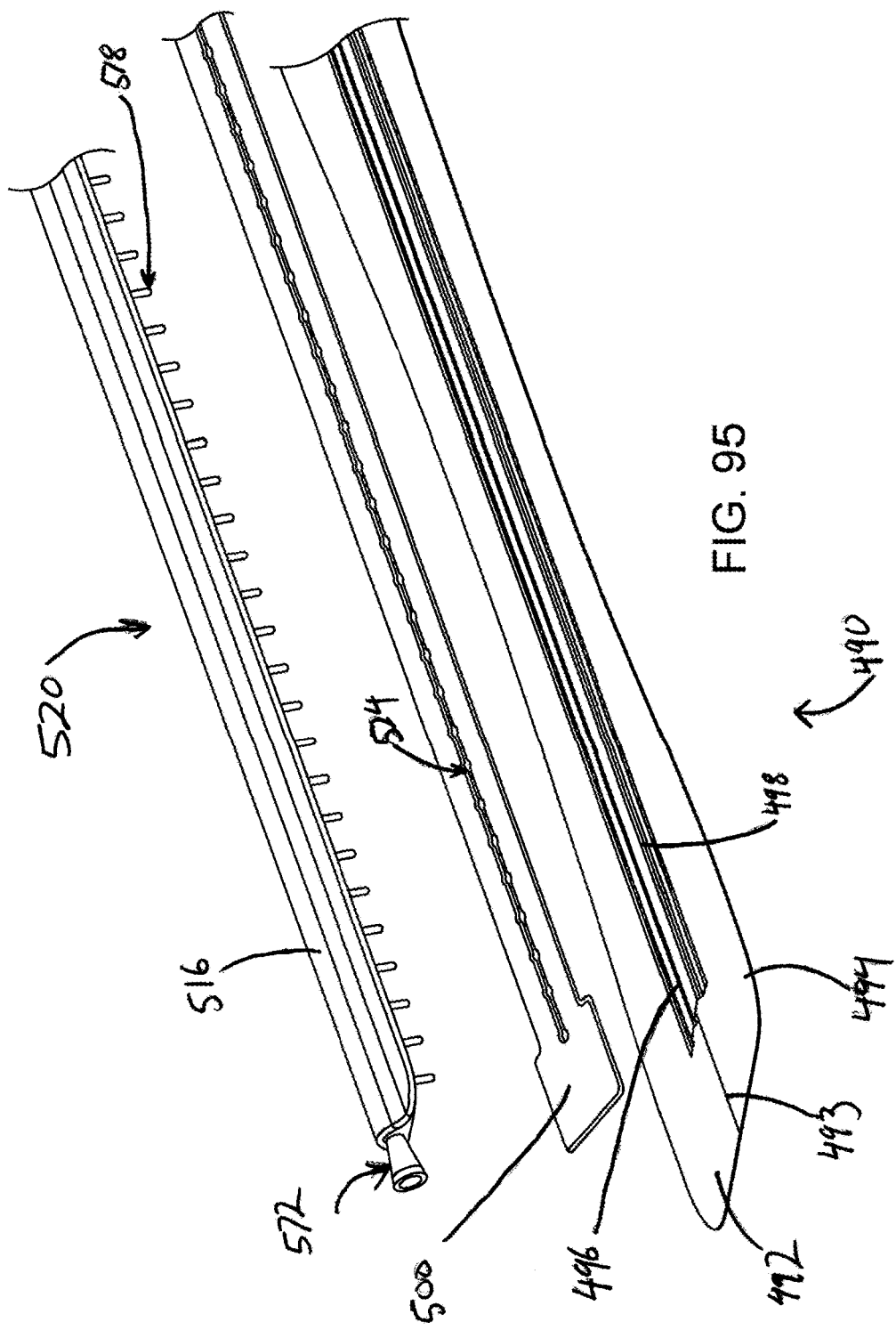
FIGS. 95-96 illustrate the surgical closure device of FIGS. 81-86 with a drug injection manifold.
Figure 96:
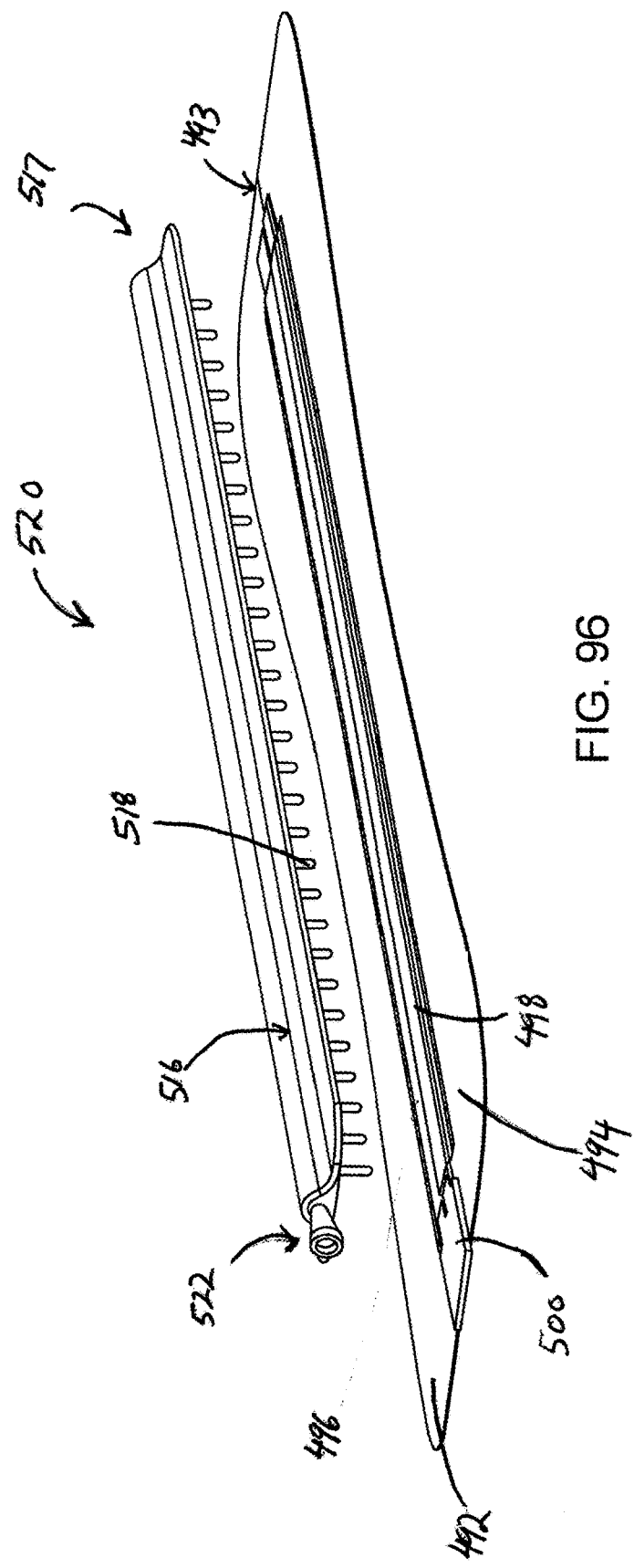

FIGS. 95-96 illustrate additional features that may be used with the surgical closure device 490 in FIGS. 81-86. A drug injection manifold 520 has a main tube 516 with a proximal connector 522, such as a Luer fitting, and a closed distal end 517. At least one, and preferably several, drug injection needles or catheters 518 are connect to the main tube 516. As shown in the exploded view in FIG. 95, the fork-shaped binder 500 has a series of holes 524 that allow the drug injection needles or catheters 518 to be inserted into the incision while the surgical closure device 490 is in the closed position. FIG. 96 also illustrates that the fork-shaped binder 500 may be shortened so that it only includes the closed section 506 and optionally, a tapered end section 507. Optionally, the drug injection manifold 520 may also include a contact adhesive and/or locking pins or other locking features to seal and secure the surgical closure device 490 in the closed position. The drug injection manifold 520 may be inserted while the wound is still open or after the surgical closure device 490 has been closed, as shown in FIG. 96.

Figure 97:
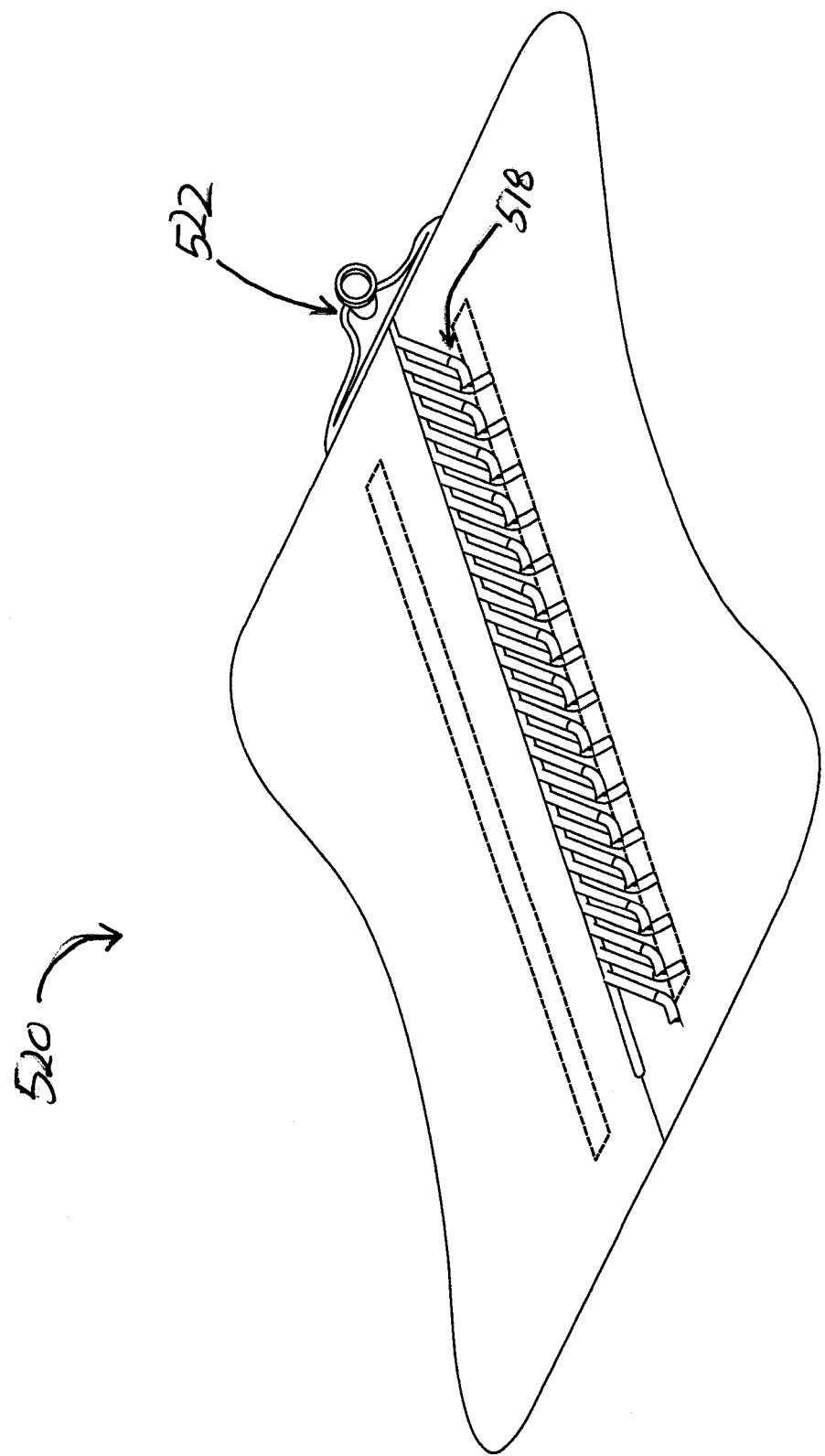
FIG. 97 illustrates a drug injection manifold with drug injection needles or catheters that are curved alternately to the left and right.

FIG. 97 illustrates another variation of the drug injection manifold 520, wherein the drug injection needles or catheters 518 are curved alternately to the left and right so that a drug, such as an anesthetic, will be injected into the tissue on both sides of the incision.

Figure 98:
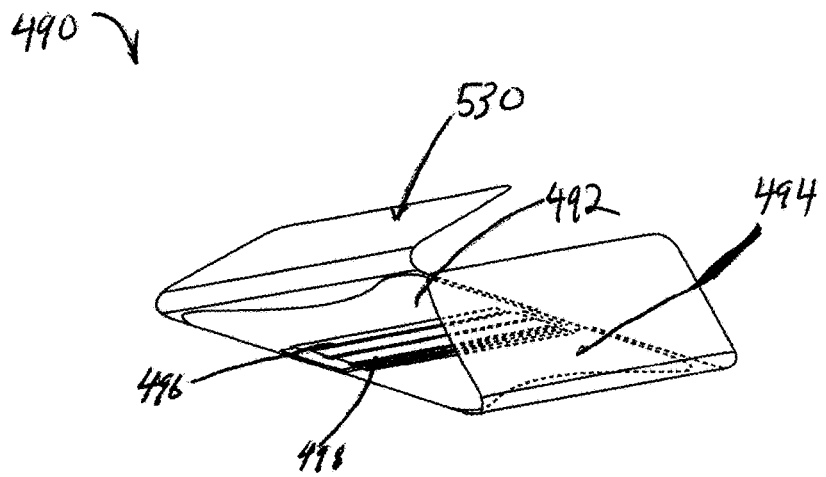
FIGS. 98-99 illustrate an impermeable or hydrophobic protective cover that is applied over the surgical closure device.
Figure 99:
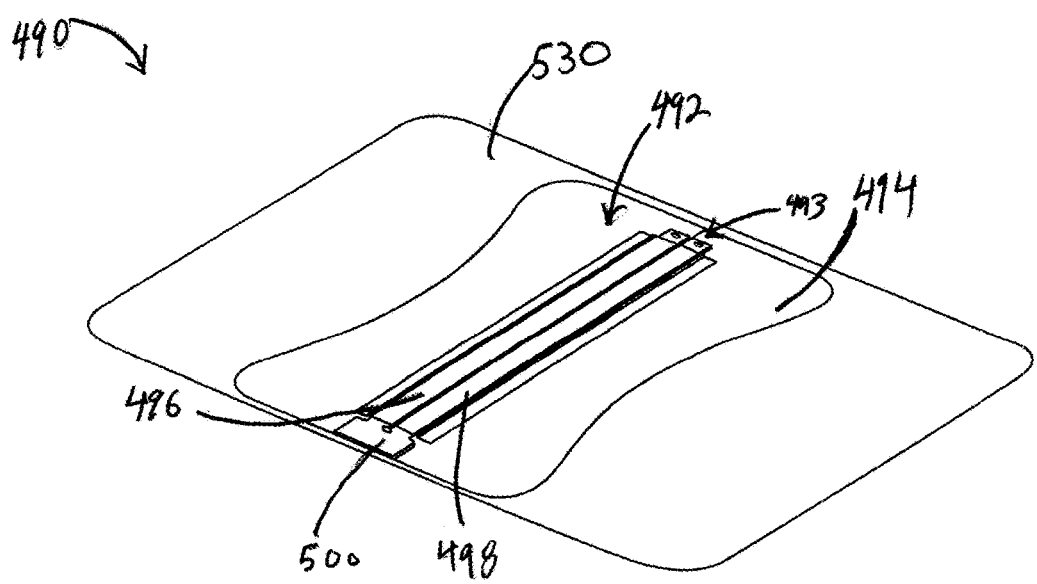

FIGS. 98-99 illustrate an optional feature that may be used with any of the embodiments of the surgical closure device described herein. An impermeable and/or hydrophobic protective cover 530 is applied over the surgical closure device 490 to protect it from absorbing and/or being stained by blood or other contaminants during use. The protective cover 530 may be clear, translucent or opaque. During manufacturing, the protective cover 530 may be folded onto the upper surface of the surgical closure device 490, as shown in FIG. 98, so that it can be unfolded to cover a larger area in use, as shown in FIG. 99. The protective cover 530 is preferably adhered to the surgical closure device 490 and the patient's skin with a weak contact adhesive so that it can be removed after surgery to leave a clean surface underneath without discomfort to the patient or danger of moving or dislodging the surgical closure device 490.

FIGS. 100-105 illustrate another embodiment of a surgical closure device 540 configured for making and closing a shaped incision in the patient's skin, such as a wedge biopsy incision. The surgical closure device 540 is similar in many respects to the embodiments of FIGS. 16 and 62. There is a nonlinear shaped opening 548 between the first adhesion patch 542 and the second adhesion patch 544 that defines the shape of the incision. in one particularly preferred embodiment, the shaped opening 548 has the geometry of an ellipse or a rounded lozenge shape somewhat like the shape of an American football or a convex-convex lens. A first sleeve 552 and a second sleeve 554 follow the outline of the shaped opening 548. Preferably, the first and second adhesion patches 542, 544 are joined together beyond the ends of the shaped opening 548. The first adhesion patch 542, the second adhesion patch 544, the first sleeve 552 and the second sleeve 554 are made of flexible materials that allow the shaped opening 548 to move from an open position to a closed position. Optionally, the shaped opening 548 may be biased toward the open position or the closed position.

Figure 100:
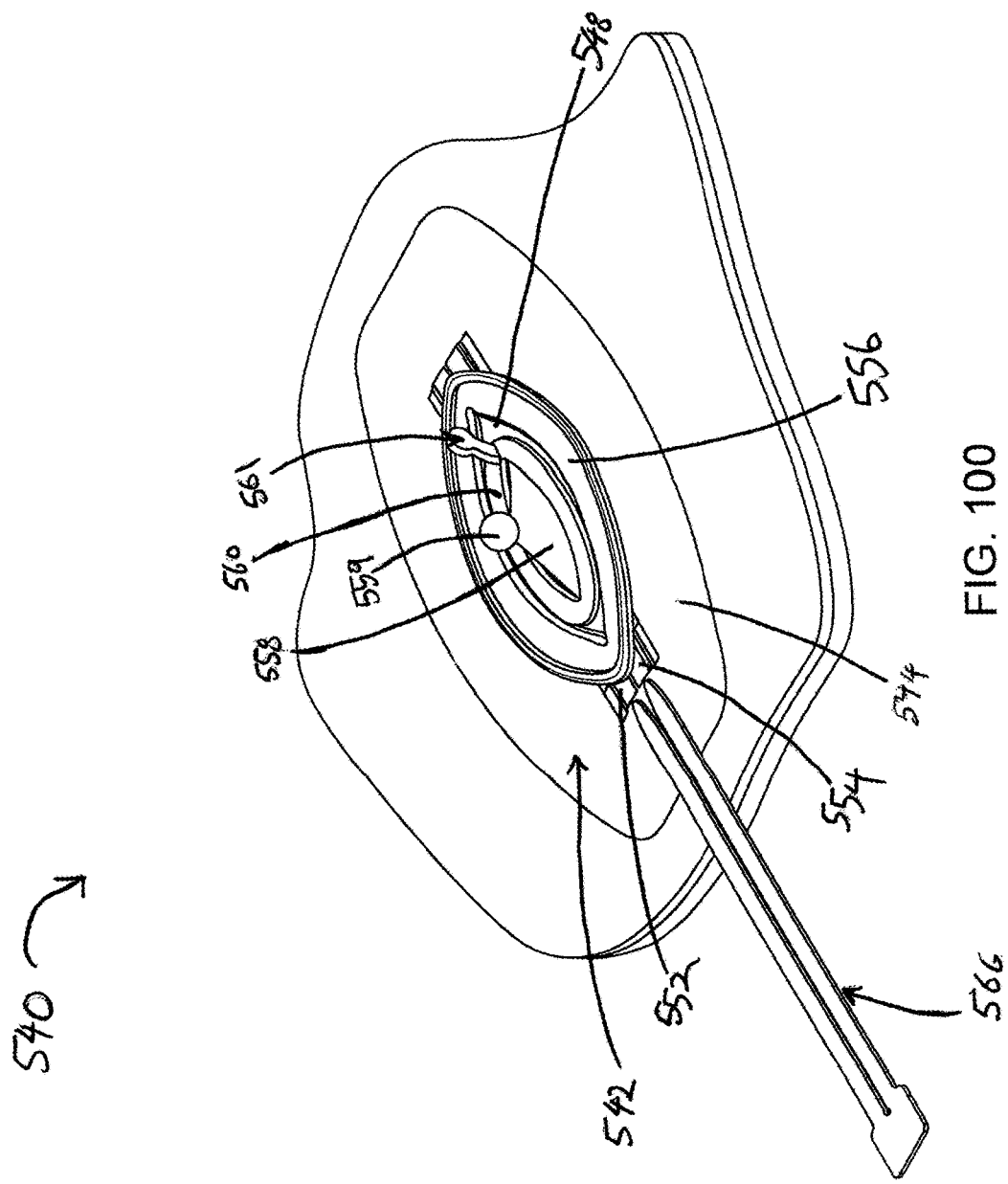
FIGS. 100-105 illustrate a surgical closure device for making and closing a shaped incision in the patient's skin, such as a wedge biopsy incision.

Positioned within the shaped opening 548, when the surgical closure device 540 is in an open position as shown in FIG. 100, is an incision template 556 that follows the contours of the shaped opening 548 and protects the surgical closure device 540 from being accidentally cut when the incision is being made. The incision template 556 may also serve to hold the shaped opening 548 in the open position inside of the incision template 556 is a shaped insert 558 that has approximately the same shape as the shaped opening 548 and a spacer 560 between the incision template 556 and the shaped insert 558. There is a spacer handle 561 attached to the spacer 560 and an insert handle 559 attached to the shaped insert 558. In one particularly preferred embodiment, the spacer handle 561 is shaped somewhat like a joystick controller. The shaped insert 558 has a contact adhesive on its lower surface 562. Alternatively or in addition, the shaped insert 558 can have hooks, barbs, forceps jaws, suction cups or other means on the lower surface 562 for gripping the patient's skin.

Figure 101:
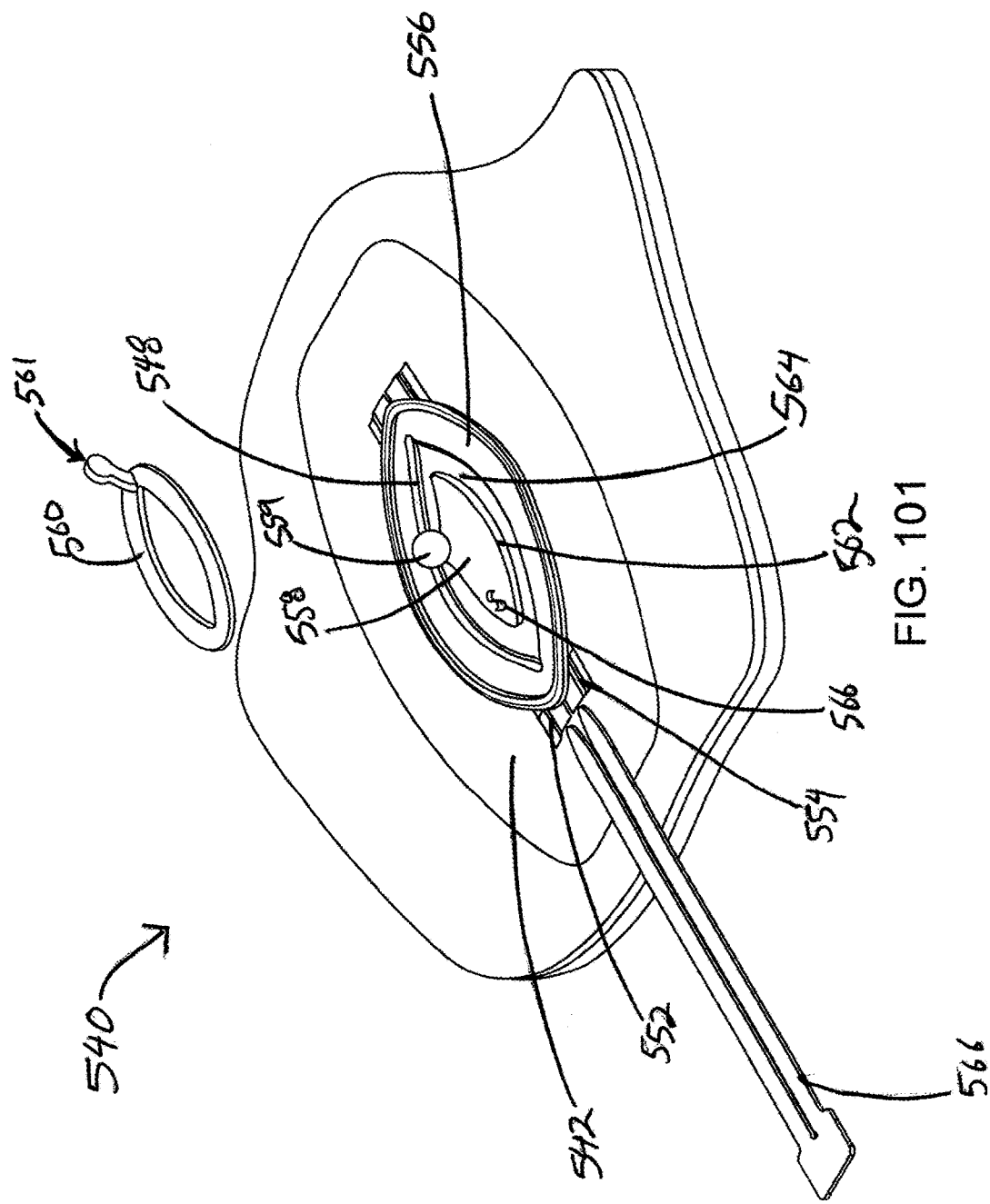
Figure 102:
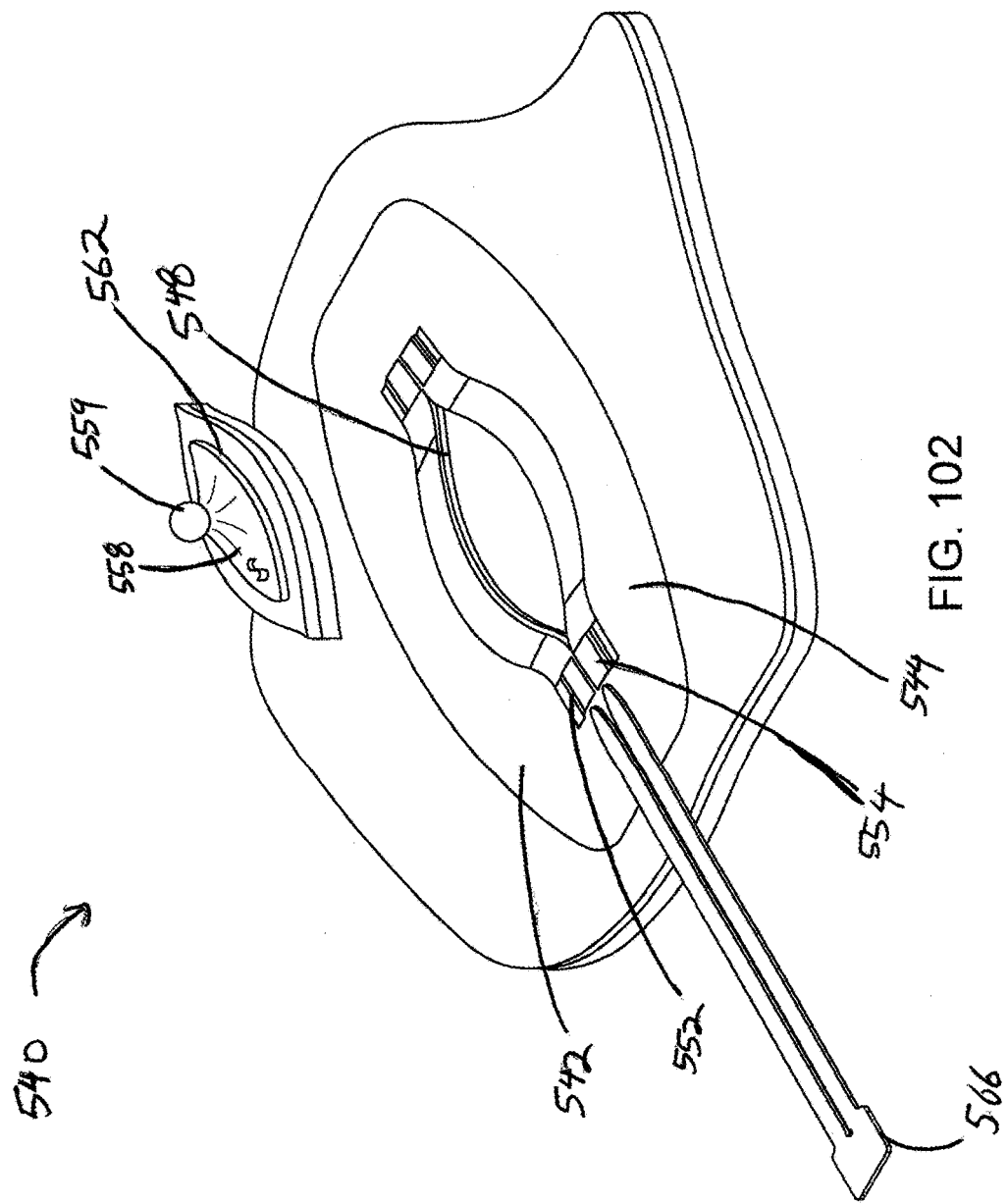

In use, the surgical closure device 540 is adhered to the patient's skin with contact adhesive on the first adhesion patch 542, the second adhesion patch 544 and the shaped insert 558, as shown in FIG. 100. Preferably, the shaped insert 558 is somewhat transparent so that the surgical closure device 540 can be accurately positioned with the shaped opening 548 around a suspected lesion. Then, the spacer 560 is lifted out using the spacer handle 561, as shown in FIG. 101, leaving a narrow gap 564 between the incision template 556 and the shaped insert 558 sufficient for insertion of a scalpel blade or other cutting instrument. Using the insert handle 559 on the shaped insert 558, the surgeon can lift and tension the skin to facilitate making an incision and enable cutting the bottom of the biopsy sample to be removed. The biopsy sample can be manipulated while making the incision and conveniently lifted out using the insert handle 559 after the incision is made, as shown in FIG. 102.

In an alternative configuration, the shaped insert 558 could also have a cutting blade along the lower edge, like a cookie cutter or a punch biopsy device, to cut the skin and tissue around the biopsy sample to be removed. Optionally, the shaped insert 558 may include one or more indicia 566 to indicate the orientation of the biopsy sample. The indicia 566 may indicate the orientation of the biopsy sample with respect to the patient's anatomy (e.g. "S" for "superior") and/or one or more corresponding indicia may be provided on the surgical closure device 540. Alternatively, one or more indicia may be provided for attachment directly to the biopsy sample, for example using contact adhesive.

Figure 103:
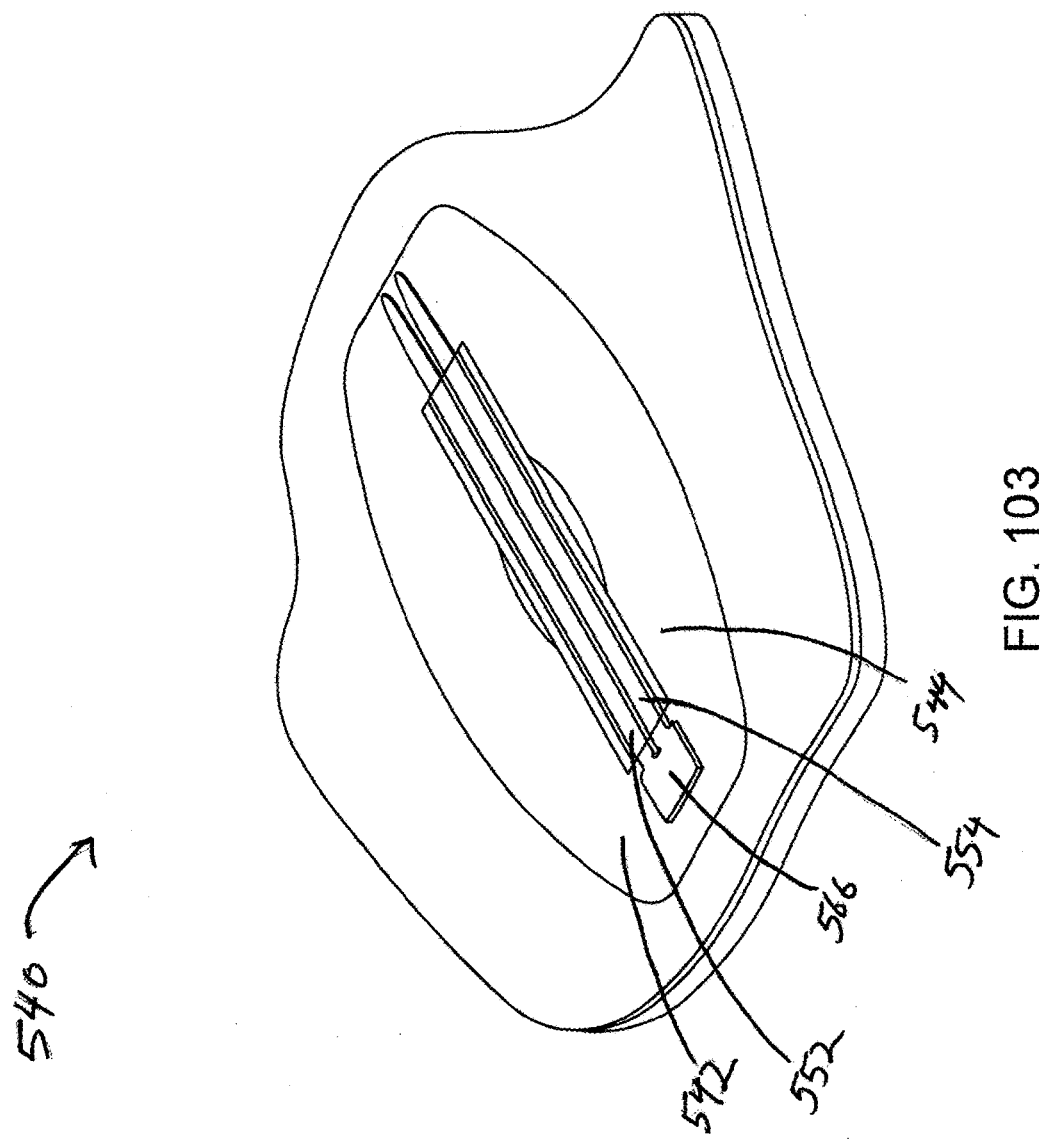

Next, the incision template 556 is removed and a fork-shaped binder 566 is inserted into the first sleeve 552 and the second sleeve 554 to close the shaped opening 548, as shown in FIG. 103. Optionally, a seal strip and/or a drug infusion manifold may be used with the surgical closure device 540.

Figure 104:
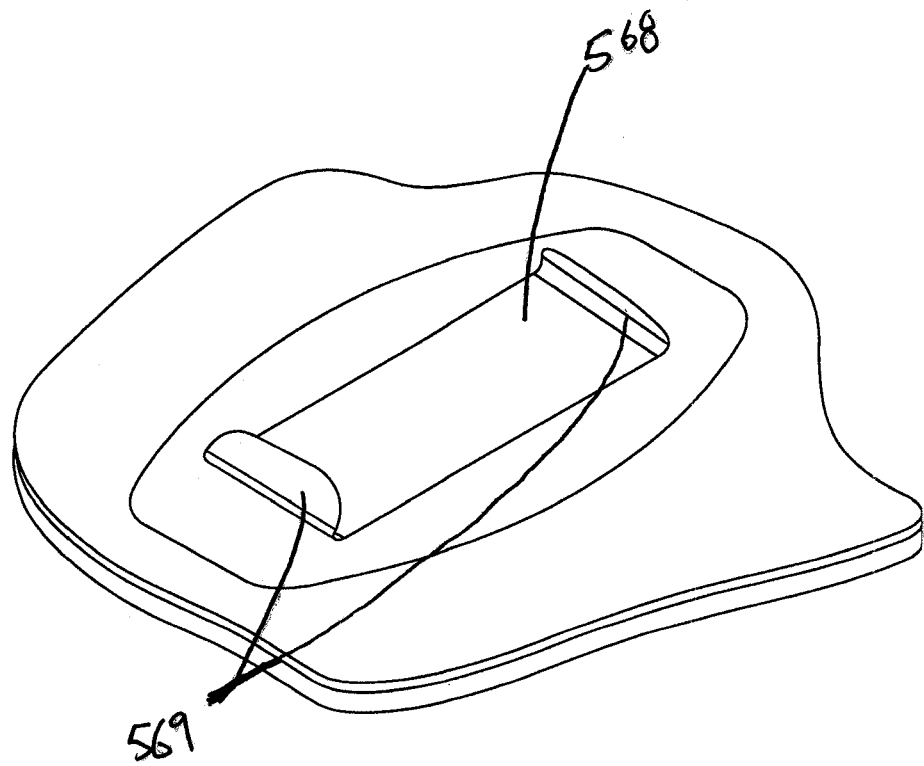
Figure 105:
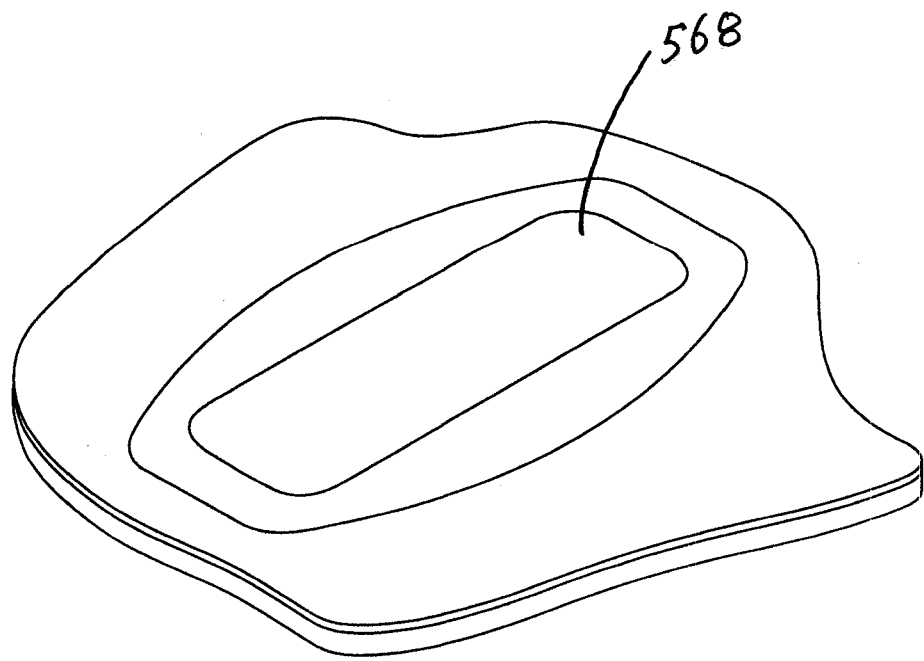

Optionally, the surgical closure device 540 may include a protective cover 568 that can be applied over the opening 548 with a contact adhesive after the incision has been closed, as shown in FIGS. 104-105. The protective cover 568 will seal the surgical closure device 540 against potential contamination and will add strength to the closure. Optionally, the fork-shaped binder 566 may be removed after the protective cover 568 has been applied or after an initial period of healing has taken place. The surgical closure device 540 will be more flexible and more comfortable for the patient after the binder 566 has been removed. FIG. 104 shows the protective cover 568 in a partially-closed position with the ends 569 lifted to allow access to the ends of the fork-shaped binder 566 for easy removal of the binder 566 while securing the surgical closure device 540 in a closed position. After the binder 566 has been removed, the ends 569 of the protective cover 568 are adhered down to fully seal the surgical closure device 540, as shown in FIG. 105.

Figure 106:
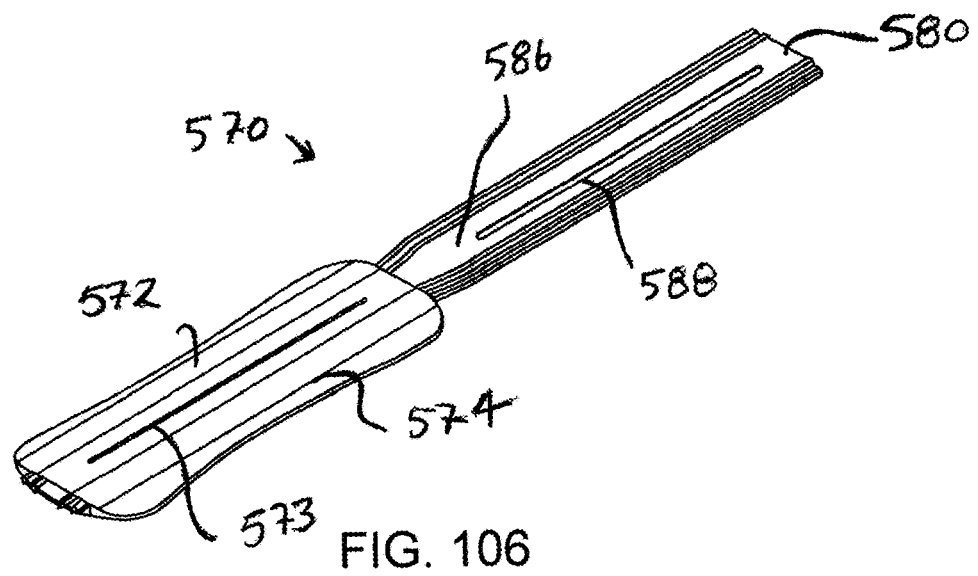
FIGS. 106-107 illustrate a low-profile surgical closure device having an internal binder.
Figure 107:
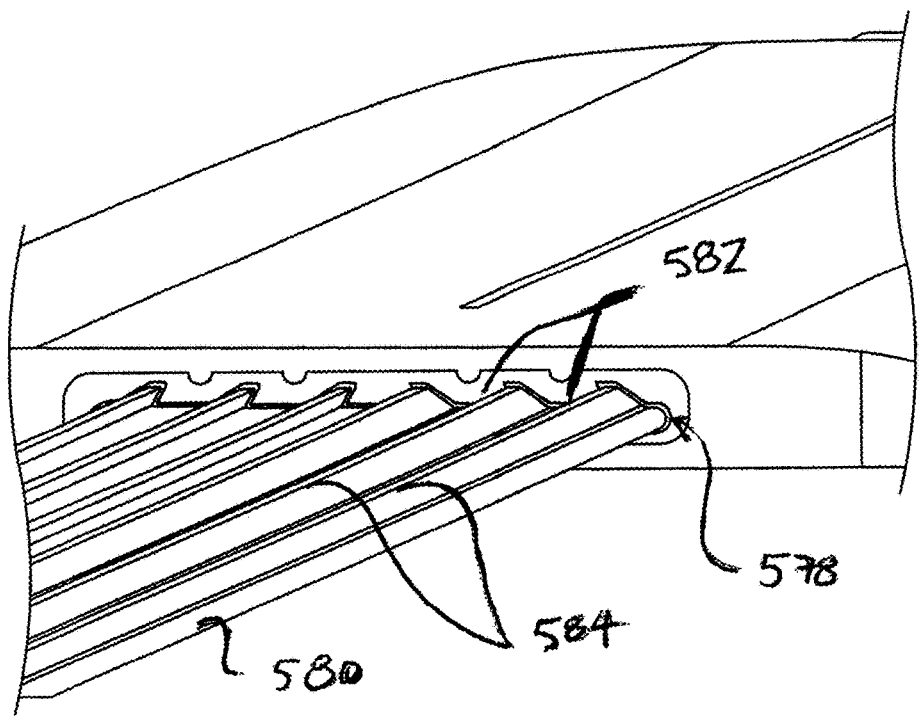

FIGS. 106-107 illustrate another embodiment of a low-profile surgical closure device 570. The surgical closure device 570 has a first adhesion patch 572 and a second adhesion patch 574 that meet along an opening 573 that defines an incision line. The first adhesion patch 572 and the second adhesion patch 574 are joined together beyond the ends of the opening 573. An internal slot 578 extends through the surgical closure device 570 below the opening 573. An internal binder 580 is sized and configured to slide into the internal slot 578 to bind the first adhesion patch 572 and a second adhesion patch 574 together when in the closed position, as shown in FIG. 106. Preferably, the internal slot 578 is formed with undercuts 582 that interlock with corresponding ridges 584 on the internal binder 580, as shown in the close-up view in FIG. 107.

Optionally, the internal binder 580 may be made with a partially-open portion 586 with an incision guide slot 588 along the centerline. The partially-open portion 586 is somewhat wider than the remainder of the internal binder 580 so that, when it is positioned within the internal slot 578, it stretches the opening 573 and the skin beneath the opening 573 in order to facilitate making an incision through the incision guide slot 588. The partially-open portion 586 may be, broken off or cut off of the internal binder 580 after the surgical closure device 570 has been closed.

The surgical closure device 570 of FIGS. 106-107 may also be used for applying a surgical adhesive (e.g. a cyanoacrylate, fibrin, albumin or glutaraldehyde based adhesive) for closure of the skin incision after surgery. The surgical closure device 570 and the internal binder 580 would be made of or coated with a material, such as PTFE or HDPE, that does not bond with the surgical adhesive. With the partially-open portion 586 of the internal binder 580 positioned within the internal slot 578, the incision would be spread open with a predetermined gap so that a metered amount surgical adhesive could be applied. Then, the internal binder 580 would be moved to the closed position to close the incision. Optionally, the internal binder 580 may be removed after the surgical adhesive has cured.

As mentioned previously, the surgical closure device of the present invention may be configured as a single device that extends the entire length of the incision or, alternatively, the device may be modular and made up of either separate or interconnected segments. A modular surgical closure device would be particularly useful for closing long incisions, such as those used for surgical removal of redundant skin following successful bariatric surgery.

Figure 108:
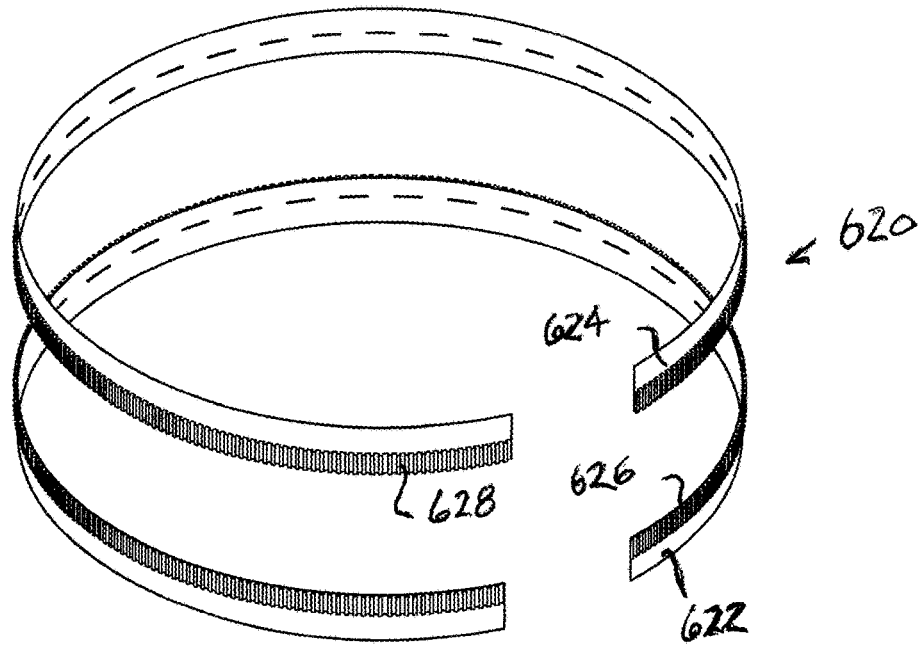
FIGS. 108-109 illustrate an elongated surgical closure device that uses modular fork-shaped binders to close an elongated incision.
Figure 109:
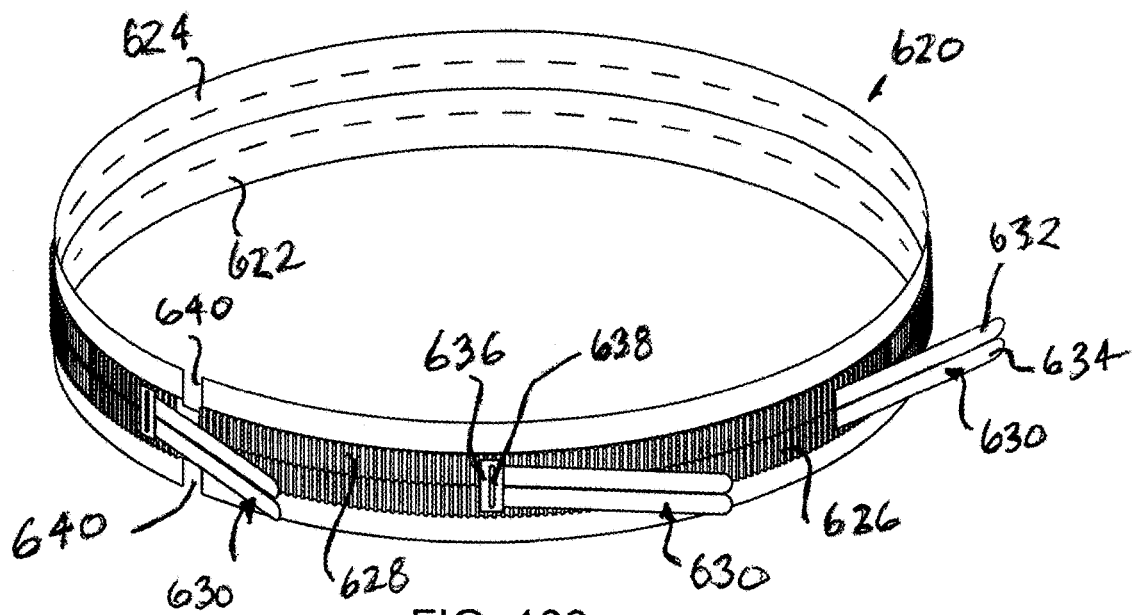

One method of interconnecting modular segments is with modular binders that connect end-to-end. FIGS. 108-109 illustrate an elongated surgical closure device 620 that uses modular fork-shaped binders 630 to close an elongated incision. FIG. 109 shows an elongated surgical closure device 620 that has a first adhesion patch 622 and a second adhesion patch 624 with a first sleeve 626 and a second sleeve 628 positioned along adjacent edges of the first adhesion patch 622 and the second adhesion patch 624. In one particularly preferred embodiment, the first sleeve 626 and the second sleeve 628 are segmented to allow the first adhesion patch 622 and the second adhesion patch 624 to be very flexible so that it can be placed along a curving or irregular incision line on the patient. The first adhesion patch 622 and the second adhesion patch 624 may be long enough to surround the entire circumference of the patient or multiple shorter adhesion patches 622, 624 may be adhered to the skin end-to-end along the intended incision lines.

After excision of the redundant skin between the first adhesion patch 622 and the second adhesion patch 624, the first sleeve 626 and the second sleeve 628 are brought into close alignment with one another. Then, the tines 632, 634 of a fork-shaped binder 630 are inserted through the sleeves 626, 628 to close a first segment of the incision. The tines 632, 634 of another fork-shaped binder 630 are inserted through the sleeves 626, 628 to close a second segment of the incision, and so on until the entire length of the incision has been closed, as shown in FIG. 109. Optionally, each of the fork-shaped binders 630 may have a T-shaped head 636 with a slot 638 for inserting the ends of the tines 632, 634 of the adjacent fork-shaped binder 630 so that the fork-shaped binders 630 will be linked together end-to-end. Optionally, each of the slots 638 may have a ratchet pawl or other locking mechanism to lock the fork-shaped binders 630 together in the end-to-end configuration. If the first adhesion patch 622 and the second adhesion patch 624 are also modular, that is made in short segments laid end-to-end, then the fork-shaped binders 630 should bridge the gaps 640 between adjacent adhesion patches, as shown in FIG. 109. The gaps 640 between adjacent adhesion patches can be closed by applying tension on the ends of the fork-shaped binders 630.

Additional features may be combined with any of the surgical closure devices disclosed herein:

Optionally, the rails and the binder of the surgical closure device may be configured to provide a small amount of compression at the incision in the closed position such that the edges of the incision turn upward slightly. This technique may provide better healing of the incision in some circumstances.

Optionally, the binder may be made with lateral reinforcements that provide additional strength for secure closure. The lateral reinforcements may be U-shaped or C-shaped and embedded in or wrapped around a flexible polymer channel to provide lateral strength while allowing the binder to be very flexible. The lateral reinforcements may be made of metal, such as stainless steel, or rigid plastic or a fiber reinforced composite. The lateral reinforcements may also be constructed as a continuous wire form that is provides lateral strength, but allows flexibility of the binder. The wire form could be configured as a serpentine or wave-like formation that is embedded in or wrapped around the binder channel in U-shaped or C-shaped cross section.

The surgical closure device of the present invention can also be combined with other wound healing modalities, for example hyperbaric oxygen therapy, suction therapy, stem cell implantation, wound drainage, etc. Oxygen can be supplied to the surgical closure device by hydrolysis using a small reservoir of water and a battery within the device or connected to it.

While the present invention has been described herein with respect to the exemplary embodiments and the best mode for practicing the invention, it will be apparent to one of ordinary in the art that many modifications, improvements and subcombinations of the various features and embodiments, adaptations and variations can be made to the invention without departing from the spirit and scope thereof.

What is claimed is:

1. An incision closure device comprising:
   a first adhesion patch configured for adhering to a patient's skin adjacent a first side of an incision;
   a second adhesion patch configured for adhering to the patient's skin adjacent a second side of the incision;
   a binding mechanism configured for laterally coupling the first and second adhesion patches to one another across the incision; and
   at least one injection manifold coupled to at least one of the first or second adhesion patch, the at least one injection manifold being configured to deliver fluid to or under the patient's skin when one or more of the first or second adhesion patches are adhered to the patient's skin,
   wherein the at least one injection manifold comprises:
      a main tube,
      a plurality of injection catheters coupled to the main tube and extending from an underside of at least one of the first or second adhesion patches, each injection catheters having a catheter lumen, and
      a plurality of injection needles configured to extend through the catheter lumens of the plurality of injection catheters, wherein the plurality of injection needles are configured to puncture the patient's skin to form a plurality of punctures therein and allow the plurality of injection catheters to extend into the plurality of punctures when at least one of the first or second adhesion patches is adhered to the patient's skin adjacent the incision, and wherein the plurality of injection needles are configured to be retractable from the catheter lumens of the plurality of injection catheters to allow the fluid to be delivered through the plurality of injection catheters to or under the patient's skin.

2. The incision closure device of claim 1, wherein the at least one injection manifold is aligned axially with at least one of the first or second adhesion patches.

3. The incision closure device of claim 1, wherein the at least one injection manifold comprises a first injection manifold coupled to the first adhesion patch and a second injection manifold coupled to the second adhesion patch.

4. The incision closure device of claim 3, further comprising at least one proximal connector coupled to at least one of a proximal end of the first injection manifold or a proximal end of the second injection manifold to deliver fluid to at least one of the first or second injection manifolds.

5. The incision closure device of claim 4, wherein the at least one proximal connector comprises a Luer fitting with a removable and replaceable cap.

6. The incision closure device of claim 4, wherein the at least one proximal connector comprises a first proximal connector and a second proximal connector, the first proximal connector being coupled to a proximal end of the first injection manifold to deliver fluid to the first injection manifold and the second proximal connector being coupled to a proximal end of the second fluid injection manifold to delivery fluid to the second injection manifold.

7. The incision closure device of claim 4, wherein the at least one proximal connector comprises a single proximal connector coupled to the proximal ends of the first and second injection manifolds.

8. The incision closure device of claim 4, further comprising a syringe or an ampoule coupled to the at least one proximal connector to provide the fluid to be delivered by the at least one injection manifold.

9. The incision closure device of claim 8, wherein the syringe or ampoule is squeezable to deliver the fluid to the at least one injection manifold.

10. The incision closure device of claim 4, further comprising a fluid pump coupled to the at least one proximal connector to deliver the fluid to the at least one injection manifold.

11. The incision closure device of claim 4, wherein the at least one proximal connector is removably coupled to the at least one of the proximal end of the first injection manifold or the proximal end of the second injection manifold.

12. The incision closure device of claim 1, wherein the at least one injection manifold is disposed along a midline of at least one of the first or second adhesion patches.

13. The incision closure device of claim 1, wherein at least one of the first adhesion patch, the second adhesion patch, or the at least one injection manifold is coated with at least one of a therapeutic agent, an analgesic agent, an antiseptic agent, an antimicrobial agent, anti-clotting agent, or heparin.

14. The incision closure device of claim 13, wherein the at least one injection manifold comprises an interior surface coated with the at least one of the therapeutic agent, the antiseptic agent, the antimicrobial agent, the anti-inflammatory agent, the anti-clotting agent, or heparin.

15. The incision closure device of claim 1, wherein the plurality of injection catheters are transverse to the main tube.

16. The incision closure device of claim 1, wherein the plurality of injection catheters are splayed relative to one another.

17. The incision closure device of claim 1, wherein the plurality of injection catheters are angled to deliver fluid toward the incision when at least one of the first or second adhesion patches are adhered to the patient's skin.

18. The incision closure device of claim 1, wherein the plurality of injection catheters have different lengths to extend into the plurality of punctures in the patient's skin at different depths.

19. The incision closure device of claim 1, wherein the plurality of injection catheters have the same lengths to extend into the plurality of punctures in the patient's skin at the same depth.

20. The incision closure device of claim 1, wherein the plurality of injection catheters are configured to extend through the patient's skin to a subdermal layer of tissue.

21. The incision closure device of claim 1, wherein the plurality of injection needles are flexible.

22. The incision closure device of claim 1, wherein the plurality of injection needles have different lengths to extend into the plurality of punctures in the patient's skin at different depths.

23. The incision closure device of claim 1, wherein the plurality of injection needles have the same lengths to extend into the plurality of punctures in the patient's skin at the same depth.

24. The incision closure device of claim 1, wherein the plurality of needles are configured to extend through the patient's skin to a subdermal layer of tissue.

25. The incision closure device of claim 1, wherein the at least one injection manifold is embedded in a body of at least one of the first or second adhesion patches.

26. The incision closure device of claim 1, further comprising at least one conductor coupled to at least one of the first or second adhesion patches to generate an intra-tissue electric field to facilitate tissue healing.

27. The incision closure device of claim 26, wherein the at least one conductor comprises a first conductor coupled to the first adhesion patch and a second conductor coupled to the second adhesion patch.

28. The incision closure device of claim 27, wherein the first conductor and the second conductor are oppositely charged.

29. The incision closure device of claim 26, wherein the at least one injection manifold comprises the at least one conductor.

* * * * *